(12) United States Patent
Huang et al.

(10) Patent No.: US 12,049,624 B2
(45) Date of Patent: Jul. 30, 2024

(54) OPTIMIZED SMALL GUIDE RNAS AND METHODS OF USE

(71) Applicant: The Regents of the University of California, Oakland, CA (US)

(72) Inventors: Bo Huang, San Francisco, CA (US); Baohui Chen, San Francisco, CA (US); Lei Qi, Berkeley, CA (US); Luke Gilbert, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 646 days.

(21) Appl. No.: 17/033,255

(22) Filed: Sep. 25, 2020

(65) Prior Publication Data

US 2021/0123046 A1    Apr. 29, 2021

Related U.S. Application Data

(62) Division of application No. 15/025,217, filed as application No. PCT/US2014/058133 on Sep. 29, 2014, now Pat. No. 10,822,606.

(60) Provisional application No. 61/883,929, filed on Sep. 27, 2013.

(51) Int. Cl.
*C12N 15/11* (2006.01)
*C12N 9/22* (2006.01)

(52) U.S. Cl.
CPC ............... *C12N 15/11* (2013.01); *C12N 9/22* (2013.01); *C12N 15/111* (2013.01); *C12N 2310/10* (2013.01); *C12N 2310/20* (2017.05); *C12N 2310/531* (2013.01); *C12N 2800/80* (2013.01); *C12Y 301/00* (2013.01)

(58) Field of Classification Search
CPC ......... C12N 15/11; C12N 9/22; C12N 15/111; C12N 2310/10; C12N 2310/20; C12N 2310/531; C12N 2800/80; C12Y 301/00
See application file for complete search history.

(56) References Cited

U.S. PATENT DOCUMENTS

| | | | |
|---|---|---|---|
| 8,697,359 B1 * | 4/2014 | Zhang | C12N 15/85 435/6.13 |
| 2007/0025970 A1 | 2/2007 | Kingsman | |
| 2009/0298909 A1 | 12/2009 | Pachuk | |
| 2014/0364333 A1 * | 12/2014 | Wu | C12Q 1/6841 506/9 |

OTHER PUBLICATIONS

Jinek et al. A Programmable Dual-RNA-Guided DNA Endonuclease in Adaptive Bacterial Immunity (2012) Science, 337:816-823 (Year: 2012).*
Hsu et al. DNA targeting specificity of RNA-guided Cas9 nucleases (2013) Nature Biotechnology, 31(9):827-832 (Year: 2013).*
International Search Report issued for PCT/US2014/058133, mailed Jan. 8, 2015.
Borodulina, et al. "Transcripts synthesized by RNA polymerase III can be polyadenylated in an AAUAAA-dependent manner." RNA 14, No. 9 (2008): 1865-1873.
Briner, et al. "Guide RNA functional modules direct Cas9 activity and orthogonality." Molecular cell 56, No. 2 (2014): 333-339.
Chen et al., "Dynamic Imaging of Genomic Loci in Living Human Cells by an Optimized CRISPR/Cas System," Cell 155, Dec. 19, 2013, 1479-1491.
Hsu, et al. "DNA targeting specificity of RNA-guided Cas9 nucleases." Nature biotechnology 31, No. 9 (2013): 827-832.
Jinek, et al. "A programmable dual-RNA-guided DNA endonuclease in adaptive bacterial immunity." science 337, No. 6096 (2012): 816-821.
Mali et al., "CAS9 Transcriptional Activators for Target Specificity Screening and Paired Nickases for Cooperative Genome Engineering," Nature Biotechnology, vol. 31, No. 9, Sep. 2013, 833-840.
Matveeva, et al. "Optimization of Duplex Stability and Terminal Asymmetry for shRNA." (2010).
Nielsen et al., "Mechanism of Eukaryotic RNA polymersase III transcription termination", Science, Jun. 28, 2013, 340(6140):1577-1580.
Qi, et al., "Repurposing CRISPR as an RNA-Guided Platform for Sequence Specific Control of Gene Expression," Cell 152, Feb. 28, 2013, 1173-1183.

* cited by examiner

*Primary Examiner* — Celine X Qian
*Assistant Examiner* — Tiffany Nicole Grooms
(74) *Attorney, Agent, or Firm* — Kilpatrick Townsend & Stockton LLP

(57) ABSTRACT

Methods, compositions, and kits are provided herein for CRISPER/Cas-mediated nucleic acid detection or modification.

15 Claims, 32 Drawing Sheets

Specification includes a Sequence Listing.

sgRNA

5' NNNNNNNNNNNNNNNNNNNNGUUUUAGAGCUAGAAAUAGCAAGUUAAAAUAAGGCUAGUCCGUUAUCAACUUGAAAAAGUGGCACCGAGUCGGUGCUUUUUU 3'

DNA matching region | dCas9 binding hairpin | S. pyogenes terminator

SEQ ID NO:7 sgRNA(F+E)

5' NNNNNNNNNNNNNNNNNNNNGUUUUAGAGCUAGAAAUAGCAAGUUAAAAUAAGGCUAGUCCGUUAUCAACUUGAAAAAGUGGCACCGAGUCGGUGCUUUUUU 3'

Modified nucleotides

SEQ ID NO:8

FIG. 1C

DNA matching region
dCas9 binding hairpin
Modified nucleotides
S. pyogenes terminator

1: original sgRNA design

5' NNNNNNNNNNNNNNNNNNNNguuuuag A GCUA A
                                |||| |
A gccacggugaaaaaaguucaacuauugccugaucggaa uaaaaucaaCGAU
| ||||||
u cggugcuuuuuuu 3'

SEQ ID NO:7

2: Poly-A extension

5' NNNNNNNNNNNNNNNNNNNNguuuuag A GCUA A
                                |||| |
A gccaccgugaaaaaaguucccuucaauauugccaa uaaaaucaaCCGAU
| ||||||
u cggugcuuuuuuaguauaauaaauaaaucaacaaaaucuuuuucucgaguacuagg 3'

SEQ ID NO:10

FIG. 3A dCas9-EGFP

Telomere imaging

1

6

Modified nucleotides
S. pyogenes terminator

DNA matching region
dCas9 binding hairpin

1: Original sgRNA design

SEQ ID NO:7

6: A-U flip (F)

SEQ ID NO:14

*FIG. 4A* dCas9-EGFP

8: Hairpin extension (E)
SEQ ID NO:16

10: Hairpin extension + A-U flip (F+E)
SEQ ID NO:8

| Signal pattern | Observed % of cells with signal patterns |
|---|---|
| 2 Red/2 Green | 9.5% |
| 3 Red/3 Green | 90% |
| 3 Red/2 Green | 0.5% |

FISH analysis of chromosome 3 in HeLa cells

3q28-29/3p26.1

| Signal pattern | Observed % of cells with signal patterns |
| --- | --- |
| 3 Red/3 Green | 97 % |
| 3 Red/2 Green | 3 % |

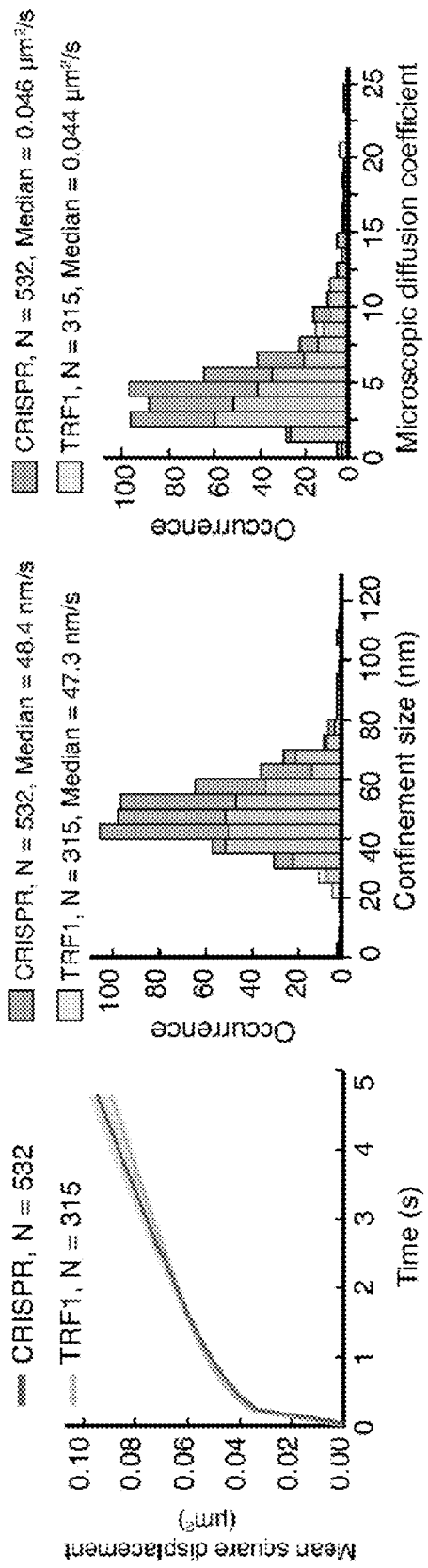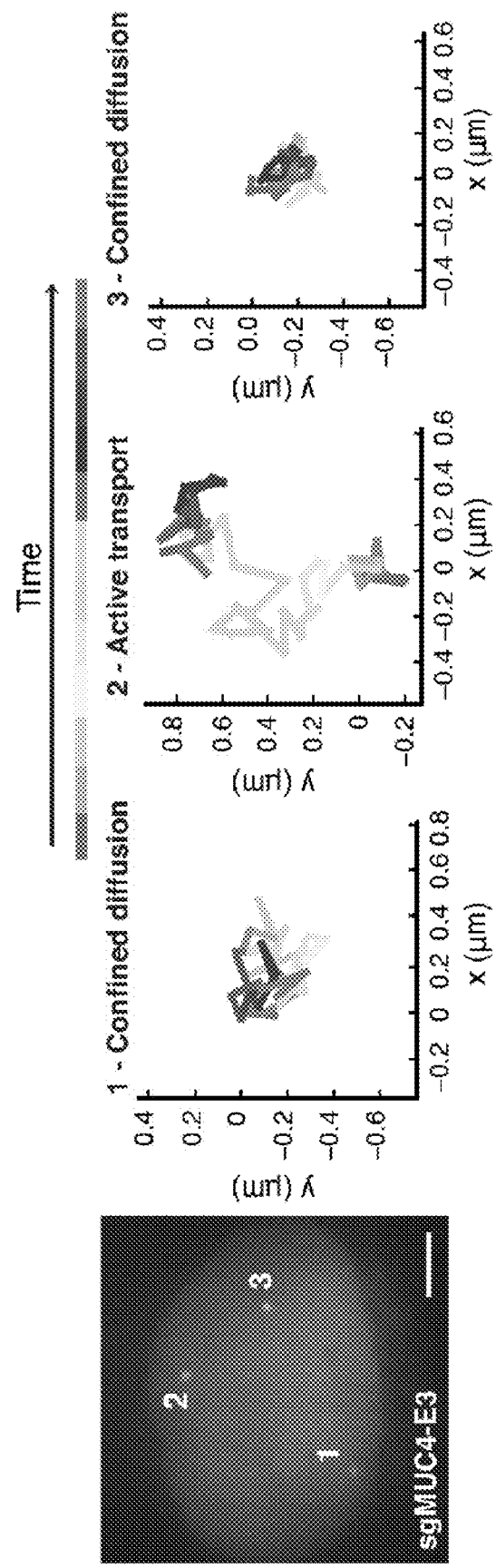
FIG. 14B
FIG. 14C
FIG. 14D
FIG. 14E

SEQUENCE LISTING

```
<160> NUMBER OF SEQ ID NOS: 111

<210> SEQ ID NO 1
<211> LENGTH: 183
<212> TYPE: RNA
<213> ORGANISM: Artificial Sequence
<220> FEATURE:
<223> OTHER INFORMATION: synthetic core optimized small guide RNA
      (sgRNA) reference sequence
<220> FEATURE:
<221> NAME/KEY: modified_base
<222> LOCATION: (1)...(5)
<223> OTHER INFORMATION: n = g, a, c or u
<220> FEATURE:
<221> NAME/KEY: modified_base
<222> LOCATION: (6)...(100)
<223> OTHER INFORMATION: n = g, a, c or u, may be present or absent

<400> SEQUENCE: 1
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn guuuuagagc uagaaauagc     120
aaguuaaaau aaggcuaguc cguuaucaac uugaaaaagu ggcaccgagu cggugcuuuu     180
uuu                                                                   183

<210> SEQ ID NO 2
```

```
<211> LENGTH: 183
<212> TYPE: RNA
<213> ORGANISM: Artificial Sequence
<220> FEATURE:
<223> OTHER INFORMATION: synthetic core optimized small guide RNA
      (sgRNA) reference sequence containing an A-U flip
<220> FEATURE:
<221> NAME/KEY: modified_base
<222> LOCATION: (1)...(5)
<223> OTHER INFORMATION: n = g, a, c or u
<220> FEATURE:
<221> NAME/KEY: modified_base
<222> LOCATION: (6)...(100)
<223> OTHER INFORMATION: n = g, a, c or u, may be present or absent

<400> SEQUENCE: 2
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn guuuaagagc uagaaauagc     120
aaguuuaaau aaggcuaguc cguuaucaac uugaaaaagu ggcaccgagu cggugcuuuu     180
uuu                                                                   183

<210> SEQ ID NO 3
<211> LENGTH: 193
<212> TYPE: RNA
<213> ORGANISM: Artificial Sequence
<220> FEATURE:
<223> OTHER INFORMATION: synthetic core optimized small guide RNA
      (sgRNA) reference sequence with elongated stem portion of 5'
      stem-loop structure
<220> FEATURE:
<221> NAME/KEY: modified_base
<222> LOCATION: (1)...(5)
<223> OTHER INFORMATION: n = g, a, c or u
<220> FEATURE:
<221> NAME/KEY: modified_base
<222> LOCATION: (6)...(100)
<223> OTHER INFORMATION: n = g, a, c or u, may be present or absent

<400> SEQUENCE: 3
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn guuuuagagc uaugcuggaa     120
acagcauagc aaguuaaaau aaggcuaguc cguuaucaac uugaaaaagu ggcaccgagu     180
cggugcuuuu uuu                                                        193

<210> SEQ ID NO 4
<211> LENGTH: 193
<212> TYPE: RNA
<213> ORGANISM: Artificial Sequence
<220> FEATURE:
<223> OTHER INFORMATION: synthetic core optimized small guide RNA
      (sgRNA) reference sequence containing combined A-U flip and
      elongated stem portion of 5' stem-loop structure
<220> FEATURE:
<221> NAME/KEY: modified_base
<222> LOCATION: (1)...(5)
<223> OTHER INFORMATION: n = g, a, c or u
<220> FEATURE:
<221> NAME/KEY: modified_base
<222> LOCATION: (6)...(100)
<223> OTHER INFORMATION: n = g, a, c or u, may be present or absent

<400> SEQUENCE: 4
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn guuuaagagc uaugcuggaa     120
acagcauagc aaguuuaaau aaggcuaguc cguuaucaac uugaaaaagu ggcaccgagu     180
``` cgguugcuuuu uuu                                                                    193

<210> SEQ ID NO 5
<211> LENGTH: 1368
<212> TYPE: PRT
<213> ORGANISM: Artificial Sequence
<220> FEATURE:
<223> OTHER INFORMATION: synthetic Streptococcus pyogenes clustered,
      regularly interspaced short palindromic repeat (CRISPR)-associated
      (Cas) nuclease deficient mutant nicking Cas9 nuclease Cas9D10A

<400> SEQUENCE: 5

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765
```

-continued

```
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
            805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
            885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
            965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala Lys
        1010                1015                1020
Ser Glu Gln Glu Ile Gly Lys Ala Thr Ala Lys Tyr Phe Phe Tyr Ser
1025                1030                1035                1040
Asn Ile Met Asn Phe Phe Lys Thr Glu Ile Thr Leu Ala Asn Gly Glu
                1045                1050                1055
Ile Arg Lys Arg Pro Leu Ile Glu Thr Asn Gly Glu Thr Gly Glu Ile
                1060                1065                1070
Val Trp Asp Lys Gly Arg Asp Phe Ala Thr Val Arg Lys Val Leu Ser
        1075                1080                1085
Met Pro Gln Val Asn Ile Val Lys Lys Thr Glu Val Gln Thr Gly Gly
        1090                1095                1100
Phe Ser Lys Glu Ser Ile Leu Pro Lys Arg Asn Ser Asp Lys Leu Ile
1105                1110                1115                1120
Ala Arg Lys Lys Asp Trp Asp Pro Lys Lys Tyr Gly Gly Phe Asp Ser
            1125                1130                1135
Pro Thr Val Ala Tyr Ser Val Leu Val Val Ala Lys Val Glu Lys Gly
                1140                1145                1150
Lys Ser Lys Lys Leu Lys Ser Val Lys Glu Leu Leu Gly Ile Thr Ile
            1155                1160                1165
Met Glu Arg Ser Ser Phe Glu Lys Asn Pro Ile Asp Phe Leu Glu Ala
        1170                1175                1180
Lys Gly Tyr Lys Glu Val Lys Lys Asp Leu Ile Ile Lys Leu Pro Lys
```

```
                    1185                1190                1195                1200
Tyr Ser Leu Phe Glu Leu Glu Asn Gly Arg Lys Arg Met Leu Ala Ser
                1205                1210                1215

Ala Gly Glu Leu Gln Lys Gly Asn Glu Leu Ala Leu Pro Ser Lys Tyr
                1220                1225                1230

Val Asn Phe Leu Tyr Leu Ala Ser His Tyr Glu Lys Leu Lys Gly Ser
                1235                1240                1245

Pro Glu Asp Asn Glu Gln Lys Gln Leu Phe Val Glu Gln His Lys His
                1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
                1285                1290                1295

His Arg Asp Lys Pro Ile Arg Glu Gln Ala Glu Asn Ile Ile His Leu
                1300                1305                1310

Phe Thr Leu Thr Asn Leu Gly Ala Pro Ala Ala Phe Lys Tyr Phe Asp
                1315                1320                1325

Thr Thr Ile Asp Arg Lys Arg Tyr Thr Ser Thr Lys Glu Val Leu Asp
                1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
                1365

<210> SEQ ID NO 6
<211> LENGTH: 1368
<212> TYPE: PRT
<213> ORGANISM: Artificial Sequence
<220> FEATURE:
<223> OTHER INFORMATION: synthetic Streptococcus pyogenes clustered,
      regularly interspaced short palindromic repeat (CRISPR)-associated
      (Cas) nuclease deficient mutant nicking Cas9 nuclease Cas9H840A

<400> SEQUENCE: 6

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

-continued

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590
```

-continued

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys

```
                    1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                    1045                1050                1055

Ile Arg Lys Arg Pro Leu Ile Glu Thr Asn Gly Glu Thr Gly Glu Ile
                    1060                1065                1070

Val Trp Asp Lys Gly Arg Asp Phe Ala Thr Val Arg Lys Val Leu Ser
                1075                1080                1085

Met Pro Gln Val Asn Ile Val Lys Lys Thr Glu Val Gln Thr Gly Gly
            1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
                1125                1130                1135

Pro Thr Val Ala Tyr Ser Val Leu Val Val Ala Lys Val Glu Lys Gly
                    1140                1145                1150

Lys Ser Lys Lys Leu Lys Ser Val Lys Glu Leu Leu Gly Ile Thr Ile
                1155                1160                1165

Met Glu Arg Ser Ser Phe Glu Lys Asn Pro Ile Asp Phe Leu Glu Ala
            1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
                1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
                1235                1240                1245

Pro Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
                1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
1315                1320                1325

Thr Thr Ile Asp Arg Lys Arg Tyr Thr Ser Thr Lys Glu Val Leu Asp
            1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
                1365

<210> SEQ ID NO 7
<211> LENGTH: 103
<212> TYPE: RNA
<213> ORGANISM: Artificial Sequence
<220> FEATURE:
<223> OTHER INFORMATION: synthetic original small guide RNA (sgRNA)
      design
<220> FEATURE:
<221> NAME/KEY: modified_base
<222> LOCATION: (1)...(20)
```

<223> OTHER INFORMATION: n = g, a, c or u

<400> SEQUENCE: 7
nnnnnnnnnn nnnnnnnnnn guuuuagagc uagaaauagc aaguuaaaau aaggcuaguc    60
cguuaucaac uugaaaaagu ggcaccgagu cggugcuuuu uuu                      103

<210> SEQ ID NO 8
<211> LENGTH: 113
<212> TYPE: RNA
<213> ORGANISM: Artificial Sequence
<220> FEATURE:
<223> OTHER INFORMATION: synthetic optimized small guide RNA (sgRNA-
      (F+E)) design, hairpin extension and A-U flip (F+E)
<220> FEATURE:
<221> NAME/KEY: modified_base
<222> LOCATION: (1)...(20)
<223> OTHER INFORMATION: n = g, a, c or u

<400> SEQUENCE: 8
nnnnnnnnnn nnnnnnnnnn guuuaagagc uaugcuggaa acagcauagc aaguuuaaau    60
aaggcuaguc cguuaucaac uugaaaaagu ggcaccgagu cggugcuuuu uuu           113

<210> SEQ ID NO 9
<211> LENGTH: 48
<212> TYPE: DNA
<213> ORGANISM: Artificial Sequence
<220> FEATURE:
<223> OTHER INFORMATION: synthetic Homo sapiens telomere repeats
      (sgTelomere)

<400> SEQUENCE: 9
ttagggttag ggttagggtt agggttaggg ttagggttag ggttaggg                 48

<210> SEQ ID NO 10
<211> LENGTH: 137
<212> TYPE: RNA
<213> ORGANISM: Artificial Sequence
<220> FEATURE:
<223> OTHER INFORMATION: synthetic optimized small guide RNA (sgRNA)
      modified with polymerase III SINE element polyadenylation signal
      sequence, poly-A extension
<220> FEATURE:
<221> NAME/KEY: modified_base
<222> LOCATION: (1)...(20)
<223> OTHER INFORMATION: n = g, a, c or u

<400> SEQUENCE: 10
nnnnnnnnnn nnnnnnnnnn guuuuagagc uagaaauagc aaguuaaaau aaggcuaguc    60
cguuaucaac uugaaaaagu ggcaccgagu cggugcuaua auaaauaaau caacaaaucu    120
uuuucucgag uacuagg                                                   137

<210> SEQ ID NO 11
<211> LENGTH: 103
<212> TYPE: RNA
<213> ORGANISM: Artificial Sequence
<220> FEATURE:
<223> OTHER INFORMATION: synthetic optimized small guide RNA (sgRNA)
      modified with A-U flip
<220> FEATURE:
<221> NAME/KEY: modified_base
<222> LOCATION: (1)...(20)
<223> OTHER INFORMATION: n = g, a, c or u

<400> SEQUENCE: 11
nnnnnnnnnn nnnnnnnnnn gauuuagagc uagaaauagc aaguuaaauu aaggcuaguc    60
cguuaucaac uugaaaaagu ggcaccgagu cggugcuuuu uuu          103

<210> SEQ ID NO 12
<211> LENGTH: 103
<212> TYPE: RNA
<213> ORGANISM: Artificial Sequence
<220> FEATURE:
<223> OTHER INFORMATION: synthetic optimized small guide RNA (sgRNA)
      modified with A-U flip
<220> FEATURE:
<221> NAME/KEY: modified_base
<222> LOCATION: (1)...(20)
<223> OTHER INFORMATION: n = g, a, c or u

<400> SEQUENCE: 12
nnnnnnnnnn nnnnnnnnnn guauaagagc uagaaauagc aaguuuauau aaggcuaguc    60
cguuaucaac uugaaaaagu ggcaccgagu cggugcuuuu uuu                     103

<210> SEQ ID NO 13
<211> LENGTH: 103
<212> TYPE: RNA
<213> ORGANISM: Artificial Sequence
<220> FEATURE:
<223> OTHER INFORMATION: synthetic optimized small guide RNA (sgRNA)
      modified with A-U flip
<220> FEATURE:
<221> NAME/KEY: modified_base
<222> LOCATION: (1)...(20)
<223> OTHER INFORMATION: n = g, a, c or u

<400> SEQUENCE: 13
nnnnnnnnnn nnnnnnnnnn guuaaagagc uagaaauagc aaguuuuaau aaggcuaguc    60
cguuaucaac uugaaaaagu ggcaccgagu cggugcuuuu uuu                     103

<210> SEQ ID NO 14
<211> LENGTH: 103
<212> TYPE: RNA
<213> ORGANISM: Artificial Sequence
<220> FEATURE:
<223> OTHER INFORMATION: synthetic optimized small guide RNA (sgRNA)
      modified with A-U flip (F)
<220> FEATURE:
<221> NAME/KEY: modified_base
<222> LOCATION: (1)...(20)
<223> OTHER INFORMATION: n = g, a, c or u

<400> SEQUENCE: 14
nnnnnnnnnn nnnnnnnnnn guuuaagagc uagaaauagc aaguuuaaau aaggcuaguc    60
cguuaucaac uugaaaaagu ggcaccgagu cggugcuuuu uuu                     103

<210> SEQ ID NO 15
<211> LENGTH: 116
<212> TYPE: RNA
<213> ORGANISM: Artificial Sequence
<220> FEATURE:
<223> OTHER INFORMATION: synthetic optimized small guide RNA (sgRNA)
      modified with hairpin extension
<220> FEATURE:
<221> NAME/KEY: modified_base
<222> LOCATION: (1)...(20)
<223> OTHER INFORMATION: n = g, a, c or u

<400> SEQUENCE: 15
nnnnnnnnnn nnnnnnnnnn guuuuagagc uaugcuguuu gaaacagcau agcaaguuaa    60
aauaaggcua guccgguuau caacuugaaa aguggcaccg agucggugcu uuuuu        116

```
<210> SEQ ID NO 16
<211> LENGTH: 113
<212> TYPE: RNA
<213> ORGANISM: Artificial Sequence
<220> FEATURE:
<223> OTHER INFORMATION: synthetic optimized small guide RNA (sgRNA)
      modified with hairpin extension (E)
<220> FEATURE:
<221> NAME/KEY: modified_base
<222> LOCATION: (1)...(20)
<223> OTHER INFORMATION: n = g, a, c or u

<400> SEQUENCE: 16
nnnnnnnnnn nnnnnnnnnn guuuuagagc uaugcuggaa acagcauagc aaguuaaaau      60
aaggcuaguc cguuaucaac uugaaaaagu ggcaccgagu cggugcuuuu uuu            113

<210> SEQ ID NO 17
<211> LENGTH: 113
<212> TYPE: RNA
<213> ORGANISM: Artificial Sequence
<220> FEATURE:
<223> OTHER INFORMATION: synthetic optimized small guide RNA (sgRNA)
      modified with combined A-U flip and hairpin extension
<220> FEATURE:
<221> NAME/KEY: modified_base
<222> LOCATION: (1)...(20)
<223> OTHER INFORMATION: n = g, a, c or u

<400> SEQUENCE: 17
nnnnnnnnnn nnnnnnnnnn guuauagagc uaugcuggaa acagcauagc aaguuauaau      60
aaggcuaguc cguuaucaac uugaaaaagu ggcaccgagu cggugcuuuu uuu            113

<210> SEQ ID NO 18
<211> LENGTH: 55
<212> TYPE: DNA
<213> ORGANISM: Artificial Sequence
<220> FEATURE:
<223> OTHER INFORMATION: synthetic Homo sapiens MUC4 exon 2 polymorphic
      exon repeat

<400> SEQUENCE: 18
gccacccctc ttcctgtcac cgacacttcc tcagcatcca caggtcacgc caccc           55

<210> SEQ ID NO 19
<211> LENGTH: 30
<212> TYPE: DNA
<213> ORGANISM: Artificial Sequence
<220> FEATURE:
<223> OTHER INFORMATION: synthetic Homo sapiens MUC4 introon 3
      polymorphic intron repeat

<400> SEQUENCE: 19
gaaggtatgg gtgtggaagg tatgggtgtg                                       30

<210> SEQ ID NO 20
<211> LENGTH: 80
<212> TYPE: DNA
<213> ORGANISM: Artificial Sequence
<220> FEATURE:
<223> OTHER INFORMATION: synthetic Homo sapiens MUC1 exon 3 and intron 3
      polymorphic exon repeat polymorphic exon repeat

<400> SEQUENCE: 20
ggctccaccg cccccccagc ccacggtgtc acctcggccc ggacaccagg ccggccccgg      60
gctccaccgc cccccagcc                                                   80
```

<210> SEQ ID NO 21
<211> LENGTH: 25
<212> TYPE: DNA
<213> ORGANISM: Artificial Sequence
<220> FEATURE:
<223> OTHER INFORMATION: synthetic protospacer sequence for telomere genomic target

<400> SEQUENCE: 21
gttagggtta gggttagggt taggg                                         25

<210> SEQ ID NO 22
<211> LENGTH: 25
<212> TYPE: DNA
<213> ORGANISM: Artificial Sequence
<220> FEATURE:
<223> OTHER INFORMATION: synthetic protospacer sequence for MUC1 genomic target

<400> SEQUENCE: 22
gctccaccgc cccccagcc cacgg                                          25

<210> SEQ ID NO 23
<211> LENGTH: 25
<212> TYPE: DNA
<213> ORGANISM: Artificial Sequence
<220> FEATURE:
<223> OTHER INFORMATION: synthetic protospacer sequence for MUC1 genomic target

<400> SEQUENCE: 23
cccccccagc ccacggtgtc acctc                                         25

<210> SEQ ID NO 24
<211> LENGTH: 26
<212> TYPE: DNA
<213> ORGANISM: Artificial Sequence
<220> FEATURE:
<223> OTHER INFORMATION: synthetic protospacer sequence for MUC1 genomic target

<400> SEQUENCE: 24
cccacggtgt cacctcggcc ccggac                                        26

<210> SEQ ID NO 25
<211> LENGTH: 24
<212> TYPE: DNA
<213> ORGANISM: Artificial Sequence
<220> FEATURE:
<223> OTHER INFORMATION: synthetic protospacer sequence for MUC1 genomic target

<400> SEQUENCE: 25
cccgggctcc accgccccccc cagc                                         24

<210> SEQ ID NO 26
<211> LENGTH: 29
<212> TYPE: DNA
<213> ORGANISM: Artificial Sequence
<220> FEATURE:
<223> OTHER INFORMATION: synthetic protospacer sequence for MUC4_exon genomic target

<400> SEQUENCE: 26
gtcaccgaca cttcctcagc atccacagg                                     29

<210> SEQ ID NO 27

```
<211> LENGTH: 24
<212> TYPE: DNA
<213> ORGANISM: Artificial Sequence
<220> FEATURE:
<223> OTHER INFORMATION: synthetic protospacer sequence for MUC4_exon
      genomic target

<400> SEQUENCE: 27
ccctcttcct gtcaccgaca cttc                                          24

<210> SEQ ID NO 28
<211> LENGTH: 25
<212> TYPE: DNA
<213> ORGANISM: Artificial Sequence
<220> FEATURE:
<223> OTHER INFORMATION: synthetic protospacer sequence for MUC4_exon
      genomic target

<400> SEQUENCE: 28
cctcagcatc cacaggtcac gccac                                         25

<210> SEQ ID NO 29
<211> LENGTH: 26
<212> TYPE: DNA
<213> ORGANISM: Artificial Sequence
<220> FEATURE:
<223> OTHER INFORMATION: synthetic protospacer sequence for MUC4_intron
      genomic target

<400> SEQUENCE: 29
gaaggtatgg gtgtggaagg tatggg                                        26

<210> SEQ ID NO 30
<211> LENGTH: 16
<212> TYPE: DNA
<213> ORGANISM: Artificial Sequence
<220> FEATURE:
<223> OTHER INFORMATION: synthetic protospacer sequence for MUC4_intron
      genomic target

<400> SEQUENCE: 30
gtgtggaagg tatggg                                                   16

<210> SEQ ID NO 31
<211> LENGTH: 24
<212> TYPE: DNA
<213> ORGANISM: Artificial Sequence
<220> FEATURE:
<223> OTHER INFORMATION: synthetic oligo fluorescence in situ
      hybridization (FISH) probe for telomere genomic target
<220> FEATURE:
<221> NAME/KEY: modified_base
<222> LOCATION: (1)...(1)
<223> OTHER INFORMATION: t modified by 5' Cy3

<400> SEQUENCE: 31
ttagggttag ggttagggtt aggg                                          24

<210> SEQ ID NO 32
<211> LENGTH: 24
<212> TYPE: DNA
<213> ORGANISM: Artificial Sequence
<220> FEATURE:
<223> OTHER INFORMATION: synthetic oligo fluorescence in situ
      hybridization (FISH) probe for telomere genomic target
<220> FEATURE:
<221> NAME/KEY: modified_base
<222> LOCATION: (1)...(1)
<223> OTHER INFORMATION: t modified by 5' Cy5
```

<400> SEQUENCE: 32
ttagggttag ggttagggtt aggg                                          24

<210> SEQ ID NO 33
<211> LENGTH: 20
<212> TYPE: DNA
<213> ORGANISM: Artificial Sequence
<220> FEATURE:
<223> OTHER INFORMATION: synthetic oligo fluorescence in situ
      hybridization (FISH) probe for MUC1 genomic target
<220> FEATURE:
<221> NAME/KEY: modified_base
<222> LOCATION: (1)...(1)
<223> OTHER INFORMATION: a modified by 5' Cy3

<400> SEQUENCE: 33
agcccacggt gtcacctcgg                                               20

<210> SEQ ID NO 34
<211> LENGTH: 16
<212> TYPE: DNA
<213> ORGANISM: Artificial Sequence
<220> FEATURE:
<223> OTHER INFORMATION: synthetic oligo fluorescence in situ
      hybridization (FISH) probe for MUC1 genomic target
<220> FEATURE:
<221> NAME/KEY: modified_base
<222> LOCATION: (1)...(1)
<223> OTHER INFORMATION: a modified by 5' Cy5

<400> SEQUENCE: 34
acctcggccc cggaca                                                   16

<210> SEQ ID NO 35
<211> LENGTH: 20
<212> TYPE: DNA
<213> ORGANISM: Artificial Sequence
<220> FEATURE:
<223> OTHER INFORMATION: synthetic oligo fluorescence in situ
      hybridization (FISH) probe for MUC4_exon genomic target
<220> FEATURE:
<221> NAME/KEY: modified_base
<222> LOCATION: (1)...(1)
<223> OTHER INFORMATION: t modified by 5' Cy3

<400> SEQUENCE: 35
tcttcctgtc accgacactt                                               20

<210> SEQ ID NO 36
<211> LENGTH: 15
<212> TYPE: DNA
<213> ORGANISM: Artificial Sequence
<220> FEATURE:
<223> OTHER INFORMATION: synthetic oligo fluorescence in situ
      hybridization (FISH) probe for MUC4_exon genomic target
<220> FEATURE:
<221> NAME/KEY: modified_base
<222> LOCATION: (1)...(1)
<223> OTHER INFORMATION: c modified by 5' Cy5

<400> SEQUENCE: 36
cttcctgtca ccgac                                                    15

<210> SEQ ID NO 37
<211> LENGTH: 15
<212> TYPE: DNA
<213> ORGANISM: Artificial Sequence
<220> FEATURE:

```
<223> OTHER INFORMATION: synthetic oligo fluorescence in situ
      hybridization (FISH) probe for MUC4_intron genomic target
<220> FEATURE:
<221> NAME/KEY: modified_base
<222> LOCATION: (1)...(1)
<223> OTHER INFORMATION: a modified by 5' Cy3

<400> SEQUENCE: 37
aggtatgggt gtgga                                                      15

<210> SEQ ID NO 38
<211> LENGTH: 15
<212> TYPE: DNA
<213> ORGANISM: Artificial Sequence
<220> FEATURE:
<223> OTHER INFORMATION: synthetic oligo fluorescence in situ
      hybridization (FISH) probe for MUC4_intron genomic target
<220> FEATURE:
<221> NAME/KEY: modified_base
<222> LOCATION: (1)...(1)
<223> OTHER INFORMATION: a modified by 5' Cy5

<400> SEQUENCE: 38
aggtatgggt gtgga                                                      15

<210> SEQ ID NO 39
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 39
gaagagtgga ggccgtgcgc ggtgg                                           25

<210> SEQ ID NO 40
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 40
aggcaggaga tcacctgagg tcagg                                           25

<210> SEQ ID NO 41
<211> LENGTH: 21
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 41
ccccgtctct actaaatata c                                               21

<210> SEQ ID NO 42
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 42
ccccacctgt aattccagct actc                                            24
```

```
<210> SEQ ID NO 43
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 43
cctgggaggt ggaggttgca gtgagc                                          26

<210> SEQ ID NO 44
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 44
cctgggagag agagcgagac tctgtc                                          26

<210> SEQ ID NO 45
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 45
gaagaggaga aaagtgggga agagg                                           25

<210> SEQ ID NO 46
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 46
gaacagaggg ccagagagca gcccgg                                          26

<210> SEQ ID NO 47
<211> LENGTH: 27
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 47
cccaggctta ctcgcagaga gaaagac                                         27

<210> SEQ ID NO 48
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 48
gtacaccctt gtgtacagag ctggg                                           25
```

```
<210> SEQ ID NO 49
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 49
gaaaactcat gtaaagctgc aggg                                          24

<210> SEQ ID NO 50
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 50
gcaagcaagg gaagcgacaa ggagg                                         25

<210> SEQ ID NO 51
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 51
ggaggcggcc agggcgcaga ggg                                           23

<210> SEQ ID NO 52
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 52
cctctgagct cgggtttaaa agc                                           23

<210> SEQ ID NO 53
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 53
gtagccccgg cattggcctt ggg                                           23

<210> SEQ ID NO 54
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 54
gcctgtggga gatgttccct cggg                                          24
```

```
<210> SEQ ID NO 55
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 55
ccaggctgtc cctctggctt caggac                                          26

<210> SEQ ID NO 56
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 56
gagtctttgg gggagagtct ggg                                             23

<210> SEQ ID NO 57
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 57
gctcctgccc tgcctctcag cagg                                            24

<210> SEQ ID NO 58
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 58
gcatatttga ggagcttcct ggg                                             23

<210> SEQ ID NO 59
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 59
ggctgcaaga gaagccatgc tgg                                             23

<210> SEQ ID NO 60
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 60
gatgtttcag gactaggctg aggg                                            24

<210> SEQ ID NO 61
```

```
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 61
ccctacacct ccccaccctc cagc                                           24

<210> SEQ ID NO 62
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 62
cccgctccag tgctcatccc acc                                            23

<210> SEQ ID NO 63
<211> LENGTH: 22
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 63
gccctgcaga tgtggttgaa gg                                             22

<210> SEQ ID NO 64
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 64
gaggctgggg cttgggcgc cggg                                            24

<210> SEQ ID NO 65
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 65
gtctttgccg tgaactgttc tgg                                            23

<210> SEQ ID NO 66
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 66
cccgtgtctc cccagggccc cggtc                                          25

<210> SEQ ID NO 67
<211> LENGTH: 23
```

```
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 67
gctggacact cagctccatg tgg                                              23

<210> SEQ ID NO 68
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 68
gagcgcagag gggcaagacc tggg                                             24

<210> SEQ ID NO 69
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 69
gagaaggagt gaaggactgt tgg                                              23

<210> SEQ ID NO 70
<211> LENGTH: 28
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 70
cccgaagaag ctaggcatgt cgtggagc                                         28

<210> SEQ ID NO 71
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 71
gagctgggcc aggagaggag atgg                                             24

<210> SEQ ID NO 72
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 72
gaccgggcat gaccagggcc ttgg                                             24

<210> SEQ ID NO 73
<211> LENGTH: 23
<212> TYPE: DNA
```

<213> ORGANISM: Artificial Sequence
<220> FEATURE:
<223> OTHER INFORMATION: synthetic protospacer sequence for MUC4
    non-repetitive region

<400> SEQUENCE: 73
gggcagcccc cacccccaca ggg                                              23

<210> SEQ ID NO 74
<211> LENGTH: 24
<212> TYPE: DNA
<213> ORGANISM: Artificial Sequence
<220> FEATURE:
<223> OTHER INFORMATION: synthetic protospacer sequence for MUC4
    non-repetitive region

<400> SEQUENCE: 74
gttccttttg gctccctgaa gggg                                             24

<210> SEQ ID NO 75
<211> LENGTH: 23
<212> TYPE: DNA
<213> ORGANISM: Artificial Sequence
<220> FEATURE:
<223> OTHER INFORMATION: synthetic protospacer sequence for MUC4
    non-repetitive region

<400> SEQUENCE: 75
gggtctgttt gcacacttgc cgg                                              23

<210> SEQ ID NO 76
<211> LENGTH: 26
<212> TYPE: DNA
<213> ORGANISM: Artificial Sequence
<220> FEATURE:
<223> OTHER INFORMATION: synthetic protospacer sequence for MUC4
    non-repetitive region

<400> SEQUENCE: 76
gcccaggcca gaggaaaaac acaggg                                           26

<210> SEQ ID NO 77
<211> LENGTH: 23
<212> TYPE: DNA
<213> ORGANISM: Artificial Sequence
<220> FEATURE:
<223> OTHER INFORMATION: synthetic protospacer sequence for MUC4
    non-repetitive region

<400> SEQUENCE: 77
gtttccttaa ggaacagccc tgg                                              23

<210> SEQ ID NO 78
<211> LENGTH: 25
<212> TYPE: DNA
<213> ORGANISM: Artificial Sequence
<220> FEATURE:
<223> OTHER INFORMATION: synthetic protospacer sequence for MUC4
    non-repetitive region

<400> SEQUENCE: 78
gcagacagag gtgggctaga caagg                                            25

<210> SEQ ID NO 79
<211> LENGTH: 26
<212> TYPE: DNA
<213> ORGANISM: Artificial Sequence

```
<220> FEATURE:
<223> OTHER INFORMATION: synthetic protospacer sequence for MUC4
      non-repetitive region

<400> SEQUENCE: 79
gccccaggca ggaatgactc agaagg                                            26

<210> SEQ ID NO 80
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 80
ccacagggaa aggcaactgg gtc                                               23

<210> SEQ ID NO 81
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 81
gaccccaggg aggtgacagg ctgg                                              24

<210> SEQ ID NO 82
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 82
gccacagcgc actccacggg gaaggg                                            26

<210> SEQ ID NO 83
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 83
ggtctatctg tcagtctggg acagg                                             25

<210> SEQ ID NO 84
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 84
ccaaaactct ccacagaccc ctc                                               23

<210> SEQ ID NO 85
<211> LENGTH: 24
<212> TYPE: DNA
<213> ORGANISM: Artificial Sequence
<220> FEATURE:
```

<223> OTHER INFORMATION: synthetic protospacer sequence for MUC4
      non-repetitive region

<400> SEQUENCE: 85
gtccagcatc agcgacgccc ttgg                                          24

<210> SEQ ID NO 86
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 86
ccttttggct ctggagtctt aggc                                          24

<210> SEQ ID NO 87
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 87
gctactacgt agggttgtca tgagg                                         25

<210> SEQ ID NO 88
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 88
gtaaagtaga aaaggcataa aggg                                          24

<210> SEQ ID NO 89
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 89
cccagcactt ttggaggccc aggc                                          24

<210> SEQ ID NO 90
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 90
ccagcttggc caaccctgtc tccac                                         25

<210> SEQ ID NO 91
<211> LENGTH: 26
<212> TYPE: DNA
<213> ORGANISM: Artificial Sequence
<220> FEATURE:
<223> OTHER INFORMATION: synthetic protospacer sequence for MUC4 non-repetitive region

<400> SEQUENCE: 91
cctgggaggc agaggttgca gggagc                                              26

<210> SEQ ID NO 92
<211> LENGTH: 27
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 92
ccataaagac gtgtttgaga aagaggc                                             27

<210> SEQ ID NO 93
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 93
gaacccggaa tggcacttgt gtcgg                                               25

<210> SEQ ID NO 94
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 94
cctcgtgcct ctaaaaagcc acc                                                 23

<210> SEQ ID NO 95
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 95
ggcttggtgt attcagaatg tgg                                                 23

<210> SEQ ID NO 96
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 96
cctggcagag gctggcctgg cagtgc                                              26

<210> SEQ ID NO 97
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 97
gctaaggaca agaggcaatg agagg    25

<210> SEQ ID NO 98
<211> LENGTH: 27
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 98
ccccagcatg ttctgagaaa ttgagtc    27

<210> SEQ ID NO 99
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 99
gacagagttt ctctctgtcc cccagg    26

<210> SEQ ID NO 100
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 100
ggggtttcac catgttggcc agg    23

<210> SEQ ID NO 101
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 101
gctcgcctcg gctcccaaag tgctgg    26

<210> SEQ ID NO 102
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 102
gggcatttgt gttgcacgtg agg    23

<210> SEQ ID NO 103
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

```
<400> SEQUENCE: 103
cctgggttgc ccgcagctcc actc                                           24

<210> SEQ ID NO 104
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 104
gtagagatgc cgccccgccc agg                                            23

<210> SEQ ID NO 105
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 105
gtccagtggc cagtggattt tgggg                                          25

<210> SEQ ID NO 106
<211> LENGTH: 25
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 106
gaggcagctg ggactagaac ccagg                                          25

<210> SEQ ID NO 107
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 107
ccaaaccagc ccagcccacc gac                                            23

<210> SEQ ID NO 108
<211> LENGTH: 24
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 108
ccctgctgag acagccattc attc                                           24

<210> SEQ ID NO 109
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 109
```

```
gaaacagacg tggcccagtc tcttgg                                    26

<210> SEQ ID NO 110
<211> LENGTH: 23
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 110
gctgagagct gcatttcgaa tgg                                       23

<210> SEQ ID NO 111
<211> LENGTH: 26
<212> TYPE: DNA
<213> ORGANISM: Artificial Sequence
<220> FEATURE:
<223> OTHER INFORMATION: synthetic protospacer sequence for MUC4
      non-repetitive region

<400> SEQUENCE: 111
gacaagtcag gaagggccct gtgagg                                    26
```

OPTIMIZED SMALL GUIDE RNAS AND METHODS OF USE

CROSS-REFERENCE TO RELATED APPLICATION

This application is a divisional of U.S. patent application Ser. No. 15/025,217, filed Mar. 25, 2016, which is a 371 national phase application of PCT/US14/58133, filed Sep. 29, 2014, which claims priority to U.S. Provisional Application No. 61/883,929, filed on Sep. 27, 2013, the contents of which are hereby incorporated in their entirety for all purposes.

STATEMENT AS TO RIGHTS TO INVENTIONS MADE UNDER FEDERALLY SPONSORED RESEARCH AND DEVELOPMENT

This invention was made with government support under Grant No. GM081879 awarded by the National Institutes of Health. The government has certain rights in the invention.

REFERENCE TO SUBMISSION OF A SEQUENCE LISTING

The Sequence Listing written in file sequence-listing-1006042.txt created on Mar. 22, 2016, 51,983 bytes, machine format IBM-PC, MS-Windows operating system, is hereby incorporated by reference in its entirety for all purposes.

BACKGROUND OF THE INVENTION

Clustered, regularly interspaced short palindromic repeat (CRISPR) sequences are present in approximately 40% of eubacterial genomes and nearly all archaeal genomes sequenced to date, and consist of short C24-48 nucleotide) direct repeats separated by similarly sized, unique spacers. They are generally flanked by a set of CRISPR-associated (Cas) genes that encode a nuclease this is important for CRISPR maintenance and function. In *Streptococcus thermophilus* and *Escherichia coli*, CRISPR/Cas loci have been demonstrated to confer immunity against bacteriophage infection by an interference mechanism that relies on the strict identity between CRISPR spacers and phage target sequences. The mechanism underlying this immunity is based on sequence specific cleavage of foreign nucleic acids by a CRISPR:Cas complex that contains the Cas nuclease and a guide RNA derived from the CRISPR sequences that provides target sequence specificity through a single stranded binding region. Binding of the CRISPR:Cas complex to the target sequence results in double stranded cleavage of the target sequence.

The CRISPR/Cas system has been modified for use in prokaryotic and eukaryotic systems for genome editing and transcriptional regulation. However, methods and compositions known the in art often fail to provide the activity and specificity necessary for routine use. For example, Cradick, et al., Nucleic Acids Res. Aug. 11, 2013; Pattanayak, et al., Nat Biotechnol. 2013 September;31(9):839-43; Mali, et al., Nat Biotechnol. 2013 Sep;31(9):833-8; and Hsu, et al., Nat Biotechnol. 2013 September;31(9):827-32, all report significant off-target genome editing and varied editing efficiency across different gene targets. Similar issues also exist when using known CRISPR/Cas systems for regulation of transcription.

BRIEF SUMMARY OF THE INVENTION

In one embodiment, this invention provides a small guide RNA molecule comprising from 5' to 3': a binding region, comprising between about 5 and about 50 nucleotides; a 5' hairpin region, comprising: fewer than four consecutive uracil nucleotides; or a length of at least 31 nucleotides; and a 3' hairpin region; and a transcription termination sequence, wherein the small guide RNA is configured to form a complex with a small guide RNA-mediated nuclease, the complex having increased stability or activity relative to a complex containing a small guide RNA-mediated nuclease and a small guide RNA comprising at least 95% identity to SEQ ID NO:1 or a complement thereof In some cases, the 5' hairpin region of the small guide RNA molecule comprises fewer than four consecutive uracil nucleotides and a length of at least 31 nucleotides, a length of at least 35 nucleotides, or a length of at least 36, 37, 38, 39, 40, 41, 42, 43, 44, 45, 46, 47, 48, 49, or 50 nucleotides. In some cases, the small guide RNA molecule further comprises an additional hairpin region designed to interact with a protein or small-molecule to conditionally stabilize the secondary and/or tertiary structure of the small guide RNA molecule. In some cases, the small guide RNA molecule comprises at least 95% identity to SEQ ID NOs:2, 3, or 4, or a complement thereof In some embodiments, the invention provides a composition for nucleic acid modification or detection comprising any of the foregoing small guide RNA molecules. In some cases, the composition further comprises a small guide RNA-mediated nuclease, wherein the small guide RNA and the small guide RNA-mediated nuclease form a complex having increased stability or activity relative to a complex containing a small guide RNA comprising at least 95% identity to SEQ ID NO:1 or a complement thereof. In some cases, the composition is nuclease defective, thereby forming a complex configured to bind to, but not cleave or nick, a target nucleic acid substantially complementary to the binding region of the small guide RNA. In some cases, the nuclease defective composition comprises a Cas9 protein containing a mutation at one or more of the following residues: D10, G12, G17, E762, H840, N854, N863, H982, H983, A984, D986, or A987. In some cases, the nuclease defective composition comprises a Cas9 protein containing a mutation at two or more of the following residues: D10, G12, G17, E762, H840, N854, N863, H982, H983, A984, D986, and A987. In some cases, the nuclease defective composition comprises a Cas9 protein containing a D10A and a H840A mutation.

In some cases, the nuclease defective composition comprises a labeled Cas9 protein. For example, in some cases, the labeled Cas9 protein comprises a fluorophore. In some cases, the fluorophore is a fluorescent protein.

In some cases, the nuclease defective composition comprises a Cas9 protein that comprises a polypeptide that modulates (e.g., activates or represses) transcription. For example, the Cas9 protein can be a Cas9 fused to a transcriptional repressor, including but not limited to, a chromoshadow domain (CSD). As another example, the Cas9 protein can be a Cas9 fused to a transcriptional repressor, including but not limited to, a Krüppel associated box (KRAB) domain. As yet another example, the Cas9 protein can be a Cas9 fused to a transcriptional activator, including but not limited to, VP8, VP16, or VP64.

In some embodiments, the composition has nuclease activity, thereby forming a complex configured to bind and cleave a target nucleic acid sequence substantially complementary to the binding region of the small guide RNA. In some cases, the small guide RNA-mediated nuclease has nicking activity, but is substantially defective at catalyzing double stranded breaks in the target sequence. In some cases, the small guide RNA-mediated nuclease comprises a Cas9 protein containing a mutation at one or more of the following residues D10, G12, G17, E762, H840, N854, N863, H982, H983, A984, D986, or A987. In some cases, the small guide RNA-mediated nuclease comprises a Cas9 protein with nicking activity containing a mutation at one or more of the following residues D10, G12, G17, E762, H840, N854, N863, H982, H983, A984, D986, or A987.

In some embodiments, the invention provides an expression cassette comprising a promoter operably linked to a nucleic acid encoding any of the small guide RNAs of claims 1-3. In some cases, the promoter of the expression cassette is an RNA polymerase III promoter. In some cases, the RNA polymerase promoter is a U6 or H1 promoter, preferably a U6 promoter. In some cases, the promoter of the expression cassette is an SFFV promoter.

In some embodiments, the invention provides an expression cassette comprising a promoter operably linked to a nucleic acid encoding a small guide RNA-mediated nuclease. In some cases, the promoter is a weak mammalian promoter as compared to the human elongation factor 1 promoter (EF1A). In some cases, the weak mammalian promoter is a ubiquitin C promoter or a phosphoglycerate kinase 1 promoter (PGK). In some cases, the weak mammalian promoter is a TetOn promoter in the absence of an inducer. In some cases, the nucleic acid encoding a small guide RNA-mediated nuclease of the expression cassette further encodes a one or two nuclear localization sequences.

In some embodiments, the present invention provides a host cell comprising any one of the foregoing small guide RNAs. In some cases, the cell further comprises a small guide RNA-mediated nuclease. In some cases, the small guide RNA-mediated nuclease is labeled, such as with a fluorophore, such as a fluorescent protein.

In some embodiments, the present invention provides a method of detecting a target nucleic acid sequence in a cell, the method comprising: (i) introducing into the cell: (a) one or more small guide RNAs, each small guide RNA specific for the target nucleic acid sequence; and (b) a labeled nuclease-deficient small guide RNA-mediated nuclease, thereby forming a labeled RNA:nuclease complex; and (ii) incubating the cell to allow the labeled RNA:nuclease complex to localize to the target nucleic acid sequence; and (iii) detecting the presence, absence, or quantity of labeled complex in the nucleus of the cell, thereby detecting the target nucleic acid.

In some cases, the method further comprises introducing at least 2, 3, 4, 5, 6, 7, 8, 10, 15, 20 (e.g., 3-20, 4-10, etc.) or more different small guide RNAs, each specific for a different portion of the target nucleic acid sequence. In some cases, the one or more small guide RNAs are specific for a repeated target sequence. In some cases, the repeated target sequence comprises at least 5, 10, 15, 20 or more contiguous repeats, each repeat of at least 5, 10, 15, 20, or more nucleotides in length. In some cases, the small guide RNA-mediated nuclease contains a mutation at one or more of the following residues D10, G12, G17, E762, H840, N854, N863, H982, H983, A984, D986, or A987. In some cases, the small guide RNA-mediated nuclease contains a mutation at two or more of the following residues D10, G12, G17, E762, H840, N854, N863, H982, H983, A984, D986, or A987.

In some embodiments, the introducing further comprises: forming a complex between:—a first labeled nuclease-deficient small guide RNA-mediated nuclease and one or more small guide RNAs, to form a first labeled complex; and—a second labeled nuclease deficient small guide RNA-mediated nuclease and one or more small guide RNAs, to form a second labeled complex; and contacting the cell with the first and second complexes. In some cases, the method further comprises forming a third and fourth labeled complex and contacting the cell with the four labeled complexes. In some cases, each labeled complex is specific for a different target nucleic acid sequence or specific for a different region of a chromosome. In some cases, each labeled complex is labeled with a different label, and the method comprises detecting the presence, absence, or quantity of each labeled complex in the nucleus of the cell.

In some embodiments, the present invention provides a method of modifying a target nucleic acid sequence in a cell, the method comprising: (i) introducing into the cell: (a) any of the foregoing small guide RNAs, the small guide RNA specific for the target nucleic acid sequence; and (b) a small guide RNA-mediated nuclease, thereby forming a small guide RNA:nuclease complex; and (ii) incubating the cell to allow the small guide RNA:nuclease complex to bind to and cleave or nick the target nucleic acid, thereby modifying the target nucleic acid sequence in the cell.

In some cases, the small guide RNA-mediated nuclease is capable of catalyzing double stranded breaks in the target nucleic acid, and the method further comprises cleaving the target nucleic acid. In some cases, the small guide RNA-mediated nuclease is capable of nicking the target nucleic acid but not catalyzing double stranded breaks in the target nucleic acid, and the method further comprises nicking the target nucleic acid. In some cases, the method further comprises (i) introducing into the cell: (a) a pair of any of the foregoing small guide RNAs, each small guide RNA specific for a target nucleic acid, wherein the pair of small guide RNAs bind to target nucleic acids on a chromosome and flank a nucleic acid region of interest; and (b) a small guide RNA-mediated nuclease, thereby forming a pair of small guide RNA:nuclease complexes; and (ii) incubating the cell to allow the small guide RNA:nuclease complexes to localize to the target nucleic acid sequence, thereby creating nicks or double stranded breaks that flank the nucleic acid region of interest; and (iii) incubating the cell to allow non-homologous end joining (NHEJ) or homologous DNA repair (HDR) to occur, thereby reducing heterozygosity in the cell or deleting at least a portion of the nucleic acid region of interest. In some cases, the method the method further comprises introducing into the cell a heterologous nucleic acid that contains regions of substantial homology to the nucleic acid region of interest, thereby incorporating at least a portion of the heterologous nucleic acid into the nucleic acid region of interest.

In some embodiments, the present invention provides a kit comprising an sgRNA and a labeled nuclease defective sgRNA-mediated nuclease. In some cases, the kit further comprises a second sgRNA or a second labeled nuclease defective sgRNA-mediated nuclease. In some cases, the kit further comprises a cell transfection reagent.

BRIEF DESCRIPTION OF THE DRAWINGS

FIG. 1A-1E depict an optimized CRISPR system for visualizing sequence-specific genomic elements in living human cells. (FIG. 1A) Overview of using CRISPR for genome imaging. A dCas9-EGFP fusion protein and sgR- NAs allow local enrichment of fluorescence signals at specific genomic sites in living cells. (FIG. 1B) The CRISPR imaging system consists of a doxycycline-inducible expression system with low dCas9-EGFP expression level, a Tet-on 3G trans-activator, and custom designed sgRNAs expressed from a murine U6 promoter. We also optimized the nuclear localization of the dCas9-EGFP fusion protein by modifying the fusion strategy with nuclear localization signals (NLS). (FIG. 1C) Original and optimized sgRNA designs. The optimized sgRNA contains an A-U pair flip (underlined) and 5-bp extension (underlined) at the top of the hairpin (boxed). (FIG. 1D) CRISPR imaging of the human telomeric DNA sequence in RPE cells. The sgRNA target site is indicated by a gray line and the adjacent PAM is shown. The optimized sgRNA (FIG. 1E-1F) show a much higher labeling efficiency with lower background fluorescence signals. SgGAL4 is the negative control without cognate binding sites in the genome. Scale bar, 5 µm. (FIG. 1E) Histograms of telomere counts and distribution of telomere fluorescence intensity. The optimized sgRNA shows greatly enhanced labeling efficiency of telomeres.

FIG. 3A-3D depicts a comparison of different sgRNA designs for CRISPR-mediated gene repression. Different sgRNAs were transiently transfected into a GFP+HEK293 reporter cell line harboring a genomic integrated dCas9-KRAB gene. The fluorescence was assayed using flow cytometry. Modifications (underlined) of sgRNA sequence with a polymerase III SINE element polyadenylation signal sequence (#2), A-U flip (#3, 4, 5 and 6), hairpin extension (#7 and 8) and combined changes were hypothesized to increase sgRNA expression level, stability or its association with dCas9 protein. Repression fold is calculated by dividing the fluorescence of +sgGAL4 and fluorescence+different designs. The fold increase in repression is calculated by dividing the fluorescence of Design #1 and fluorescence of other designs. The unmodified hairpin nucleotides are boxed.

FIG. 4A-4C Optimized sgRNA designs enhance the labeling efficiency of telomeres. (FIGS. 4A and 4B) Both designs of A-U flip (#6) and hairpin extension (#8) increased the telomere labeling efficiency compared to the original sgRNA design (#1), as more dCas9-EGFP puncta were observed. Combining both modifications of A-U flip and hairpin extension (#10) further enhanced the labeling efficiency and reduced background fluorescence signal. This design was used for later imaging and annotated as (F+E). Each conventional fluorescence image shows one projected three dimensional (3-D) stack of 3 µm deep (an entire RPE nucleus) with 0.4 µm focal spacing. Scale bar, 5 µm. (FIG. 4C) A plot of overall telomere intensity distribution comparing the telomere labeling efficiencies of different sgRNA designs. Each spot stands for one cell. The percentage of whole-cell GFP is calculated as the ratio of overall telomere intensity and overall GFP signal in the whole cell.

(FIG. 6A) Co-localization of dCas9-EGFP and telomeres as labeled by Oligo FISH (top) or antibody to TRF2 (bottom). (FIG. 6B-6C)Telomere elongation was induced in UMUC3 cancer cells (starting telomere length 2-5 kb) by overexpression of human telomerase RNA (hTR). (FIG. 6B) Visualization of telomeres in UMUC3 cells by CRISPR labeling. (FIG. 6C) Telomere fluorescence intensity in CRISPR-labeled cells increases after elongation of telomeres by hTR. Scale bar, 5 µm.

(FIG. 7A) Co-localization of PNA FISH and 53BP1 staining in RPE cells, dCas9-EGFP-labeled RPE cells, and TIN2 shRNA-treated RPE cells. TIN2 shRNA infecting the RPE cells was used to induce telomeric DNA damage response revealed by 53BP1 antibody staining. 53BP1 signal was enriched at the telomeres indicated by PNA probe in most cells when infected with TIN2 shRNA. There was no obvious enrichment of 53BP1 at the telomeres labeled by PNA probes or dCas9-EGFP. (FIG. 7B) Histogram showing the quantification of 53BP1 signal enriched at the telomeres.

FIG. 8A-811 depict the results of imaging of endogenous MUC4 gene by targeting the repetitive or non-repetitive regions via dCas9-EGFP. (FIG. 8A) Schematic of the human MUC4 locus containing two repeated regions in exon 2 and intron 3 as indicated. The sgRNA target sites are indicated by gray lines and the adjacent PAMs are shown.

(FIG. 10A) In addition to RPE and UMUC3 cell lines, CRISPR can also detect MUC4 loci and telomeres in living HeLa cells. Three MUC4 loci (arrows) were detected by CRISPR via targeting the repetitive exon region. (FIG. 10B) Histograms of MUC4 loci counts by CRISPR labeling. (FIG. 10C) MUC4 locus is localized at 3q29 of chromosome 3. Two hundred interphase nuclei of HeLa cells were examined by FISH using two probes hybridized to 3q26.1 and 3q28-29, respectively. All two hundred cells demonstrated a FISH signal pattern of three copies of 3q28-29, suggesting trisomy chromosome 3 in HeLa cells.

(FIG. 11A) Schematic depicting the structure of MUC1 gene, which contains a 60 bp unit repeated 20 to 140 copies in both exon 3 and intron 3. Four sgRNAs were designed to target the repeat region, and their target sites are indicated with gray lines and the adjacent PAM are also indicated. (FIG. 11B) MUC1 loci (arrows) visualized in RPE cells by targeting four different protospacers. (FIG. 11C) The labeling specificity of CRISPR was confirmed by oligo FISH labeling. The co-localization of dCas9-EGFP and oligo FISH is indicated by an arrow. (FIG. 11D) Histograms of the labeling efficiency of MUC1 loci by targeting different protospacers. 1-5 spots can be observed in 90% of the cells with sgMUC1-E1 and 95% of cells with sgMUC1-E3, but only in 45% and 20% of cells with sgMUC1-E2 and sgMUC1-E4, respectively. The sgRNA design (sgMUC1-E4(F+E)) increased the labeling efficiency compared to sgMUC1-E4 from 20% to 55%.

(FIG. 12A) Oligo FISH labeling of MUC4 exon, MUC4 intron, and MUC1 exon as indicated by arrows. (FIG. 12B) Histograms showing the statistics of observed spots for labeling MUC4 exon, MUC4 intron, and MUC1 exon by Oligo FISH or CRISPR. CRISPR shows a higher labeling efficiency in all cases.

(FIG. 13A) The loci of MUC1 and MUC4 were co-labeled by infecting RPE cells with both sgMUC1-E1 and sgMUC4-E3. More spots (arrows) were observed compared to individual sgMUC1-E1 or sgMUC4-E3 labeling, while similar number of spots was detected if infecting the cells with both sgMUC4-E3 and sgMUC4-I2(F+E) that target the same MUC4 (FIG. 13B) Histograms showing the counts of Mucin genes loci. 45% of cells targeting both MUC1 and MUC4 contain more than 6 spots, while only 10% of cells have 6 spots with co-infection of two sgMUC4s.

FIG. 14A-14H depict single particle tracking and diffusion dynamics of MUC4 labeled by CRISPR. (FIG. 14A) Conventional fluorescence image of MUC4 (left) and three example traces of marked foci (right). All traces show confined diffusion, but focus 2 is actively transported in addition. (FIG. 14B) Averaged Mean Square Displacement (MSD) of 119 and 50 traces from 26 cells, categorized as confined diffusive (darker line) and actively transported (lighter line). The shaded areas represent the standard error of the mean. (FIG. 14C) Histogram of confinement characteristic length and (FIG. 14D) histogram of microscopic diffusion coefficient derived from MSDs. (FIG. 14E) Data illustrating individual MUC4 loci movement. (FIG. 14F) Analysis of MUC4 loci movement depicts two distinct movement modes: confined diffusion and active transport of confined diffusion. (FIG. 14G) 80% of detected MUC4 loci followed confined diffusion, suggesting the movement of local chromatin is modulated by nuclear factors. (FIG. 14H) The median speed was 0.011 um 2/s as defined by diffusion coefficient.

DETAILED DESCRIPTION OF THE INVENTION

I. Definitions

Figure 1A:
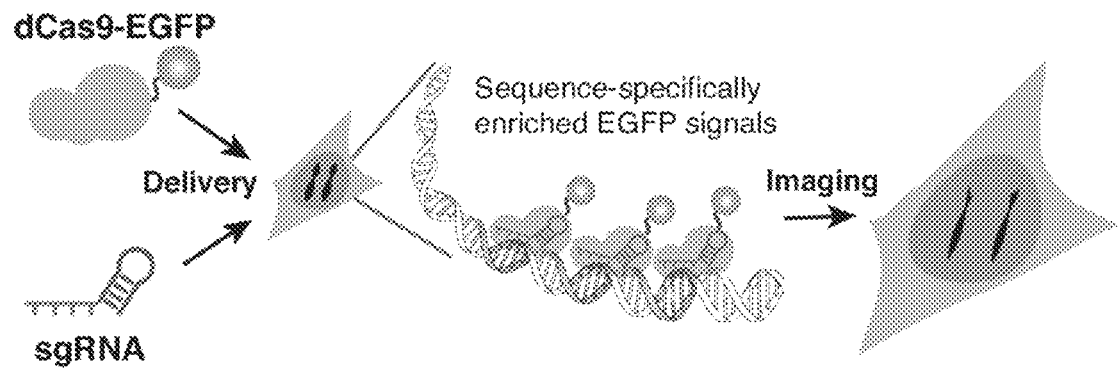

As used in this specification and the appended claims, the singular forms "a," "an," and "the" include plural reference unless the context clearly dictates otherwise.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

A "reporter gene" encodes proteins that are readily detectable due to their biochemical characteristics, such as enzymatic activity or chemifluorescent features. One specific example of such a reporter is green fluorescent protein. Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282: 864-869); luciferase (lux); β-galactosidase; LacZ; β-glucuronidase; and alkaline phosphatase (Toh, et al. (1980) Eur. J. Biochem. 182: 231-238; and Hall et al. (1983) J. Mol. Appl. Gen. 2: 101), each of which is incorporated by reference herein in the entirety. Other suitable reporters include those that encode for a particular epitope that can be detected with a labeled antibody that specifically recognizes the epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. In some cases, conservatively modified variants of Cas9 or sgRNA can have an increased stability, assembly, or activity as described herein.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same. For example, a core small guide RNA (sgRNA) sequence responsible for assembly and activity of a sgRNA:nuclease complex has at least 80% identity, preferably 85%, 90%, 91%, 92%, 93, 94%, 95%, 96%, 97%, 98%, 99%, or 100% identity, to a reference sequence, e.g., one of SEQ ID NOs:1-4), when compared and aligned for maximum correspondence over a comparison window, or designated region as measured using one of the following sequence comparison algorithms or by manual alignment and visual inspection. As another example, a Cas9 sequence responsible for assembly and activity of a sgRNA:nuclease complex has at least 80% identity, preferably 85%, 90%, 91%, 92%, 93, 94%, 95%, 96%, 97%, 98%, 99%, or 100% identity, to a reference sequence, e.g., one of SEQ ID NOs:5-6), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. With regard to amino acid sequences, preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence. Yet another indication that two polypeptides are substantially identical is that the two polypeptides retain identical or substantially similar activity.

A "translocation sequence" or "transduction sequence" refers to a peptide or protein (or active fragment or domain thereof) sequence that directs the movement of a protein from one cellular compartment to another, or from the extracellular space through the cell or plasma membrane into the cell. Translocation sequences that direct the movement of a protein from the extracellular space through the cell or plasma membrane into the cell are "cell penetration peptides." Translocation sequences that localize to the nucleus of a cell are termed "nuclear localization" sequences, signals, domains, peptides, or the like. Examples of translocation sequences include, without limitation, the TAT transduction domain (see, e.g., S. Schwarze et al., Science 285 (Sep. 3, 1999); penetratins or penetratin peptides (D. Derossi et al., Trends in Cell Biol. 8, 84-87); Herpes simplex virus type 1 VP22 (A. Phelan et al., Nature Biotech. 16, 440-443 (1998), and polycationic peptides (Cell Mol. Life Sci. 62 (2005) 1839-1849). Further translocation sequences are known in the art. Translocation peptides can be fused (e.g. at the amino or carboxy terminus), conjugated, or coupled to a compound of the present invention, to, among other things, produce a conjugate compound that may easily pass into target cells, or through the blood brain barrier and into target cells.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize the RNA-mediated nuclease,Cas9 in complex with guide and activating RNA to recognize and cleave foreign nucleic acid.

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9;497(7448):254-7; and Jinek, et al., Science. 2012 Aug. 17; 337(6096):816-21.

As used herein, "activity" in the context of CRISPR/Cas activity, Cas9 activity, sgRNA activity, sgRNA:nuclease activity and the like refers to the ability to bind to a target sequence and/or label or cleave the target sequence. Such activity can be measured in a variety of ways as known in the art. For example, expression, activity, or level of a reporter gene can be measured, and sgRNA:nucleases targeting the reporter gene sequence can be assayed for their ability to reduce the expression, activity, or level of the reporter gene. For example, a cell can be transfected with an expression cassette encoding a green fluorescent protein under the control of a constitutive promoter. The fluorescence intensity can be measured and compared to the intensity of the cell after transfection with Cas9 and candidate sgRNAs to identify optimized sgRNAs

II. Introduction

Described herein are methods and compositions for analyzing or modifying target nucleic acids. The methods and compositions are based on an optimized CRISPR/Cas system that employs a small guide RNA (sgRNA) and an sgRNA-mediated nuclease. The sgRNA contains a binding region that provides specific binding to a nucleic acid target sequence that is substantially complementary to the sequence of the binding region. The sgRNA and the nuclease can form a complex that specifically binds to the nucleic acid target sequence.

III. Compositions

In some embodiments, an small guide RNA (sgRNA) molecule is provided. sgRNAs contain a binding region that determines the sequence specificity of the sgRNA and the sgRNA:nuclease complex, a 5' stem-loop region that, at least in part, participates in assembly and interaction with a sgRNA-mediated nuclease; an intervening sequence, a 3' stem-loop region, and a termination sequence.

The binding region can be between about 5 and 100 nucleotides long, or longer (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 60, 61, 62, 63, 63, 64, 65, 66, 67, 68, 69, 70, 71, 72, 73, 74, 75, 76, 77, 78, 79, 80, 81, 82, 83, 84, 85, 86, 87, 88, 89, 90, 91 92, 93, 94, 95, 96, 97, 98, 99, or 100 nucleotides in length, or longer). In some cases, the binding region is between about 15 and about 30 nucleotides in length (e.g., about 15-29, 15-26, 15-25; 16-30, 16-29, 16-26, 16-25; or about 18-30, 18-29, 18-26, or 18-25 nucleotides in length). Generally, the binding region is designed to complement or substantially complement the target nucleic acid sequence or sequences. In some cases, the binding region can incorporate wobble or degenerate bases to bind multiple sequences. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%). In some cases, the binding region can contain modified nucleotides such as, without limitation, methylated or phosphorylated nucleotides.

The 5' stem-loop region can be between about 15 and about 50 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides in length). In some cases, the 5' stem-loop region is between about 30-45 nucleotides in length (e.g., about 31, 32, 33, 34, 35, 36, 37, 38, 39, 40, 41, 42, 43, 44, or 45 nucleotides in length). In some cases, the 5' stem-loop region is at least about 31 nucleotides in length (e.g., at least about 31, 32, 33, 34, 35, 36, 37, 38, 39, 40, 41, 42, 43, 44, or 45 nucleotides in length). In some cases, the 5' stem-loop structure contains one or more loops or bulges, each loop or bulge of about 1, 2, 3, 4, 5, 6, 7, 8, 9, or 10 nucleotides. In some cases, the 5' stem-loop structure contains a stem of between about 10 and 30 complementary base pairs (e.g., 11, 12, 13, 14, 15, 16, 17, 18, 19, 20, 21, 22, 23, 24, 25, 26, 27, 28, 29, or 30 complementary base pairs).

In some embodiments, the 5' stem-loop structure can contain protein-binding, or small molecule-binding structures. In some cases, the 5' stem-loop function (e.g., interacting or assembling with a sgRNA-mediated nuclease) can be conditionally activated by drugs, growth factors, small molecule ligands, or a protein that binds to the protein-binding structure of the 5' stem-loop. In some embodiments, the 5' stem-loop structure can contain non-natural nucleotides. For example, non-natural nucleotides can be incorporated to enhance protein-RNA interaction, or to increase the thermal stability or resistance to degradation of the sgRNA.

The intervening sequence between the 5' and 3' stem-loop structures can be between about 10 and about 50 nucleotides in length (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides in length). In some cases, the intervening sequence is designed to be linear, unstructured, substantially linear, or substantially unstructured. In some embodiments, the intervening sequence can contain non-natural nucleotides. For example, non-natural nucleotides can be incorporated to enhance protein-RNA interaction or to increase the activity of the sgRNA:nuclease complex. As another example, natural nucleotides can be incorporated to enhance the thermal stability or resistance to degradation of the sgRNA.

The 3' stem-loop structure can contain an about 3, 4, 5, 6, 7, or 8 nucleotide loop and an about 4, 5, 6, 7, 8, 9, 10, 11, 12, 13, 14, 15, 16, 17, 18, 19, 20, 21, 22, 23, 24, or 25 nucleotide or longer stem. In some cases, the 3' stem-loop can contain a protein-binding, small molecule-binding, hormone-binding, or metabolite-binding structure that can conditionally stabilize the secondary and/or tertiary structure of the sgRNA. In some embodiments, the 3' stem-loop can contain non-natural nucleotides. For example, non-natural nucleotides can be incorporated to enhance protein-RNA interaction or to increase the activity of the sgRNA:nuclease complex. As another example, natural nucleotides can be incorporated to enhance the thermal stability or resistance to degradation of the sgRNA.

In some embodiments, the sgRNA includes a termination structure at its 3' end. In some cases, the sgRNA includes an additional 3' hairpin structure, e.g., before the termination structure, that can interact with proteins, small-molecules, hormones, etc., for stabilization or additional functionality, such as conditional stabilization or conditional regulation of sgRNA:nuclease assembly or activity.

In some cases, the sgRNA is optimized to enhance stability, assembly, and/or expression. In some case, the sgRNA is optimized to enhance the activity of a sgRNA:nuclease complex as compared to previously known sgRNAs, such as an sgRNA encoded by:

$$\text{SEQ ID NO: 1}$$
$$[N]_5\text{-}$$
$$_{100}\text{GUUUUAGAGCUAGAAAUAGCAAGUUAAAAUAAGGCUAGUC}$$
$$\text{CGUUAUCAACUUGAAAAAGUGGCACCGAGUCGGUGCUUUUUU}$$
$$\text{U,}$$

where [N] represents a target specific binding region of between about 5-100 nucleotides (e.g., about 5, 10, 15, 20, 15, 30, 35, 40, 45, 50, 55, 60, 70, 80, or 90 nucleotides) that is complementary or substantially complementary to the target nucleic acid. In some cases, the optimized sgRNA provides enhanced activity as compared to a previously known sgRNA or an sgRNA substantially identical to a previously known sgRNA. As used herein, identity of an sgRNA to another sgRNA, such as an sgRNA to SEQ ID NO:1 is determined with reference to the identity to the nucleotide sequences outside of the binding region. For example, two sgRNAs with 0% identity inside the binding region and 100% identity outside the binding region are 100% identical to each other. Similarly, as used herein, number of substitutions, additions, or deletions of an sgRNA as compared to another, such as an sgRNA compared to SEQ ID NO:1 is determined with reference to the nucleotide sequences outside of the binding region. For example, two sgRNAs with multiple additions, substitutions, and/or deletions inside the binding region and 100% identity outside the binding region are considered to contain 0 nucleotide substitutions, additions, or deletions.

In some cases, the optimized sgRNAs described herein form an sgRNA:nuclease complex with enhanced activity as compared to SEQ ID NO:1, or an sgRNA 90, 95, 96, 97, 98, or 99% or more identical to SEQ ID NO:1. In some cases, the optimized sgRNAs described herein form an sgRNA:nuclease complex with enhanced activity as compared to SEQ ID NO:1, or an sgRNA with fewer than 5, 4, 3, or 2 nucleotide substitutions, additions, or deletions of SEQ ID NO:1.

In some embodiments, the sgRNA can be optimized for expression by substituting, deleting, or adding one or more nucleotides. In some cases, a nucleotide sequence that provides inefficient transcription from an encoding template nucleic acid can be deleted or substituted. For example, in some cases, the sgRNA is transcribed from a nucleic acid operably linked to an RNA polymerase III promoter. In such cases, sgRNA sequences that result in inefficient transcription by RNA polymerase III, such as those described in Nielsen et al., Science. 2013 Jun. 28; 340(6140):1577-80, can be deleted or substituted. For example, one or more consecutive uracils can be deleted or substituted from the sgRNA sequence. In some cases, the consecutive uracils are present in the stem portion of a stem-loop structure. In such cases, one or more of the consecutive uracils can be substituted by exchanging the uracil and its complementary base. For example, if the uracil is hydrogen bonded to a corresponding adenine, the sgRNA sequence can be altered to exchange the adenine and uracil. This "A-U flip" can retain the overall structure and function of the sgRNA molecule while improving expression by reducing the number of consecutive uracil nucleotides. In some cases, the sgRNA containing an A-U flip is encoded by:

$$\text{SEQ ID NO: 2}$$
$$[N]_5\text{-}$$
$$_{100}\text{GUUU}\underline{\text{A}}\text{AGAGCUAGAAAUAGCAAGUUU}\underline{\text{A}}\text{AAUAAGGCUAGUC}$$
$$\text{CGUUAUCAACUUGAAAAAGUGGCACCGAGUCGGUGCUUUUUU}$$
$$\text{U,}$$

where the A-U flipped nucleotides are underlined. In some cases, the optimized sgRNA is at least 90, 91, 92, 93, 94, 95, 96, 97, 98, or 99% identical or more to SEQ ID NO:2, or contains fewer than 10, 9, 8, 7, 6, 5, 4, 3, or 2 nucleotide additions, deletions, or substitutions compared to SEQ ID NO:2. Alternatively, the A-U pair can be replaced by a G-C, C-G, A-C, G-U pair.

In some embodiments, the sgRNA can be optimized for stability. Stability can be enhanced by optimizing the stability of the sgRNA:nuclease interaction, optimizing assembly of the sgRNA:nuclease complex, removing or altering RNA destabilizing sequence elements, or adding RNA stabilizing sequence elements. In some embodiments, the sgRNA contains a 5' stem-loop structure proximal to, or adjacent to, the binding region that interacts with the sgRNA-mediated nuclease. Optimization of the 5' stem-loop structure can provide enhanced stability or assembly of the sgRNA:nuclease complex. In some cases, the 5' stem-loop structure is optimized by increasing the length of the stem portion of the stem-loop structure. An exemplary sgRNA containing an optimized 5' stem-loop structure is encoded by:

$$\text{SEQ ID NO: 3}$$
$$[N]_5\text{-}$$
$$_{100}\text{GUUUUAGAGCUAU}\underline{\text{GCUGGAAA}}\text{CAGCAUAGCAAGUUAAAAU}$$
$$\text{AAGGCUAGUCCGUUAUCAACUUGAAAAAGUGGCACCGAGUCG}$$
$$\text{GUGCUUUUUU,}$$

where the nucleotides contributing to the elongated stem portion of the 5' stem-loop structure are underlined. In some cases, the optimized sgRNA is at least 90, 91, 92, 93, 94, 95, 96, 97, 98, or 99% identical or more to SEQ ID NO:3, or contains fewer than 10, 9, 8, 7, 6, 5, 4, 3, or 2 nucleotide additions, deletions, or substitutions compared to SEQ ID NO:3.

In some embodiments, the 5' stem-loop optimization is combined with mutations for increased transcription to provide an optimized sgRNA. For example, an A-U flip and an elongated stem loop can be combined to provide an optimized sgRNA. An exemplary sgRNA containing an A-U flip and an elongated 5' stem-loop is encoded by:

SEQ ID NO: 4

[N]$_5$-

$_{100}$GUUU<u>A</u>AGAGCUA<u>UGCUGGAAA</u>C<u>AGCA</u>UAGCAAGUUU<u>A</u>AAU

AAGGCUAGUCCGUUAUCAACUUGAAAAAGUGGCACCGAGUCG

GUGCUUUUUU, where the A-U flipped nucleotides and the nucleotides contributing to the elongated stem portion of the 5' stem-loop structure are underlined. In some cases, the optimized sgRNA is at least 90, 91, 92, 93, 94, 95, 96, 97, 98, or 99% identical or more to SEQ ID NO:4, or contains fewer than 10, 9, 8, 7, 6, 5, 4, 3, or 2 nucleotide additions, deletions, or substitutions compared to SEQ ID NO:4.

sgRNAs can be modified by methods known in the art. In some cases, the modifications can include, but are not limited to, the addition of one or more of the following sequence elements: a 5' cap (e.g., a 7-methylguanylate cap); a 3' polyadenylated tail; a riboswitch sequence; a stability control sequence; a hairpin; a subcellular localization sequence; a detection sequence or label; or a binding site for one or more proteins. Modifications can also include the introduction of non-natural nucleotides including, but not limited to, one or more of the following: fluorescent nucleotides and methylated nucleotides.

In some embodiments, the sgRNA can contain from 5' to 3': (i) a binding region of between about 10 and about 50 nucleotides; (ii) a 5' hairpin region containing fewer than four consecutive uracil nucleotides, or a length of at least 31 nucleotides (e.g., from about 31 to about 41 nucleotides); (iii) a 3' hairpin region; and (iv) a transcription termination sequence, wherein the small guide RNA is configured to form a complex with a small guide RNA-mediated nuclease, the complex having increased stability or activity relative to a complex containing a small guide RNA-mediated nuclease and a small guide RNA comprising at least 95% identity to SEQ ID NO:1 or a complement thereof.

In some embodiments, an sgRNA-mediated nuclease is provided. In some cases, the sgRNA-mediated nuclease is a Cas9 protein. For example, the sgRNA-mediated nuclease can be a type I, II, or III Cas9 protein. In some cases, the sgRNA-mediated nuclease can be a modified Cas9 protein. Cas9 proteins can be modified by any method known in the art. For example, the Cas9 protein can be codon optimized for expression in host cell or an in vitro expression system. Additionally, or alternatively, the Cas9 protein can be engineered for stability, enhanced target binding, or reduced aggregation.

In some cases, the Cas9 protein can be engineered to be nuclease deficient. For example, the Cas9 protein generally catalyzes double-stranded cleavage of the target nucleic acid; however, certain Cas9 mutations can provide a nuclease that is able to nick the target nucleic acid but unable to catalyze double-stranded cleavage, or unable to substantially catalyze double-stranded cleavage. Exemplary mutations that reduce or eliminate double stranded cleavage but provide nicking activity include one or more mutations in the following locations: D10, G12, G17, E762, H840, N854, N863, H982, H983, A984, D986, or A987, or a mutation in a corresponding location in a Cas9 homologue or ortholog. The mutation(s) can include substitution with any natural (e.g., alanine) or non-natural amino acid, or deletion. Cas9 proteins that cleave or nick the target sequence can be utilized in combination with an sgRNA, such as one or more of the sgRNAs described herein, to form a complex that is useful for various nucleic acid modification methods, such as genome editing as further explained below. An exemplary nicking Cas9 protein is Cas9D10A or Cas9H840A (Jinek, et al., Science. 2012 Aug. 17; 337(6096):816-21).

The Cas9D10A amino acid sequence is (D10A mutation underlined):

SEQ ID NO: 5

MDKKYSIGL<u>A</u>IGTNSVGWAVITDEYKVPSKKFKVLGNTDRHS

IKKNLIGALLFDSGETAEATRLKRTARRRYTRRKNRICYLQE

IFSNEMAKVDDSFFHRLEESFLVEEDKKHERHPIFGNIVDEV

AYHEKYPTIYHLRKKLVDSTDKADLRLIYLALAHMIKFRGHF

LIEGDLNPDNSDVDKLFIQLVQTYNQLFEENPINASGVDAKA

ILSARLSKSRRLENLIAQLPGEKKNGLFGNLIALSLGLTPNF

KSNFDLAEDAKLQLSKDTYDDDLDNLLAQIGDQYADLFLAAK

NLSDAILLSDILRVNTEITKAPLSASMIKRYDEHHQDLTLLK

ALVRQQLPEKYKEIFFDQSKNGYAGYIDGGASQEEFYKFIKP

ILEKMDGTEELLVKLNREDLLRKQRTFDNGSIPHQIHLGELH

AILRRQEDFYPFLKDNREKIEKILTFRIPYYVGPLARGNSRF

AWMTRKSEETITPWNFEEVVDKGASAQSFIERMTNFDKNLPN

EKVLPKHSLLYEYFTVYNELTKVKYVTEGMRKPAFLSGEQKK

AIVDLLFKTNRKVTVKQLKEDYFKKIECFDSVEISGVEDRFN

ASLGTYHDLLKIIKDKDFLDNEENEDILEDIVLTLTLFEDRE

MIEERLKTYAHLFDDKVMKQLKRRRYTGWGRLSRKLINGIRD

KQSGKTILDFLKSDGFANRNFMQLIHDDSLTFKEDIQKAQVS

GQGDSLHEHIANLAGSPAIKKGILQTVKVVDELVKVMGRHKP

ENIVIEMARENQTTQKGQKNSRERMKRIEEGIKELGSQILKE

HPVENTQLQNEKLYLYYLQNGRDMYVDQELDINRLSDYDVDH

IVPQSFLKDDSIDNKVLTRSDKNRGKSDNVPSEEVVKKMKNY

WRQLLNAKLITQRKFDNLTKAERGGLSELDKAGFIKRQLVET

RQITKHVAQILDSRMNTKYDENDKLIREVKVITLKSKLVSDF

RKDFQFYKVREINNYHHAHDAYLNAVVGTALIKKYPKLESEF

VYGDYKVYDVRKMIAKSEQEIGKATAKYFFYSNIMNFFKTEI

TLANGEIRKRPLIETNGETGEIVWDKGRDFATVRKVLSMPQV

NIVKKTEVQTGGFSKESILPKRNSDKLIARKKDWDPKKYGGF

DSPTVAYSVLVVAKVEKGKSKKLKSVKELLGITIMERSSFEK

NPIDFLEAKGYKEVKKDLIIKLPKYSLFELENGRKRMLASAG

ELQKGNELALPSKYVNFLYLASHYEKLKGSPEDNEQKQLFVE

-continued

QHKHYLDEIIEQISEFSKRVILADANLDKVLSAYNKHRDKPI

REQAENIIHLFTLTNLGAPAAFKYFDTTIDRKRYTSTKEVLD

ATLIHQSITGLYETRIDLSQLGGD.

The Cas9H840A amino acid sequence is (H840A mutation underlined):

SEQ ID NO: 6

MDKKYSIGLDIGTNSVGWAVITDEYKVPSKKFKVLGNTDRHS

IKKNLIGALLFDSGETAEATRLKRTARRRYTRRKNRICYLQE

IFSNEMAKVDDSFFHRLEESFLVEEDKKHERHPIFGNIVDEV

AYHEKYPTIYHLRKKLVDSTDKADLRLIYLALAHMIKFRGHF

LIEGDLNPDNSDVDKLFIQLVQTYNQLFEENPINASGVDAKA

ILSARLSKSRRLENLIAQLPGEKKNGLFGNLIALSLGLTPNF

KSNFDLAEDAKLQLSKDTYDDDLDNLLAQIGDQYADLFLAAK

NLSDAILLSDILRVNTEITKAPLSASMIKRYDEHHQDLTLLK

ALVRQQLPEKYKEIFFDQSKNGYAGYIDGGASQEEFYKFIKP

ILEKMDGTEELLVKLNREDLLRKQRTFDNGSIPHQIHLGELH

AILRRQEDFYPFLKDNREKIEKILTFRIPYYVGPLARGNSRF

AWMTRKSEETITPWNFEEVVDKGASAQSFIERMTNFDKNLPN

EKVLPKHSLLYEYFTVYNELTKVKYVTEGMRKPAFLSGEQKK

AIVDLLFKTNRKVTVKQLKEDYFKKIECFDSVEISGVEDRFN

ASLGTYHDLLKIIKDKDFLDNEENEDILEDIVLTLTLFEDRE

MIEERLKTYAHLFDDKVMKQLKRRRYTGWGRLSRKLINGIRD

KQSGKTILDFLKSDGFANRNFMQLIHDDSLTFKEDIQKAQVS

GQGDSLHEHIANLAGSPAIKKGILQTVKVVDELVKVMGRHKP

ENIVIEMARENQTTQKGQKNSRERMKRIEEGIKELGSQILKE

HPVENTQLQNEKLYLYYLQNGRDMYVDQELDINRLSDYDVDA

IVPQSFLKDDSIDNKVLTRSDKNRGKSDNVPSEEVVKKMKNY

WRQLLNAKLITQRKFDNLTKAERGGLSELDKAGFIKRQLVET

RQITKHVAQILDSRMNTKYDENDKLIREVKVITLKSKLVSDF

RKDFQFYKVREINNYHHAHDAYLNAVVGTALIKKYPKLESEF

VYGDYKVYDVRKMIAKSEQEIGKATAKYFFYSNIMNFFKTEI

TLANGEIRKRPLIETNGETGEIVWDKGRDFATVRKVLSMPQV

NIVKKTEVQTGGFSKESILPKRNSDKLIARKKDWDPKKYGGF

DSPTVAYSVLVVAKVEKGKSKKLKSVKELLGITIMERSSFEK

NPIDFLEAKGYKEVKKDLIIKLPKYSLFELENGRKRMLASAG

ELQKGNELALPSKYVNFLYLASHYEKLKGSPEDNEQKQLFVE

QHKHYLDEIIEQISEFSKRVILADANLDKVLSAYNKHRDKPI

REQAENIIHLFTLTNLGAPAAFKYFDTTIDRKRYTSTKEVLD

ATLIHQSITGLYETRIDLSQLGGD.

As another example, certain Cas9 mutations can provide a nuclease that is nuclease defective. For example, certain Cas9 mutations can provide a nuclease that does not cleave or nick, or does not substantially cleave or nick the target sequence. Exemplary mutations that reduce or eliminate nuclease activity include one or more mutations in the following locations: D10, G12, G17, E762, H840, N854, N863, H982, H983, A984, D986, or A987, or a mutation in a corresponding location in a Cas9 homologue or ortholog. The mutation(s) can include substitution with any natural (e.g., alanine) or non-natural amino acid, or deletion. Cas9 proteins that do not cleave or nick the target sequence can be utilized in combination with an sgRNA, such as one or more of the sgRNAs described herein, to form a complex that is useful for detection of target nucleic acids as further explained below. An exemplary nuclease defective Cas9 protein is Cas9D10A&H840A (Jinek, et al., Science. 2012 Aug. 17; 337(6096):816-21; Qi, et al., Cell. 2013 Feb. 28; 152(5):1173-83).

In some embodiments, the Cas9 protein can be conjugated or fused to a detectable label. In some cases Cas9 is fused to a fluorescent protein. For example, a fluorescent protein can be fused at the N and/or C-terminus of the Cas9 protein. In some cases, the Cas9 protein is nuclease deficient and labeled. In such cases, the labeled Cas9 protein can be combined with an sgRNA, such as an sgRNA provided herein, to form a complex useful as a detection reagent in a cell.

In some embodiments, the Cas9 protein can be conjugated or fused to a protein localization signal or a cell penetration peptide. For example, the Cas9 protein can be fused to one or more nuclear localization signals, one or more mitochondrial localization signals, or one or more chloroplast localization signals.

In some embodiments, expression cassettes are provided for expression of sgRNAs and/or Cas9. In some cases, the expression cassettes are configured to express sgRNAs and/or Cas9 in an in vivo system. Alternatively, the expression cassettes can be configured to express sgRNAs and/or Cas9 in an in vitro system. In some cases, the expression cassette is configured to express one or more sgRNAs and/or Cas9 in the same host cell in which nucleic acid modification or detection is to be performed.

Expression cassettes as described herein can include a promoter operably linked to a nucleotide encoding sgRNA or Cas9. In some embodiments the expression cassettes also include one or more nuclear localization signals, one or more mitochondrial localization signals, or one or more chloroplast localization signals. The nuclear localization signal can be fused to the N and/or C-terminus of a Cas9 coding sequence. In some cases, additional sequences are included in the expression cassette, such as cell penetration peptides, purification tags, detection labels, or termination sequences. Termination sequences include stop codons, transcriptional termination signals, or polyadenylation signals. Detection labels include fluorescent proteins, such as green fluorescent protein, yellow fluorescent protein, blue fluorescent protein, mCherry, and the like.

sgRNA expression cassettes can utilize a wide range of suitable promoters as known in the art. In some cases, sgRNA expression cassettes operably link a strong promoter to the sgRNA encoding nucleic acid to provide a high level of expression in a specified expression system or host cell. For example, an RNA polymerase III promoter, such as H1 or U6, can be operably linked to an sgRNA encoding nucleic acid for in vivo expression in a mammalian cell. Other suitable mammalian promoters can also be utilized. Exemplary suitable promoters for sgRNA expression are provided in e.g., Addgene, Cas9 expression cassettes can utilize a wide range of suitable promoters as known in the art. In some cases, the Cas9, or modified Cas9, utilized in the host cell is prone to aggregation or mislocalization. In some cases Cas9 expression cassettes operably link a weak promoter to the Cas9 encoding nucleic acid to provide a low level of expression in the host cell. In some cases, the weak expression level mitigates, ameliorates, or eliminates the aggregation and/or mislocalization of Cas9 in the host cell. Alternatively, the Cas9 is operably linked to a strong promoter to provide reagent quantities of Cas9 from an in vitro or in vivo expression system. Reagent quantities of Cas9 can then be purified from the expression system for subsequent use in a cell as described below. Suitable strong promoters include promoters described in e.g., Addgene. Suitable weak mammalian promoters include the ubiquitin C promoter, the phosphoglycerate kinase 1 promoter, and the un-induced TetOn promoter. In some cases, the weak or strong promoters are respectively weaker or stronger than the elongation factor 1a (EF1a) promoter, which is known to provide a moderate level of expression in a broad range of mammalian cell types.

Also provided are expression systems for expression of reagent quantities of sgRNA and/or Cas9. In some cases, the expression systems include an expression cassette containing a nucleic acid encoding an sgRNA. In some cases, the expression systems include an expression cassette containing a nucleic acid encoding a Cas9 protein. In some cases, the expression systems contain one or more of the foregoing expression cassettes and a host cell or cell-lysate for generating reagent quantities of sgRNA and/or Cas9. The expression cassettes can be introduced into the host cell or cell-lysate and incubated for production of sgRNA or Cas9. The sgRNA and/or Cas9 product(s) can be purified and used in the methods of the present invention.

Also provided are host cells containing nucleic acid detection or modification reagents. In some cases, the host cells contain one or more sgRNAs, one or more sgRNA-mediated nucleases, or one or more sgRNA:nuclease complexes. In some cases, the host cells are transfected with a suitable vector containing one or more expression cassettes encoding an sgRNA and/or Cas9 protein. Suitable vectors include any vectors that are known in the art and capable of transferring nucleic acid to a host cell. Suitable vectors include, but are not limited to one or more of the following viral vectors: an oncoviral vector, a foamy viral vector, lentiviral vector, a feline immunodeficiency viral vector, a Moloney murine leukemia virus (MoMLV) vector, a vaccinia viral vector, a polioviral vector, an adenoviral vector, an adeno-associated viral vector, an SV40 viral vector, a herpes simplex viral vector, an HIV viral vector, a spleen necrosis viral vector, a Rous Sarcoma viral vector, a Harvey Sarcoma viral vector, an avian leucosis viral vector, a myeloproliferative sarcoma viral vector, or a mammary tumor viral vector.

In some cases, the sgRNA, Cas9, or sgRNA:nuclease complexes are introduced into a host cell. Suitable methods for introduction of the RNA, protein, or complex are known in the art and include, for example, electroporation; calcium phosphate precipitation; or PEI, PEG, DEAE, nanoparticle, or liposome mediated transformation. Other suitable transfection methods include direct micro-injection. In some cases, the sgRNA and Cas9 are introduced separately and the sgRNA:nuclease complexes are formed in the cell. In other cases, the sgRNA:nuclease complexes are formed and then introduced into the cell. In some cases, multiple, differentially labeled, sgRNA:nuclease complexes, each directed to a different nucleic acid target or nucleic acid target region are formed and then introduced into the cell.

IV. Methods

Methods for detecting a target nucleic acid sequence are described herein. In some embodiments, the methods utilize a nuclease defective Cas9 protein. For example, a complex between an sgRNA and a Cas9 protein (e.g., a nuclease defective Cas9) can be formed and contacted with a nucleic acid containing the target sequence. In some cases, the nucleic acid resides in a host cell, e.g., a living host cell. For example, sgRNA and Cas9 can be expressed in, or otherwise introduced into, a host cell, and the sgRNA and Cas9 can form an sgRNA:nuclease complex and localize to the target nucleic acid sequence. Alternatively, sgRNA can be expressed in the host cell and Cas9 introduced using a method known in the art for protein transfection. For example, Cas9 fused to a cell penetration peptide can be contacted with the sgRNA containing cell. As yet another alternative, Cas9 can be expressed in the cell and sgRNA introduced into the cell using any method known in the art for RNA transfection. As yet another alternative sgRNA:nuclease complexes can be formed and introduced into the cell.

sgRNA:nuclease complexes can localize to a target nucleic acid sequence that is complementary, or substantially complementary to the binding region of the sgRNA. Such localized sgRNA:nuclease complexes can be detected to detect the target nucleic acid sequence, or a region containing the target nucleic acid. For example, the nuclease and/or the sgRNA can be labeled and detection of the localized label thereby detects the target nucleic acid sequence. In some cases, multiple different sgRNAs, each corresponding to a different target sequence in a nucleic acid region can be used to amplify the signal. For example, 5, 10, 15, 20, 25, 30, or more sgRNAs can be designed that each bind to a different sequence corresponding to a specified gene or chromosomal region. These sgRNAs and a labeled Cas9 can be introduced into a host cell and their localization detected. The presence of a strong and localized nuclear signal indicates the presence of the target gene or chromosomal region. Alternatively, a small number of sgRNAs (e.g., 5, 4, 3, 2, or 1) can be designed to bind to a repetitive sequence located in a target gene or chromosomal region and, e.g., introduced into a cell to form an sgRNA:nuclease complex. The sgRNA:nuclease complex can localize to the repeat region and provide a strong signal.

In some embodiments, an sgRNA:nuclease complex can be used to enhance other chromosomal detection methods. For example an sgRNA targeted to a nucleic acid sequence or region of interest and an Cas9 protein can be introduced into a cell. The cell can be incubated to allow formation and localization of the sgRNA:nuclease complex. Helicase activity of the sgRNA:nuclease complex can then relax the target nucleic acid and surrounding regions. The cells can then be fixed and stained using standard fluorescence in situ hybridization (FISH) protocols. The relaxed regions can then be more readily and routinely detected by FISH. In some cases, the sgRNA:nuclease complexes used to enhance other detection methods such as FISH are labeled. In other cases, the sgRNA:nuclease complexes used to enhance other detection methods are not labeled. Labeled sgRNA:nuclease complexes can provide for co-localization detection or detection of multiple sequences or regions in addition to, or in combination with the other detection method (e.g., FISH).

Similarly, an sgRNA:nuclease provided herein can be used to enhance any methods known in the art that rely on access to chromosomal DNA. For example, genome editing with TALENS or Zinc Finger nucleases can be enhanced by targeting sgRNA:nucleases (e.g., nuclease active, nuclease deficient, or nuclease defective) to a region at or near the TALEN or Zinc Finger nuclease target site. Similarly, activators or repressors can targeted to regions at or near sgRNA:nuclease target sites. In some cases, the helicase activity of the sgRNA:nuclease unwinds, or relaxes the target nucleic acid region, or creates a more open chromosomal structure providing access to other tools known in the art for genome editing, labeling, or transcriptional regulation.

In some embodiments, the methods described herein provide diagnostics for genetic diseases. For example, the methods can be used to detect chromosomal number, chromosomal rearrangements, mutations, insertions, deletions, and the presence or absence of a gene or region of a gene.

Methods for modifying a target nucleic acid sequence are described herein. In some embodiments, the methods utilize a nuclease deficient Cas9 protein. In other embodiments, the methods utilize a Cas9 protein that catalyzes double stranded cleavage of the target nucleic acid. For example, a complex between an sgRNA and a Cas9 protein (e.g., a nicking Cas9 protein or a Cas9 protein capable of double stranded cleavage) can be formed and contacted with a nucleic acid containing the target sequence. In some cases, the nucleic acid resides in a host cell, e.g., a living host cell. For example, sgRNA and Cas9 can be expressed in a host cell, the sgRNA and Cas9 can form an sgRNA:nuclease complex and localize to the target nucleic acid sequence. Alternatively, sgRNA can be expressed in the host cell and Cas9 introduced using a method known in the art for protein transfection. For example, Cas9 fused to a cell penetration peptide can be contacted with the sgRNA containing cell. As yet another alternative, Cas9 can be expressed in the cell and sgRNA introduced into the cell using any method known in the art for RNA transfection.

sgRNA:nuclease complexes can localize to a target nucleic acid sequence that is complementary, or substantially complementary to the binding region of the sgRNA. The localized sgRNA:nuclease complexes can then nick or cleave the target sequence. In some cases, a pair of sgRNA: nuclease complexes are utilized that flank a nucleic acid region of interest. The nicking or cleaving of target nucleic acid sequences that flank the region of interest can then activate repair processes in the host cell. For example, non homologous end joining (NHEJ) of flanking double stranded breaks can cause deletion of at least a portion of the flanked region of interest. Alternatively, homologous DNA repair (HDR) can cause incorporation of a homologous region and lead to loss of heterozygosity in the host cell.

As yet another alternative, a heterologous nucleic acid can be introduced into the cell with regions of homology corresponding to at least a portion of the nucleic acid region of interest and/or one or more target nucleic acid sequences. Thus, HDR can incorporate at least a portion of the heterologous nucleic acid into the flanked region of interest. In some cases, the heterologous nucleic acid can contain one or more selectable markers or detectable labels to assay for successful incorporation or select for cells that have incorporated the nucleic acid. For example, the heterologous nucleic acid can encode a detectable or selectable protein, e.g. an enzyme, transcription factor, or binding protein.

V. Kits

Kits are described herein for modifying or detecting nucleic acids. For example, the kits can be used for detecting nucleic acids in a living cell. In some embodiments, the kits contain a labeled nuclease defective sgRNA and an sgRNA-mediated nuclease. In other embodiments, the kits contain a nuclease deficient, or a nuclease competent sgRNA-mediated nuclease and an sgRNA. In some cases, the kits contain multiple sgRNAs directed to different target nucleic acid sequences. In some cases, the kits contain multiple labeled sgRNA-mediated nucleases. In some embodiments, the kits contain one or more expression cassettes containing nucleic acid encoding one or more of the sgRNAs and/or sgRNA-mediated nucleases described herein.

Further uses of the methods, compositions, or kits described herein include one or more of the following: genome editing, transcriptional or epigenetic regulation, genome imaging, copy number analysis, analysis of living cells, detection of highly repetitive genome sequence or structure, detection of complex genome sequences or structures, detection of gene duplication or rearrangement, enhanced FISH labeling, unwinding of target nucleic acid, large scale diagnostics of diseases and genetic disorders related to genome deletion, duplication, and rearrangement, use of an RNA oligo chip with multiple unique sgRNAs for high-throughput imaging and/or diagnostics, multicolor differential detection of target sequences, identification or diagnosis of diseases of unknown cause or origin, and 4-dimensional (e.g., time-lapse) or 5-dimensional (e.g., multicolor time-lapse) imaging of cells (e.g., live cells), tissues, or organisms.

EXAMPLES

The following examples are provided by way of illustration only and not by way of limitation. Those of skill in the art will readily recognize a variety of non-critical parameters that could be changed or modified to yield essentially the same or similar results.

Example 1: Dynamic Imaging of the Genome in Living Human Cells Via CRISPR

Introduction

Understanding the dynamic organization and function of genomes requires methods for sequence-specific imaging of genetic elements in living cells. In human cells, the functional output of a genome is strongly determined by its dynamic spatial conformation and interaction with other RNA and protein factors (Misteli, 2007; Misteli, 2013), yet methods for robustly detecting such dynamic information are missing. Artificially synthesized nucleic acid probes and engineered DNA-binding proteins have allowed in situ detection of genetic elements such as telomeres. While fluorescence in situ hybridization (FISH) using fluorescent probes is a rapid method for detecting specific DNA sequences on chromosomes based on Watson-Crick complementarity (Pardue, et al., 1969). FISH requires chemical fixation of cells, precluding its use for live cell imaging. Unlike nucleic acid probes, DNA-binding proteins fused with fluorescent proteins have enabled robust dynamic imaging of chromosomes in living cells (Robinett, et al., 1996; Wang, et al., 2008). Due to either fixed DNA sequence binding requirements or limited native DNA-binding proteins, however, it remains challenging to use DNA-binding protein for imaging arbitrary genes and genetic elements. We argue that more powerful dynamic genome imaging approaches require methods that could leverage the ease of Watson-Crick base-pairing as seen in nucleic acid probes and the robustness of DNA-binding proteins.

The bacterial genetic immune system CRISPR (clustered regularly interspaced short palindromic repeats) provides a natural example for DNA targeting using both a DNA-binding protein and a small base-pairing RNA (Barrangou, et al., 2007; Wiedenheft, et al., 2012). The minimal type II CRISPR system derived from *Streptococcus pyogenes* recognizes specific DNA sequences via a small guide (sg) RNA-mediated nuclease, Cas9 (Deltcheva, et al., 2011; Jinek, et al., 2012). Upon DNA binding, the Cas9-sgRNA complex causes DNA double-stranded breaks (Jinek, et al., 2012). Harnessing this unique RNA-guided nuclease activity, recent work has demonstrated the use of CRISPR for genome editing in a broad range of organisms (Cong, et al., 2013; Mali, et al., 2013; Wang, et al., 2013). Furthermore, a repurposed nuclease-deactivated Cas9 (dCas9) protein has been used to regulate endogenous gene expression by controlling the RNA polymerase activity or by modulating promoter accessibility when fused with transcription factors (Qi, et al., 2013; Gilbert, et al., 2013). Beyond using CRISPR for gene editing or regulation, we hypothesized that the system could offer a promising platform for in situ dynamic imaging of genetic elements in living cells.

Results and Discussion

Figure 1B:
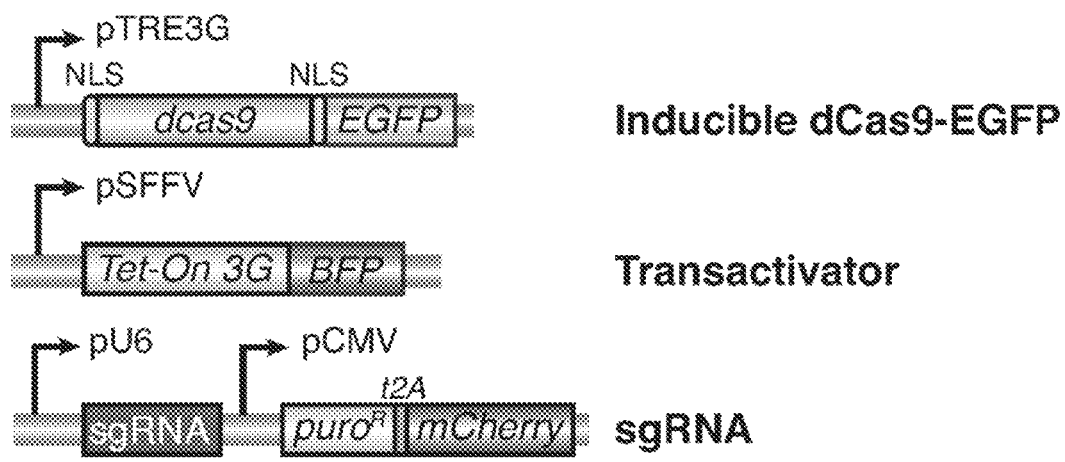
Figure 2:
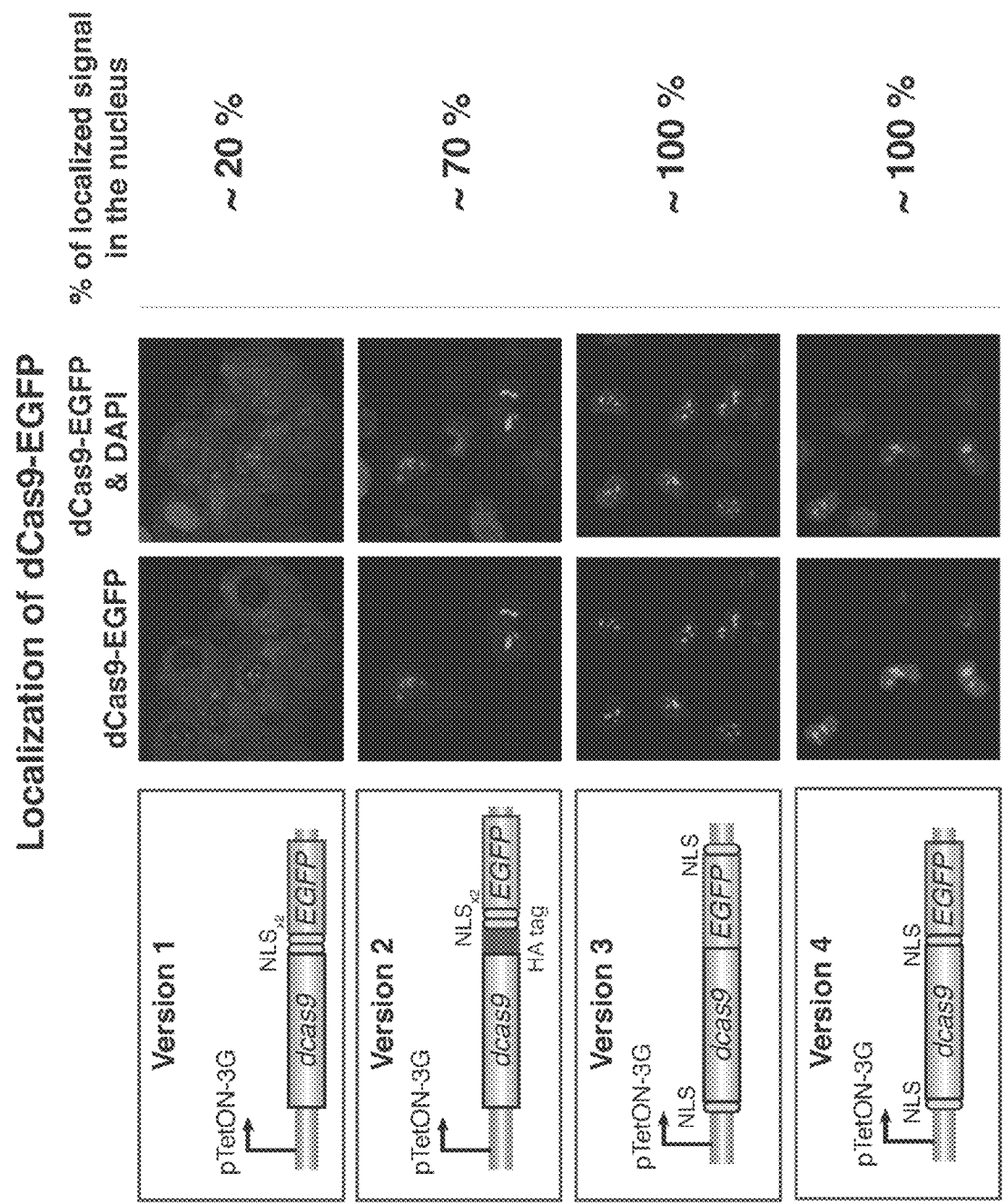
FIG. 2 different dCas9 and nuclear localization signal (NLS) fusion proteins show varied efficiencies for nucleus localization. Two copies of NLSs were fused to dCas9-EGFP at different positions. Version 1 containing two tandem NLSs between dCas9 and EGFP shows only 20% nuclear localization, which can be enhanced by insertion of a HA tag as shown in Version 2. Version 3 and 4, with an N-terminal NLS, shows almost 100% nuclear localization of dCas9-EGFP. The nucleus is labeled with DAPI. Scale bar, 51,tm

To engineer the CRISPR system for imaging endogenous genetic elements, we fused the dCas9 protein to Enhanced Green Fluorescent Protein (EGFP). In this way, complementary sgRNAs will direct dCas9-EGFP to the targeted genomic loci (FIG. 1A). To enrich the signal over the background of unbound dCas9-EGFP, we targeted multiple dCas9-EGFP proteins to a given locus. To reduce the levels of free dCas9-EGFP that contribute to background, we expressed dCas9-EGFP from the Tet-On 3G promoter without doxycycline induction (FIG. 1B). To better localize the dCas9-EGFP protein to the nucleus for genome targeting, we tested different fusions carrying two copies of a nuclear localization signal (NLS) sequence (FIG. 2), and used a resulting fully nuclear localized version (#4) for subsequent imaging experiments.

Figure 1D:
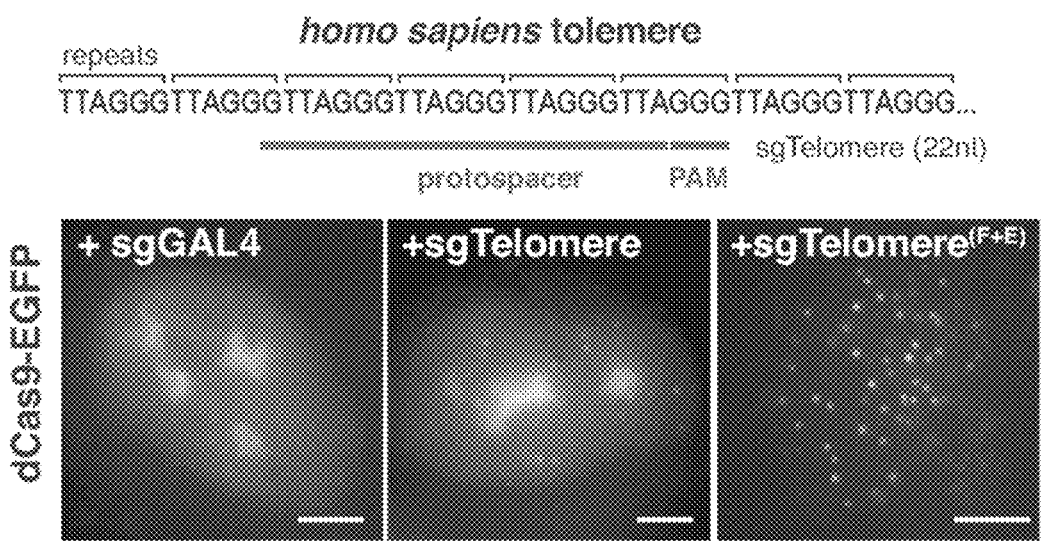

To test if the CRISPR system can detect non-coding genetic elements, we imaged human telomeres, specialized chromatin structures composed of TTAGGG repeats 5 to 15 kilobase pairs (kb) in length (Moyzis, et al., 1988). We designed an sgRNA (sgTelomere) that contains a 22-nt region complementary to the telomere sequence, expressed from a murine polymerase III U6 promoter (FIG. 1B & Table 1). The sgRNA also contained a redesigned stem-loop hairpin structure, and a *S. pyogenes* terminator sequence following previous studies (Jinek, et al., 2012; Qi, et al., 2013) (FIG. 1C). We created a clonal RPE cell line for stable dCas9-EGFP expression using lentiviruses containing the dCas9-EGFP expression cassette. This cell line was subsequently infected by sgTelomere-containing lentivirus, and imaged for telomere detection 48 h post-infection. Most cells (80%) showed 10 to 40 puncta with bright nuclear areas resembling nucleoli (FIG. 1D). The observed number of puncta was substantially lower than numbers expected for telomeres in human cells, suggesting that the system was sub-optimal.

TABLE 1

Protopacer sequences of telomeres, MUC1 and MUC4, highlighted in bold, PAM:

| Genomic target | Protospacer sequences | SEQ ID NO: |
|---|---|---|
| Telomere | gttagggttagggttagggttaggg | 21 |
| MUC1 | gctccaccgcccccccagcccacgg | 22 |
| MUC1 | cccccccagcccacggtgtcacctc | 23 |
| MUC1 | cccacggtgtcacctcggccccggac | 24 |
| MUC1 | cccgggctccaccgccccccagc | 25 |
| MUC4_exon | gtcaccgacacttcctcagcatccac agg | 26 |
| MUC4_exon | ccctcttcctgtcaccgacacttc | 27 |
| MUC4_exon | cctcagcatccacaggtcacgccac | 28 |
| MUC4_intron | gaaggtatgggtgtggaaggtatggg | 29 |
| MUC4_intron | gtgtggaaggtatggg | 30 |

Figure 3B:
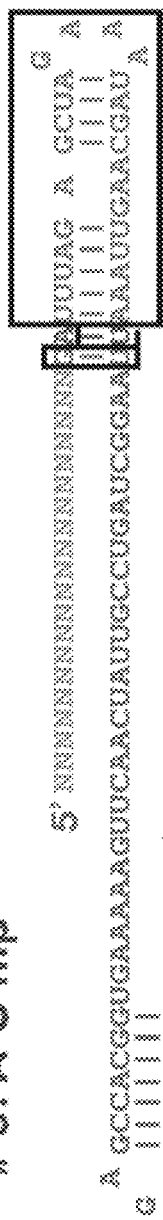
Figure 3B:
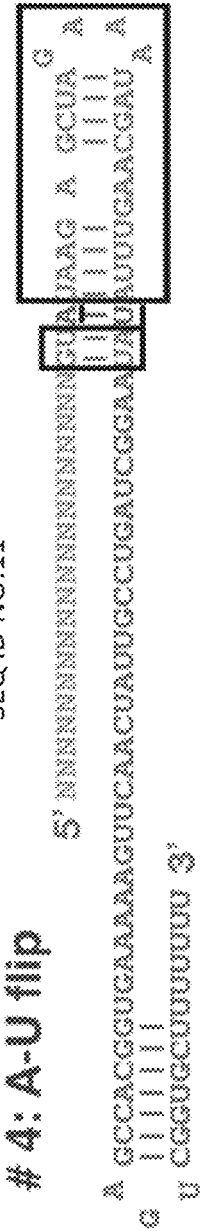
Figure 3B:
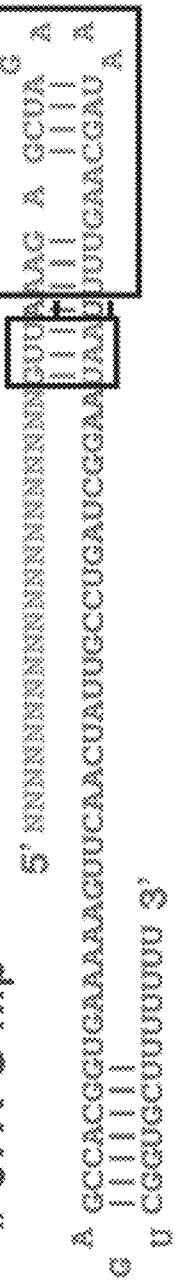
Figure 3B:
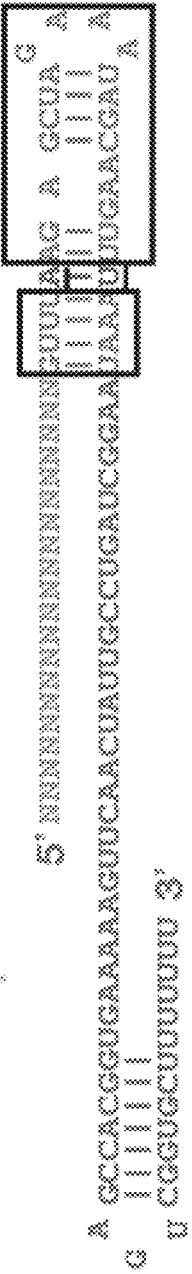
Figure 3C:
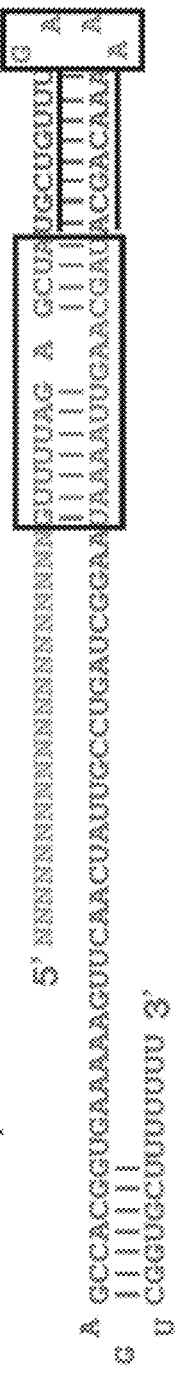
Figure 3D:
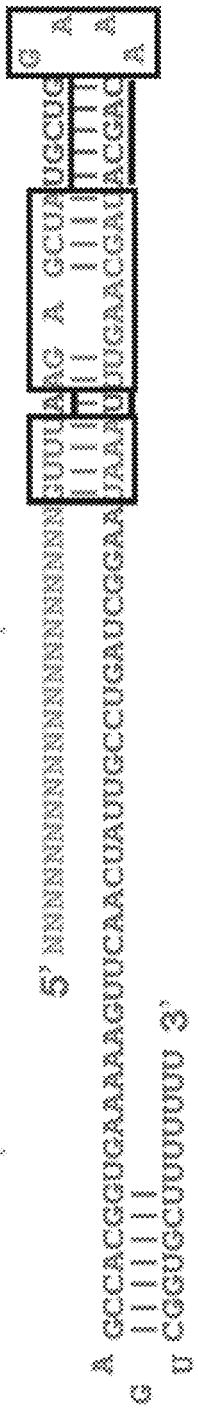
Figure 3D:
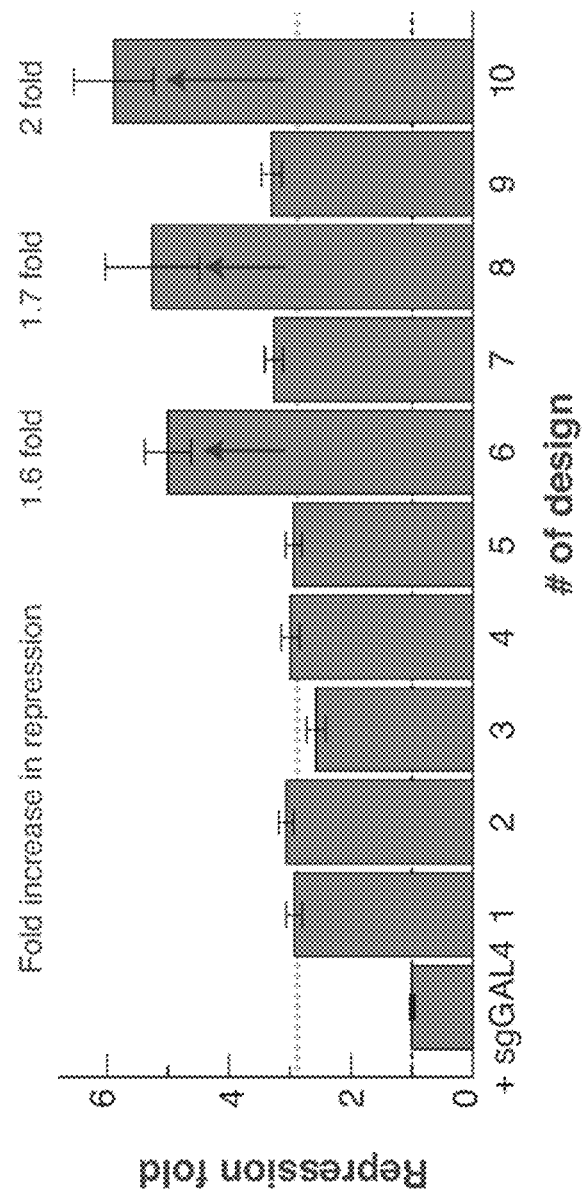

Previous work has suggested expression levels of the chimeric guide RNA limit CRISPR/Cas9 function in human cells. To improve the system for more effective genome imaging, we modified the sgRNA design to increase its expression level and assembly with the dCas9 protein. It has been shown that 4 or more consecutive uridine (U) residues could pause or terminate Pol-III transcription (Nielsen, et al., 2013). To improve the sgRNA expression levels, we removed the consecutive 4 U's by A-U base pair flipping or added a polymerase III SINE element polyadenylation signal sequence at the 3' end (FIG. 3A-C). We first tested these new sgRNAs using the CRISPR interference (CRISPRi) method (Qi, et al., 2013). We transfected each modified sgRNA targeted to an EGFP reporter into cells expressing stably EGFP and dCas9-KRAB as previously described. One A-U flip (#6) enhanced repressive activity. To improve the assembly of sgRNA and dCas9, we extended the stem-loop hairpin structure that binds to dCas9. A 5-bp extension at the top of the hairpin (#8) increased repressive activity. Interestingly, a design combining both modifications (#10) further increased the repression (FIG. 3A-C).

Figure 1E:
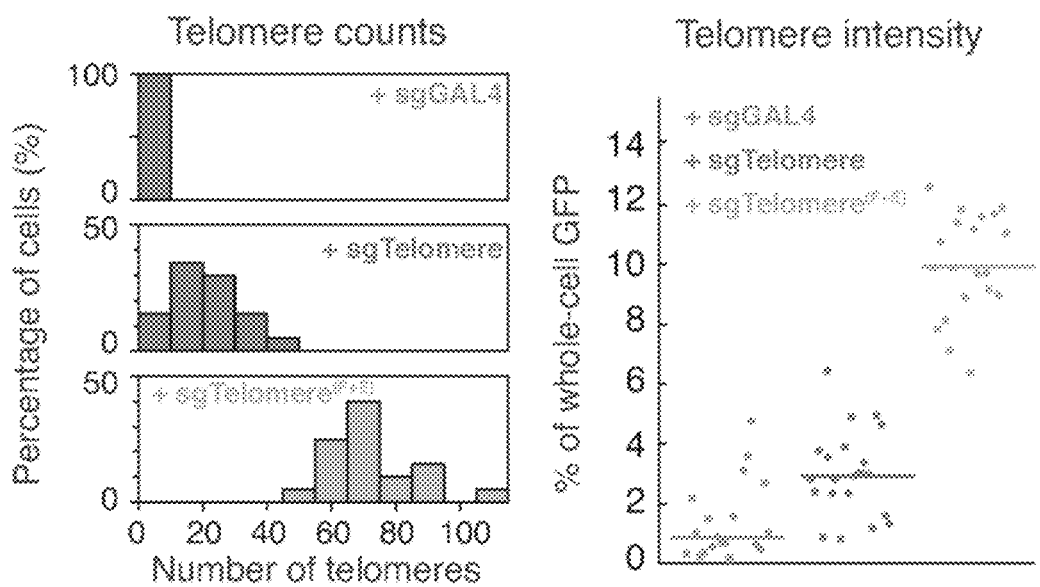
Figure 4B:
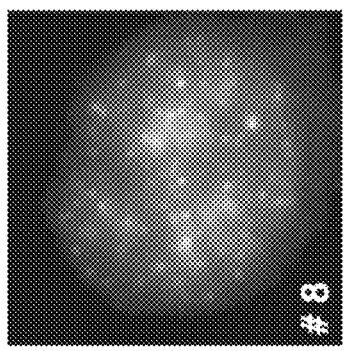
Figure 4B:
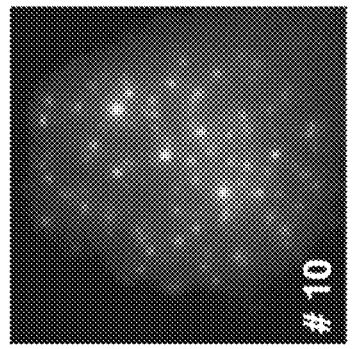
Figure 4B:
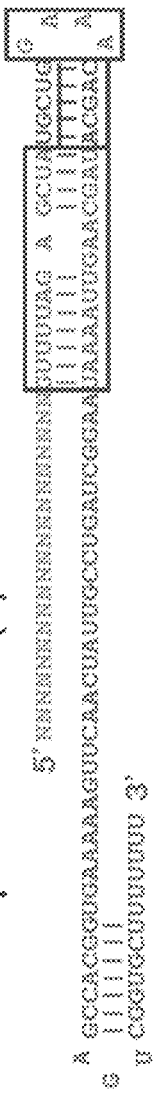
Figure 4B:
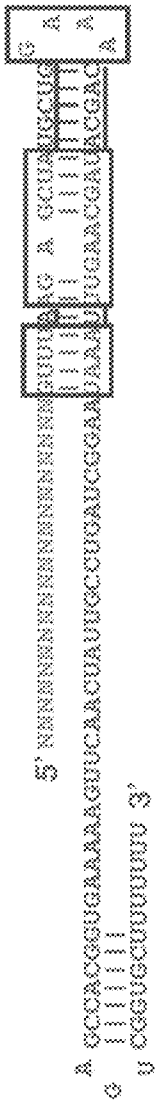
Figure 4C:
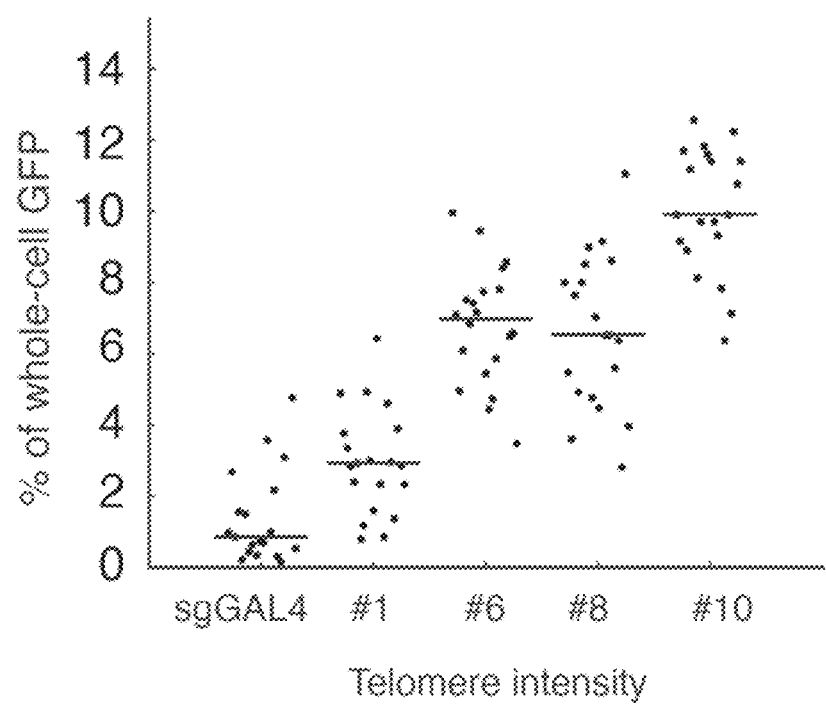
Figure 5:
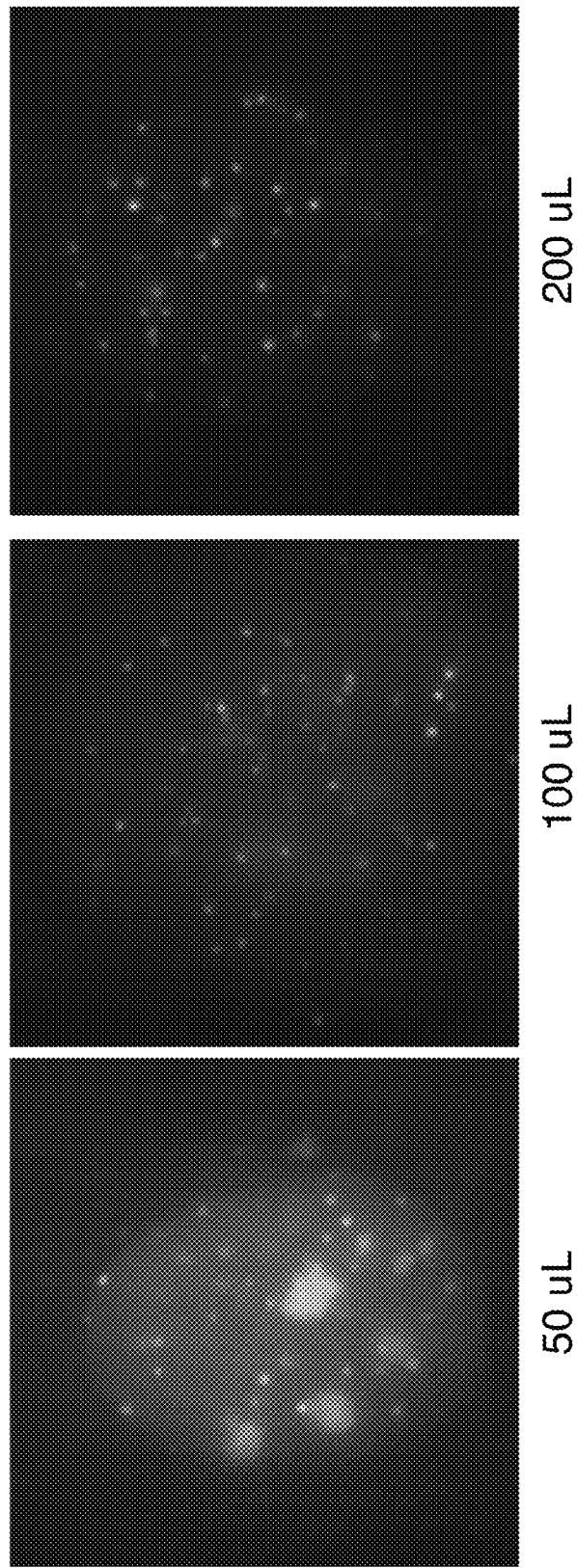
FIG. 5 Labeling efficiency of telomeres is dosage-dependent of the sgRNA lentivirus. With the best sgRNA design (F+E), telomeres were labeled when infected with 50 µL lentivirus, but there were some nucleolus-like structures highlighted in the background. Infection with 200 µL lentivirus increased telomere labeling efficiency without nucleolus-like structures, possibly due to enhanced assembly between sgRNAs and the dCas9-EGFP protein. A good balance between labeling efficiency and cytotoxicity was achieved by infecting the cells with 100 1.1.L sgRNA lentivirus.

We tested three improved sgRNA designs for telomere imaging. Consistently, these sgRNA designs increased puncta numbers and decreased background and nucleolar signals (FIG. 4A-C). The best design (F+E) combined both A-U flip and hairpin extension (FIG. 1C) and doubled the observable telomere numbers and increased the signal-to-background ratio by 5-fold (FIG. 1D & 1E). This sgRNA design also enabled robust imaging at lower lentiviral titers (FIG. 5).

Figure 6A:
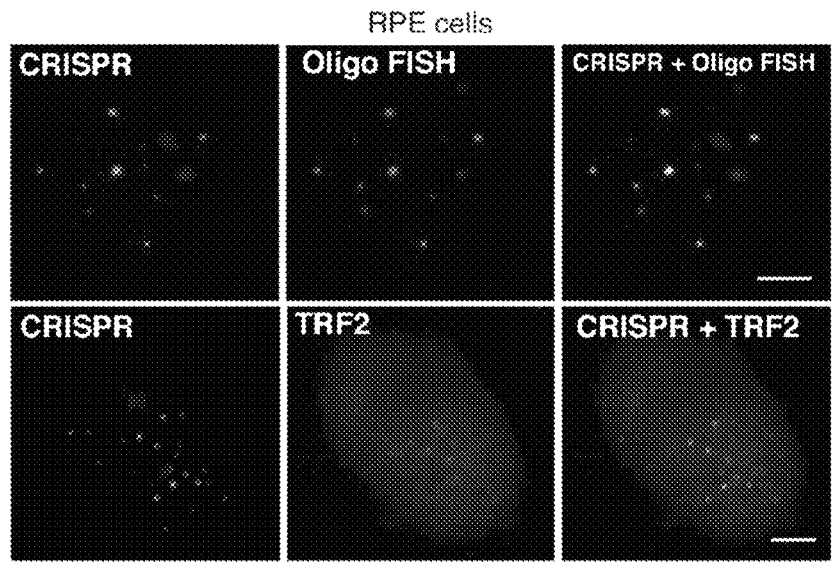
FIG. 6A-6C depict the co-localization of CRISPR labeling with telomere markers. CRISPR can effectively detect telomere length changes in living cells.
Figure 7A:
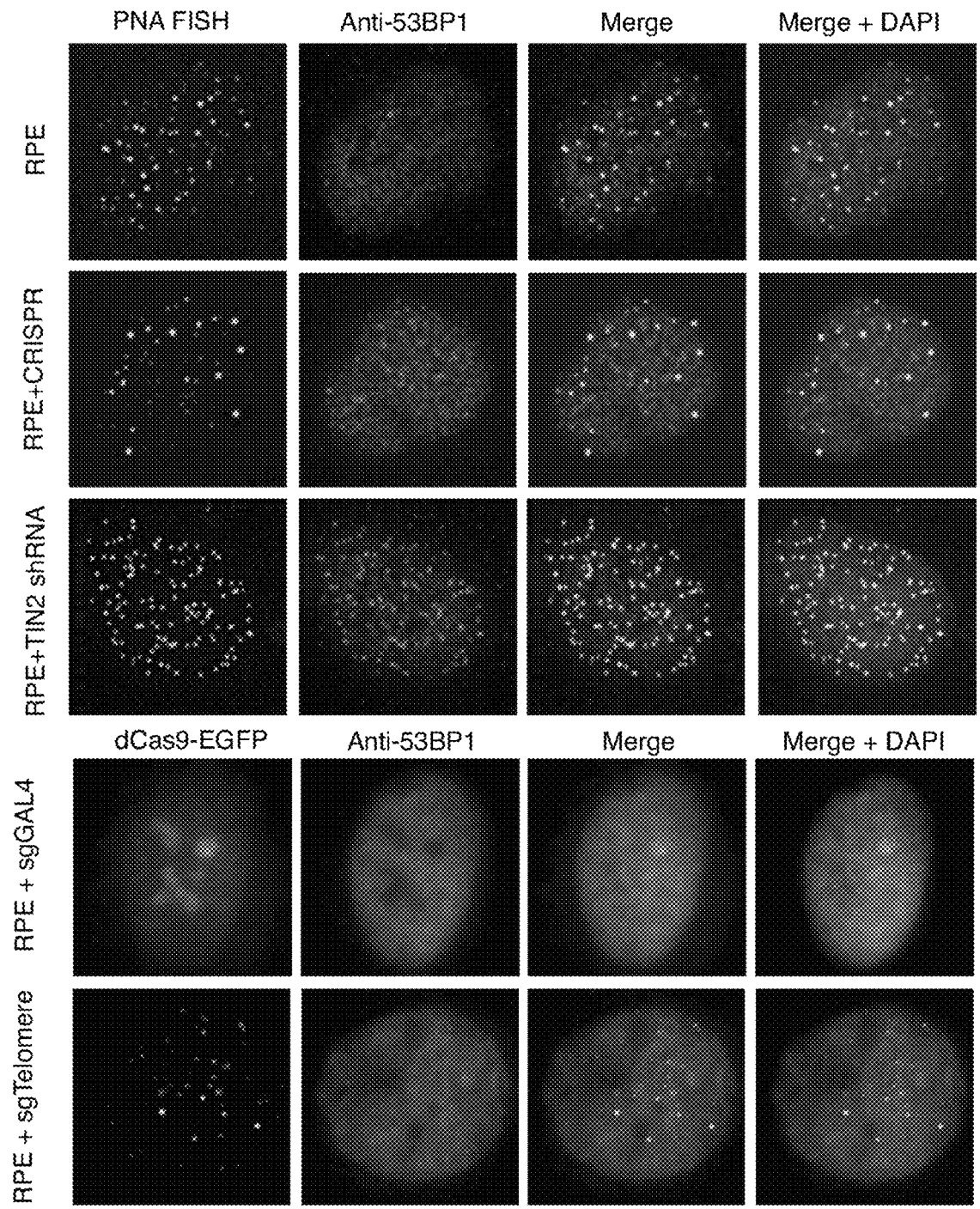
FIG. 7A-7B illustrate that no DNA damage response was detected at the telomeres labeled by CRISPR.
Figure 7B:
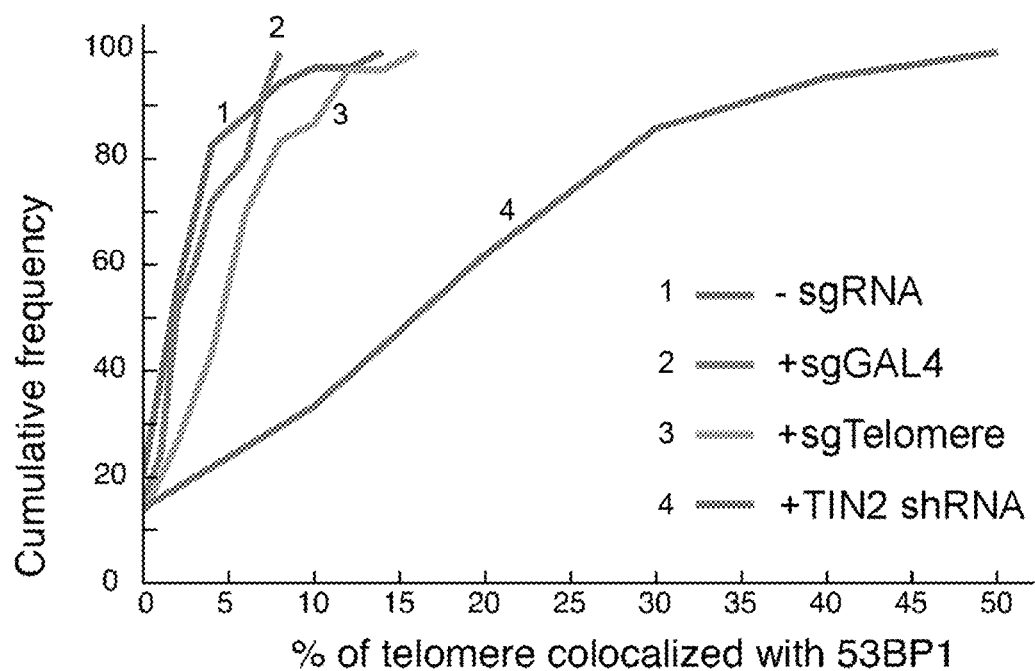

To verify that the observed puncta were indeed telomeres, we performed FISH using telomere-specific Cys5-labeled telomeric repeat oligo probes in CRISPR-labeled cells and observed spatial co-localization (FIG. 6A). We also used an antibody to stain endogenous TRF2 in CRISPR-labeled cells, which is a protein in the shelterin complex that binds to the telomeric DNA repeats (Griffith, et al., 1999). In all cells, TRF2punctaco-localized with CRISPR labeling. The co-localization of TRF2 and CRISPR puncta also suggests that dCas9 binding does not disrupt the telomere structure. To further check the integrity of telomeres with dCas9 binding, we used an antibody to image the localization of 53BP1, a protein recruited to damaged DNA sites(d'Adda di Fagagna, et al., 2003). We saw a very mild increase in DNA damage at telomeres, which was orders of magnitude less than major telomere disruptions such as disassembly of the shelterin complex by shRNA-mediated depletion of TIN2 (FIG. 7A-7B) (Kim, et al., 1999).

Figure 6B:
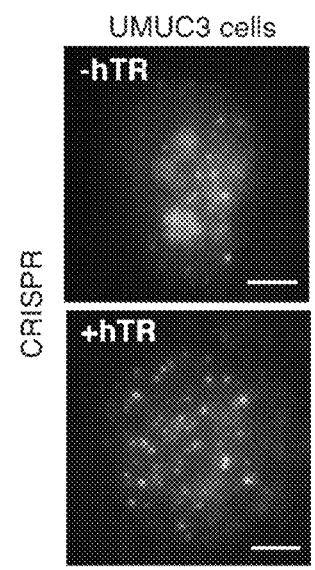
Figure 6C:
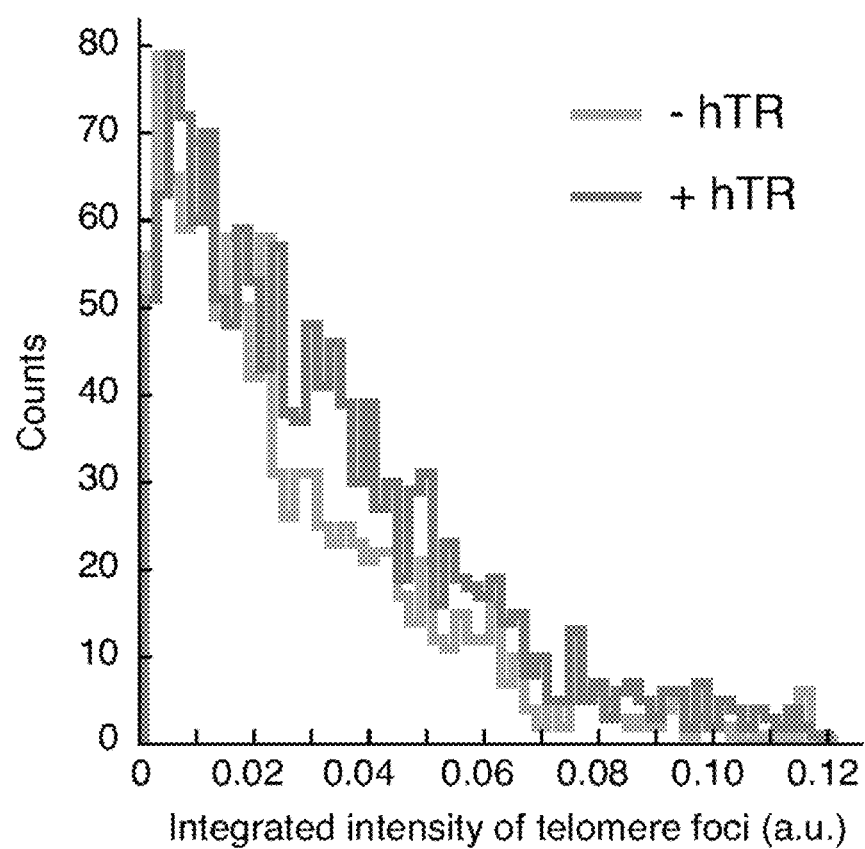

To examine whether the puncta intensity in CRISPR imaging correlates with telomere length, we imaged telomeres in theUMUC3human bladder caner cell line, wherein telomere length can be conditionally elongated by transfection with a human telomerase RNA (hTR) gene (Vaziri, et al., 1998). Six days after hTR lentiviral infection, we compared UMUC3 cells with and without transduction. CRISPR imaging showed brighter signals with hTR, consistent with the expected increase of the telomere length (FIG. 6B & 6C). Our results suggest that CRISPR imaging can detect telomere length changes by measuring fluorescence intensity.

Figure 8A:
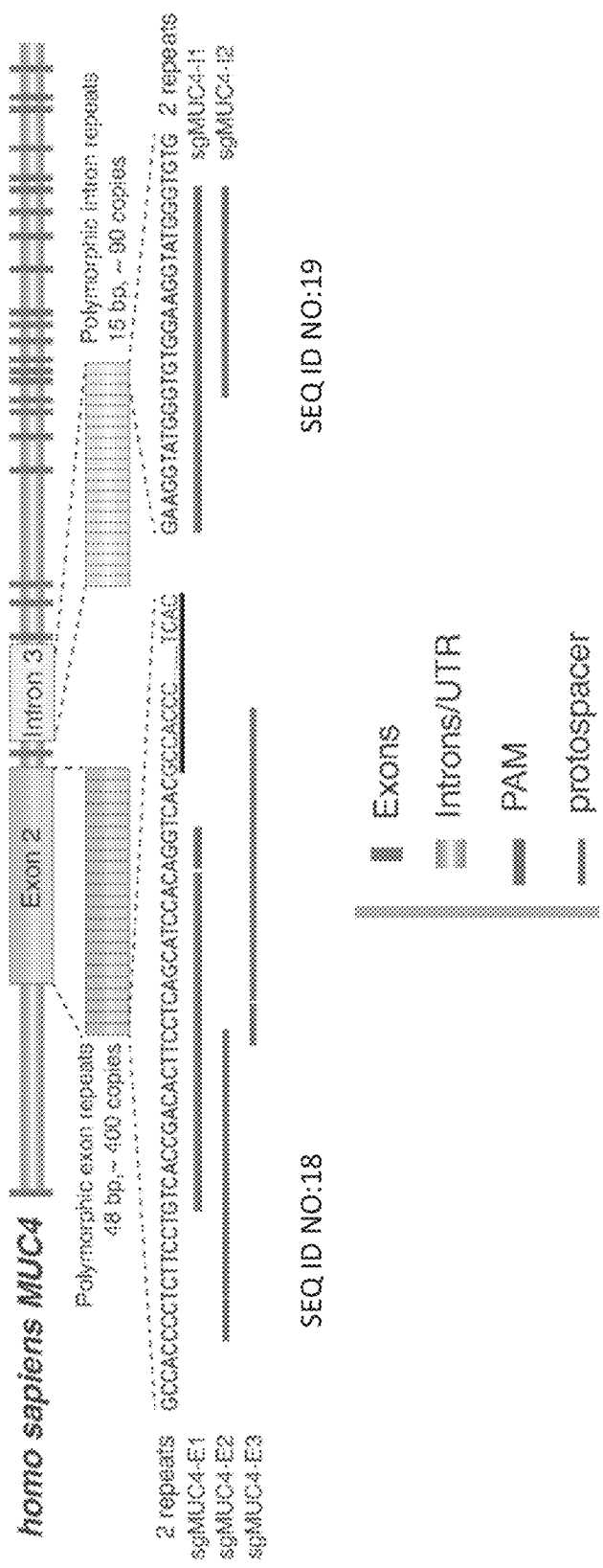
Figure 8B:
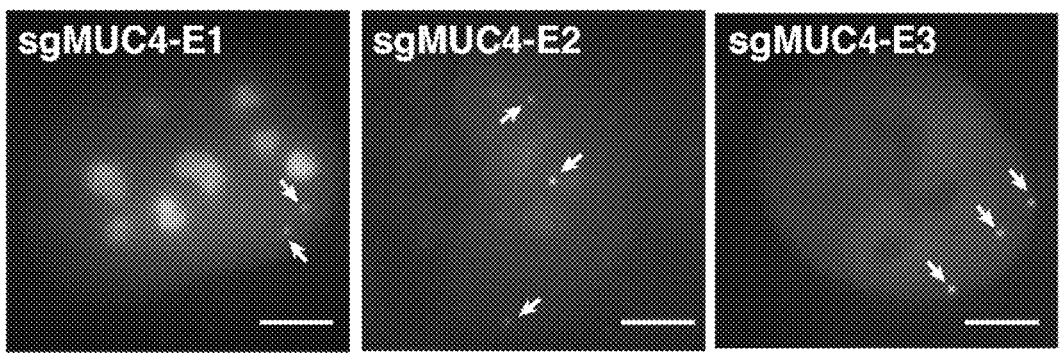
(FIG. 8B) Conventional fluorescence images of MUC4 loci (arrows) in RPE cells by targeting the exon 2 repeats with three different sgRNAs.
Figure 8C:
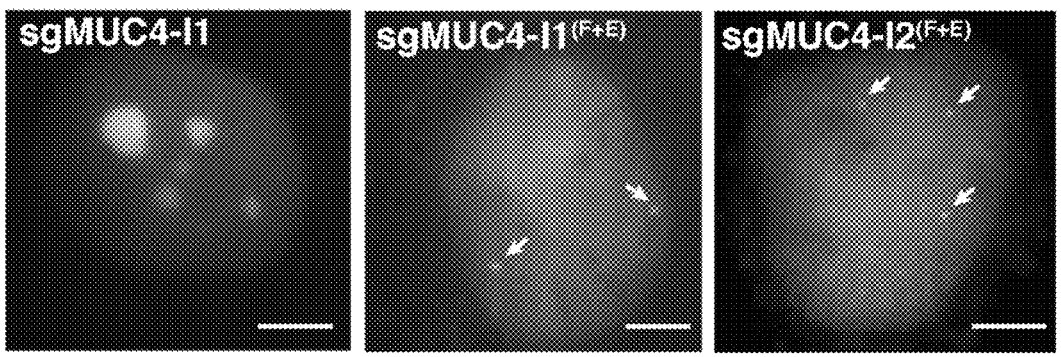
(FIG. 8C) Two protospacers with different lengths, 13 bp and 23 bp, were chosen as targets in the intron repeats. MUC4 intron (arrows) can only be labeled by using optimized sgRNA design when targeting the 23 bp protospacer.

Next, we used CRISPR to image endogenous protein-coding genes. Specifically, we chose the MUC4gene which encodes a glycoprotein important for protecting mucus in diverse epithelial tissues and tumor formation (Hollingsworth, et al., 2004). The MUC4 gene contains a region in the coding sequence with a variable number (>100) of 48-bp tandem repeats in the second exon (FIG. 8A) (Nollet, et al., 1998). To image the MUC4 gene, we designed three sgRNAs (Table 1) targeting this repeat sequence (sgMUC4-E1, E2, E3). We observed that the labeling efficiency depended on the target site. The best one, sgMUC4-E3, showed labeling of 2 or more puncta in 100% of cells (FIG. 8B). The labeling was highly efficient, and the original sgRNA design without modifications was sufficient for imaging. The MUC4 gene also contains an array of 15-bp tandem repeat region in the third intron. As previous studies have shown that sgRNA binding requires a minimal ~12-bp DNA complementary region, we designed two sgRNAs with different lengths of base pairing (23 bp and 12 bp) to the repeat sequence (Table 1). In this case, the F+E modifications of the sgRNA designs greatly enhanced the imaging efficiency (FIG. 8C). Surprisingly, although the binding affinity of the shorter 12-bp sgMUC4-I2 is predicted to be lower than that of the longer 23-bp sgRNA (Qi, et al., 2013), sgMUC4-I2 showed a higher imaging efficiency. This implies that the copy number of bound sgRNA-dCas9-EGFP is more important than the binding affinity of individual sgRNAs.

Figure 8D:
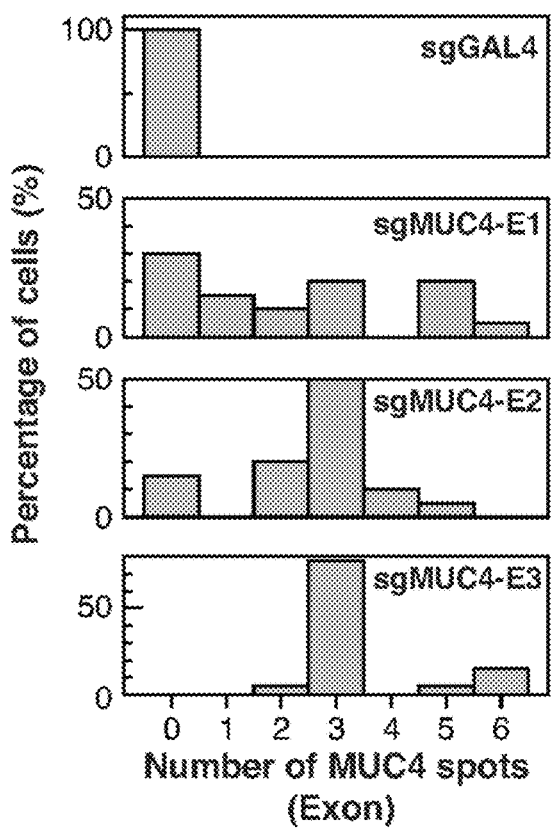
(FIG. 8D) Histograms of MUC4 loci counts by labeling exon 2 via CRISPR.
Figure 8E:
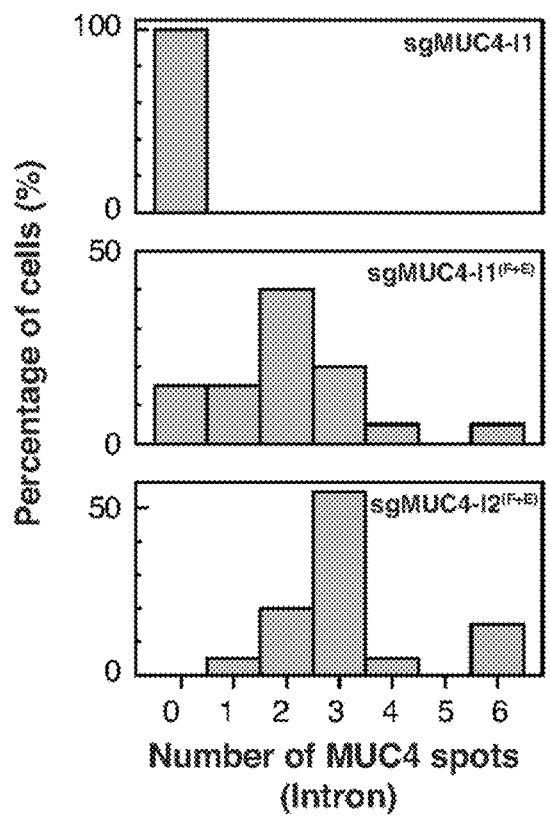
(FIG. 8E) Histograms of MUC4 loci counts by labeling intron 3 via CRISPR.
Figure 8F:
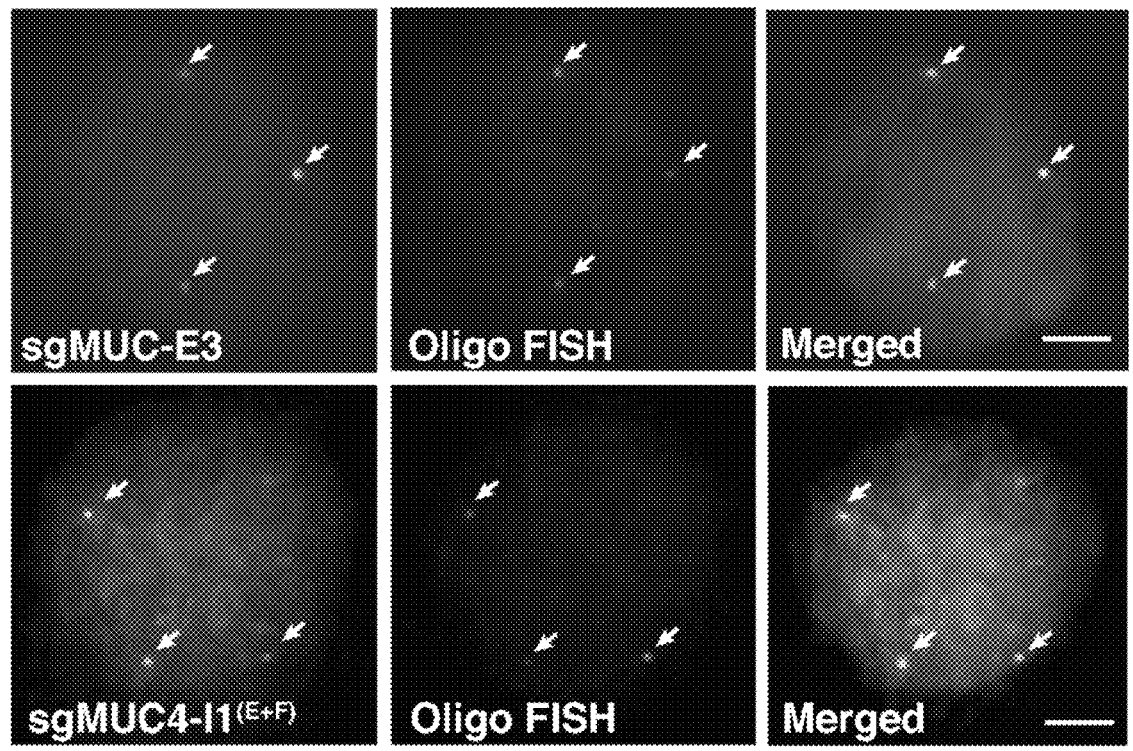
(FIG. 8F) Co-localization of dCas9-EGFP and Oligo FISH probes for both exon and intron labeling.
Figure 9A:
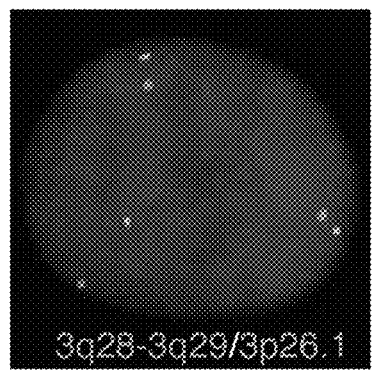
FIG. 9A-9B depict the results of a karyotype analysis of the RPE cell line. Cytogenetic analysis was performed on ten G-banded metaphase cells of human RPE cell line. The chromosomes were stained with dyes that show a pattern of light and dark bands (called the banding pattern). The banding pattern for each chromosome was specific and consistent allowing identification of each of the 24 chromosomes. 10 cells were analyzed. This cell line demonstrated a hypertriploid karyotype (73 chromosomes in total) with female origin. There were extra copies of chromosome 5, 7, 11, 12, 16, 19, and 20 that were present in eight or nine cells except for chromosome 16 (six cells) and 19 (four cells). Chromosome 10 and 22 were also lost in nine and eight cells respectively. All ten cells had two copies of an abnormal X chromosome with addition of unidentifiable genetic material translocated to the long-arm at Xq28.
Figure 9B:
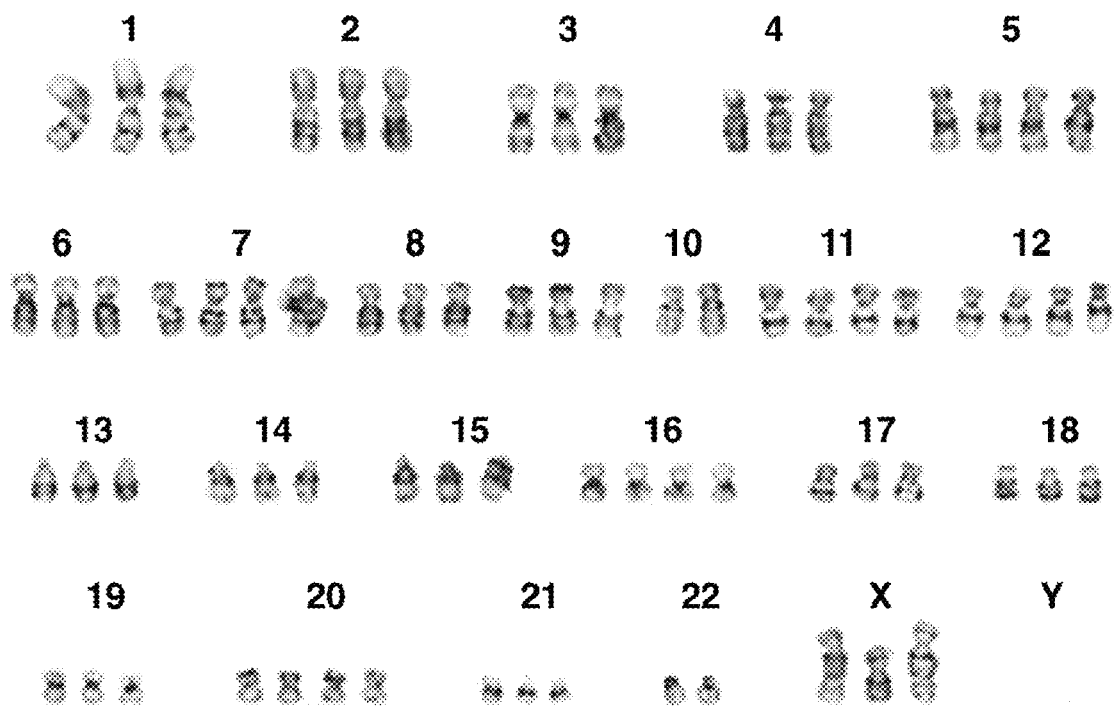

Interestingly, we saw 3 labeled MUC4 loci in the majority of RPE cells using both methods. As the MUC4 gene is located on chromosome 3, we measured the ploidy of our cells using FISH targeting two different regions on chromosome 3 as well as whole-cell karyotype analysis (FIG. 9A-9B). Our results confirmed that the RPE cell line that we used is trisomic for chromosome 3, suggesting that using the CRISPR for imaging is capable of detecting gene copy numbers in living cells. While we saw 1 to 2 puncta using oligo FISH, CRISPR imaging using sgRNAs targeting the MUC4 exon showed statistically more puncta. The best one, sgMUC4-E3, showed 3 or 6 labeled spots in 90% of the cells (FIG. 8D), implying all possible sites were labeled. The observation of 6 spots is likely due to chromosome replication. CRISPR labeling with two sgRNAs targeting the MUC4 intron gave similar results (FIG. 8E). To confirm the observed puncta labeled with sgMUC4-E3 were indeed MUC4 loci on different chromosomes, we performed Cys5-labeled Oligo FISH labeling and observed all three spots were co-labeled (FIG. 8F & Table 2).

TABLE 2

Oligo FISH probes

| Targets | Oligo FISH probe | SEQ ID NO |
|---|---|---|
| Telomere | Cy3-ttagggttagggttagggttaggg | 31 |
| Telomere | Cy5-ttagggttagggttagggttaggg | 32 |
| MUC1 | Cy3-agcccacggtgtcacctcgg | 33 |
| MUC1 | Cy5-acctcggcccoggaca | 34 |
| MUC4_exon | Cy3-tcttcctgtcaccgacactt | 35 |
| MUC4_exon | Cy5-cttcctgtcaccgac | 36 |
| MUC4_intron | Cy3-aggtatgggtgtgga | 37 |
| MUC4_intron | Cy5-aggtatgggtgtgga | 38 |

Figure 10A:
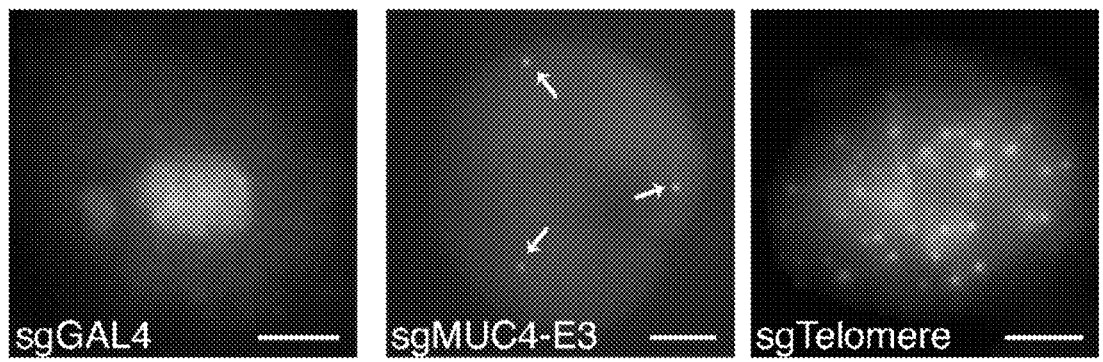
FIG. 10A-10C depict CRISPR imaging of MUC4 and telomeres in the monoclones of HeLa cell line.
Figure 10B:
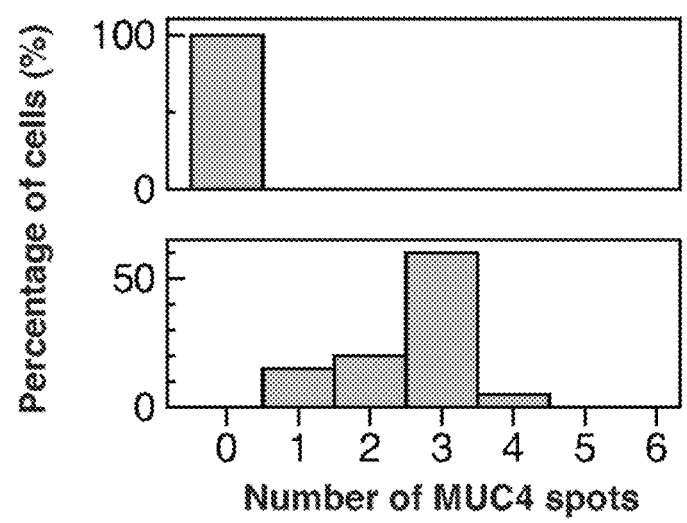
Figure 10C:
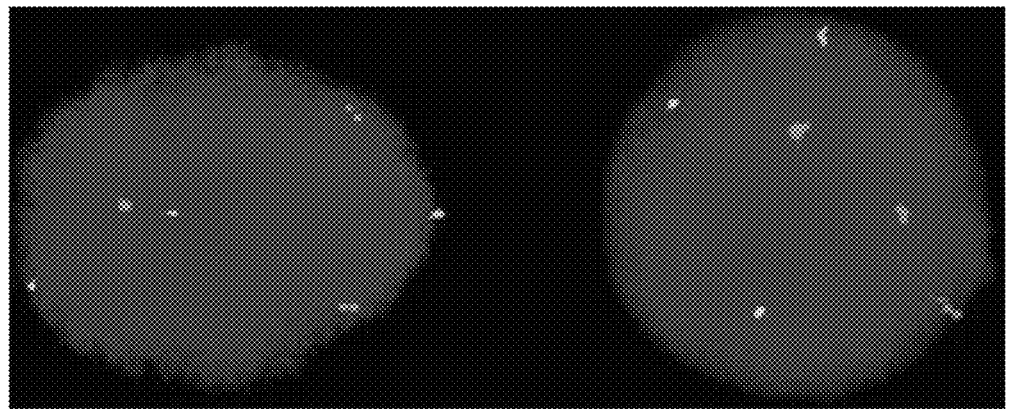
Figure 11A:
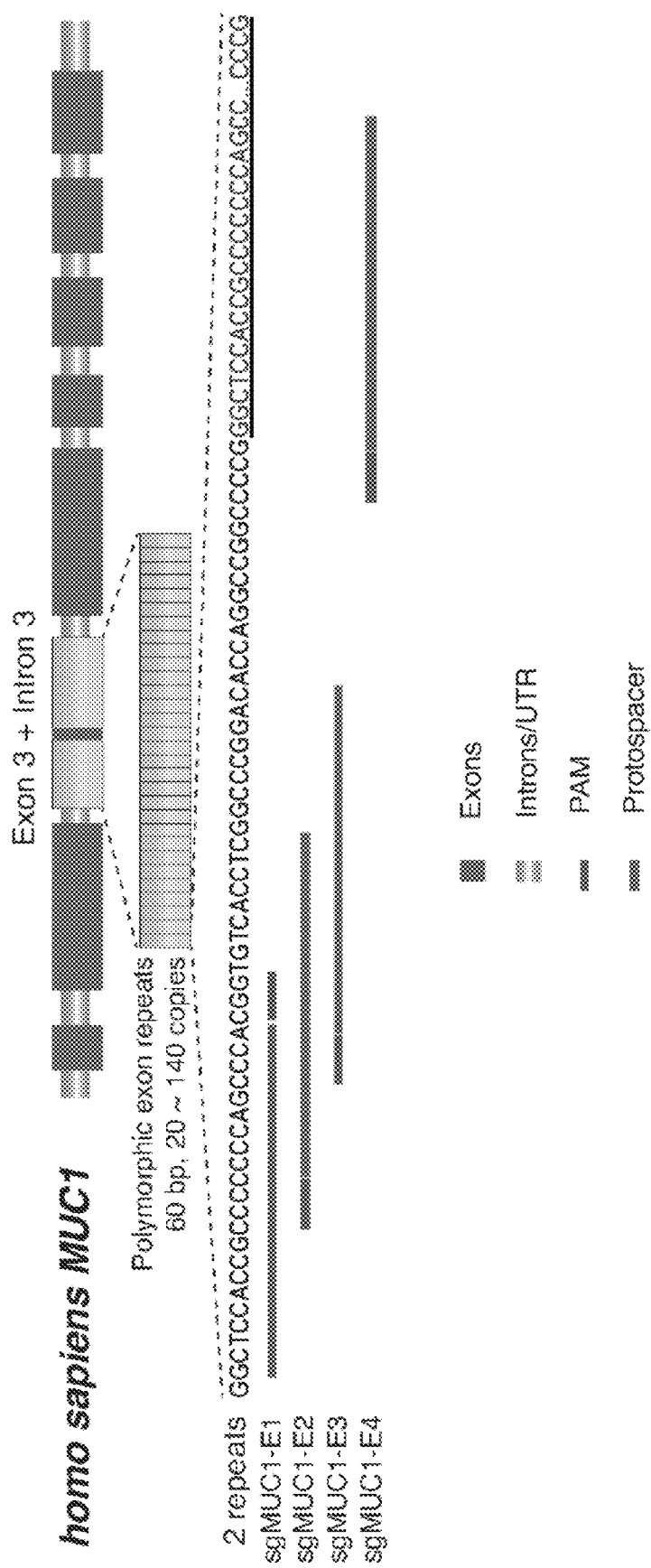
FIG. 11A-11D depict CRISPR imaging of MUC1 loci in living RPE cells.
Figure 11B:
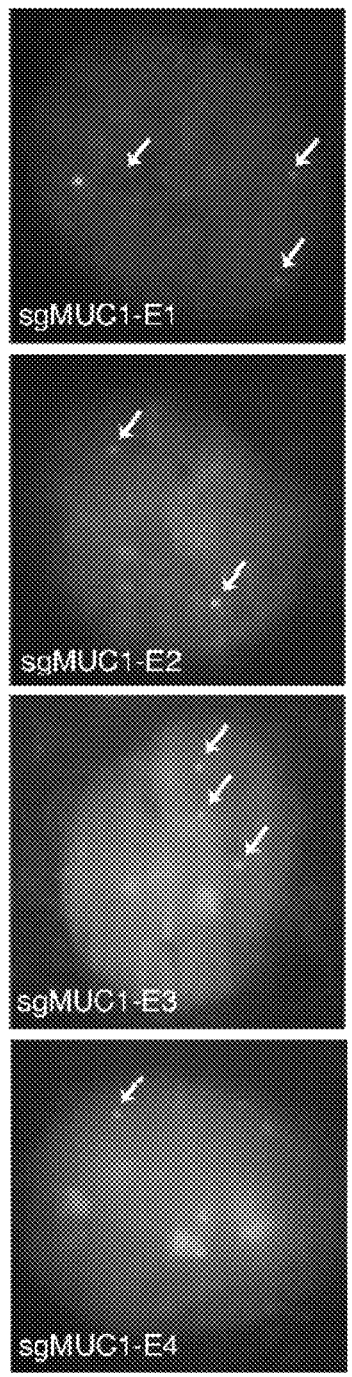
Figure 11C:
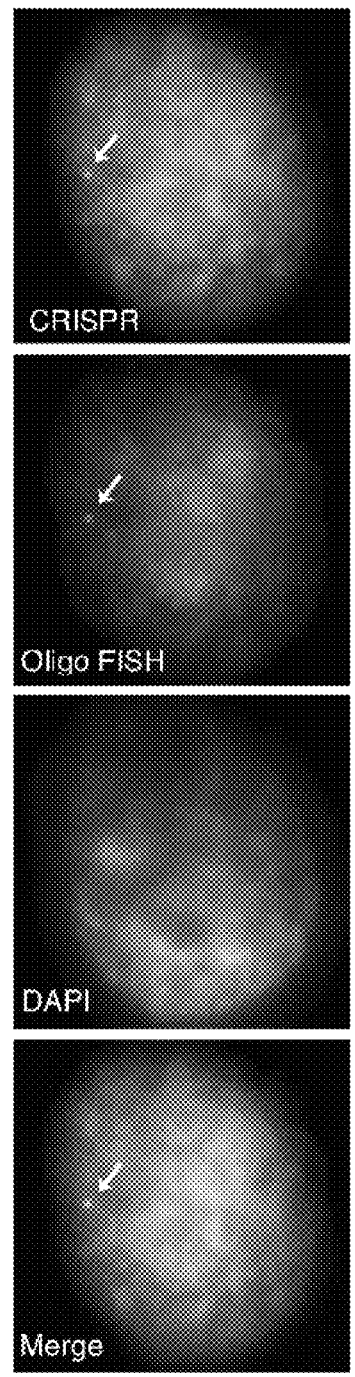
Figure 11D:
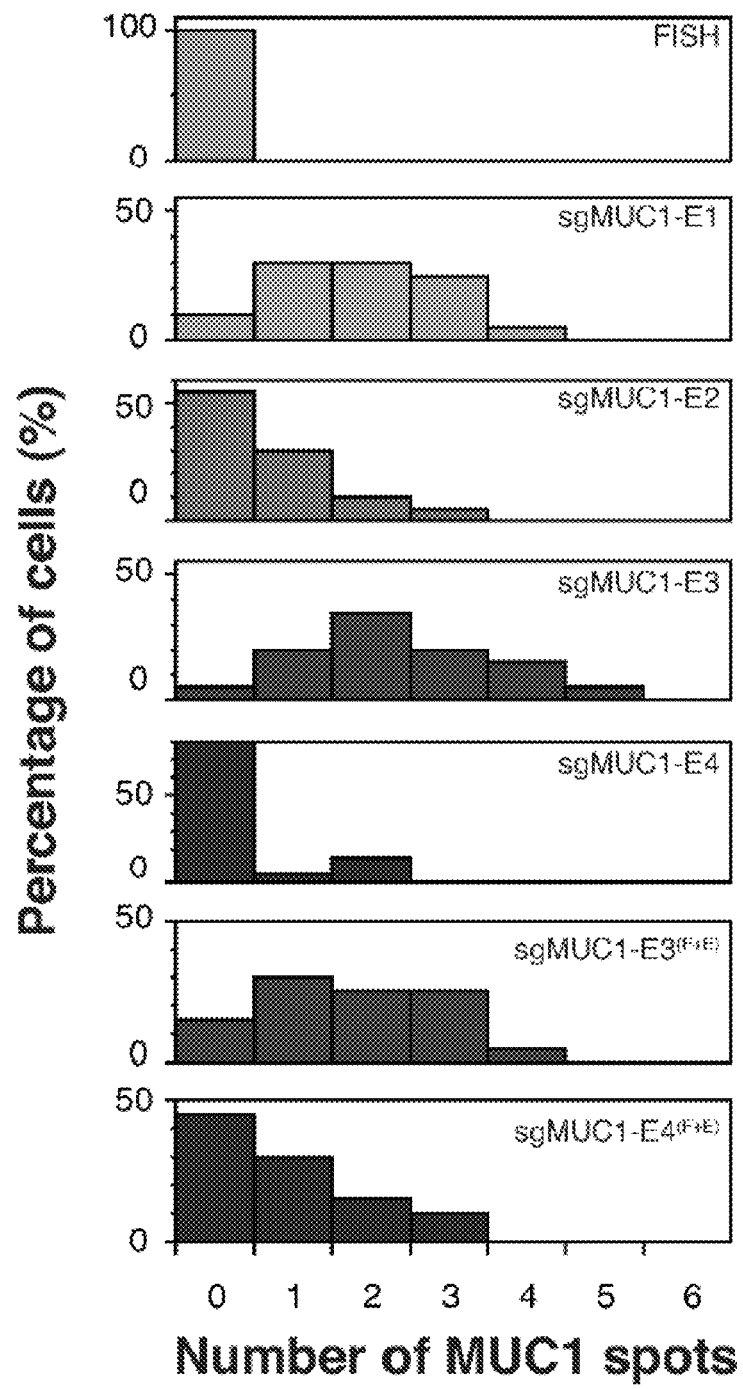
Figure 12A:
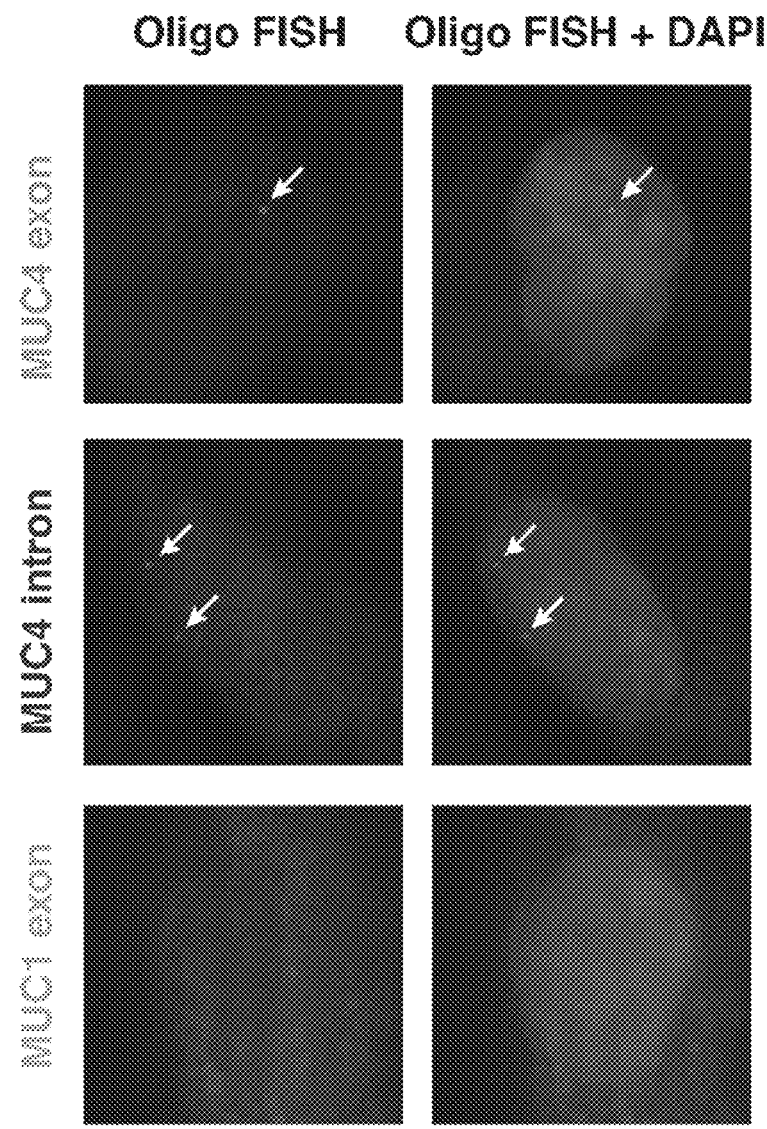
FIG. 12A-12B depict a comparison of labeling efficiency between CRISPR and Oligo FISH.
Figure 12B:
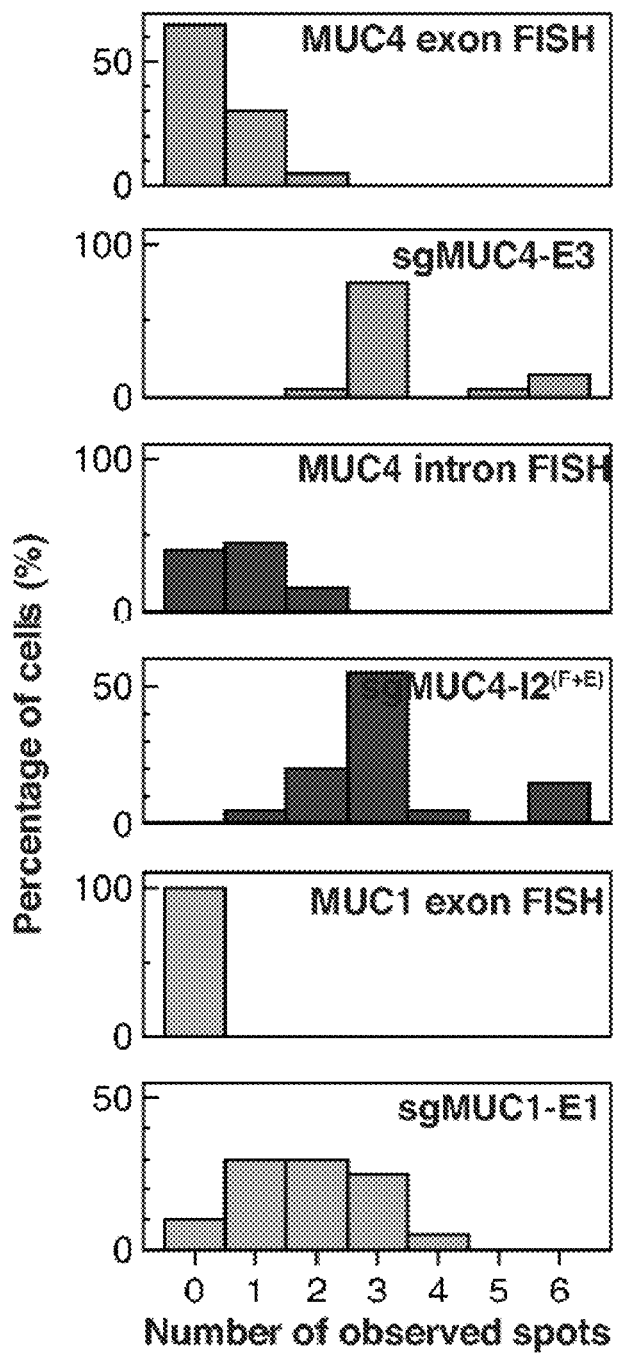
Figure 13A:
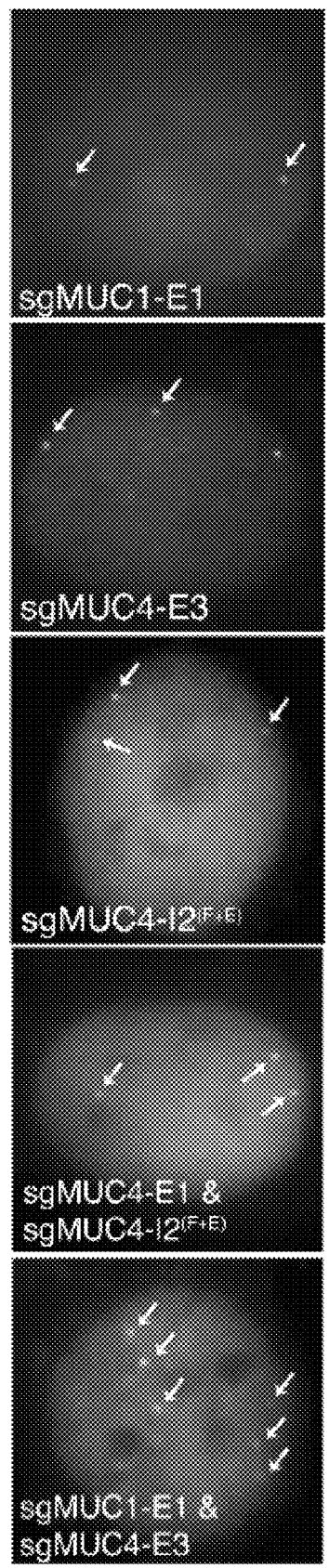
FIG. 13A-13B depict imaging of multiple elements via CRISPR.
Figure 13B:
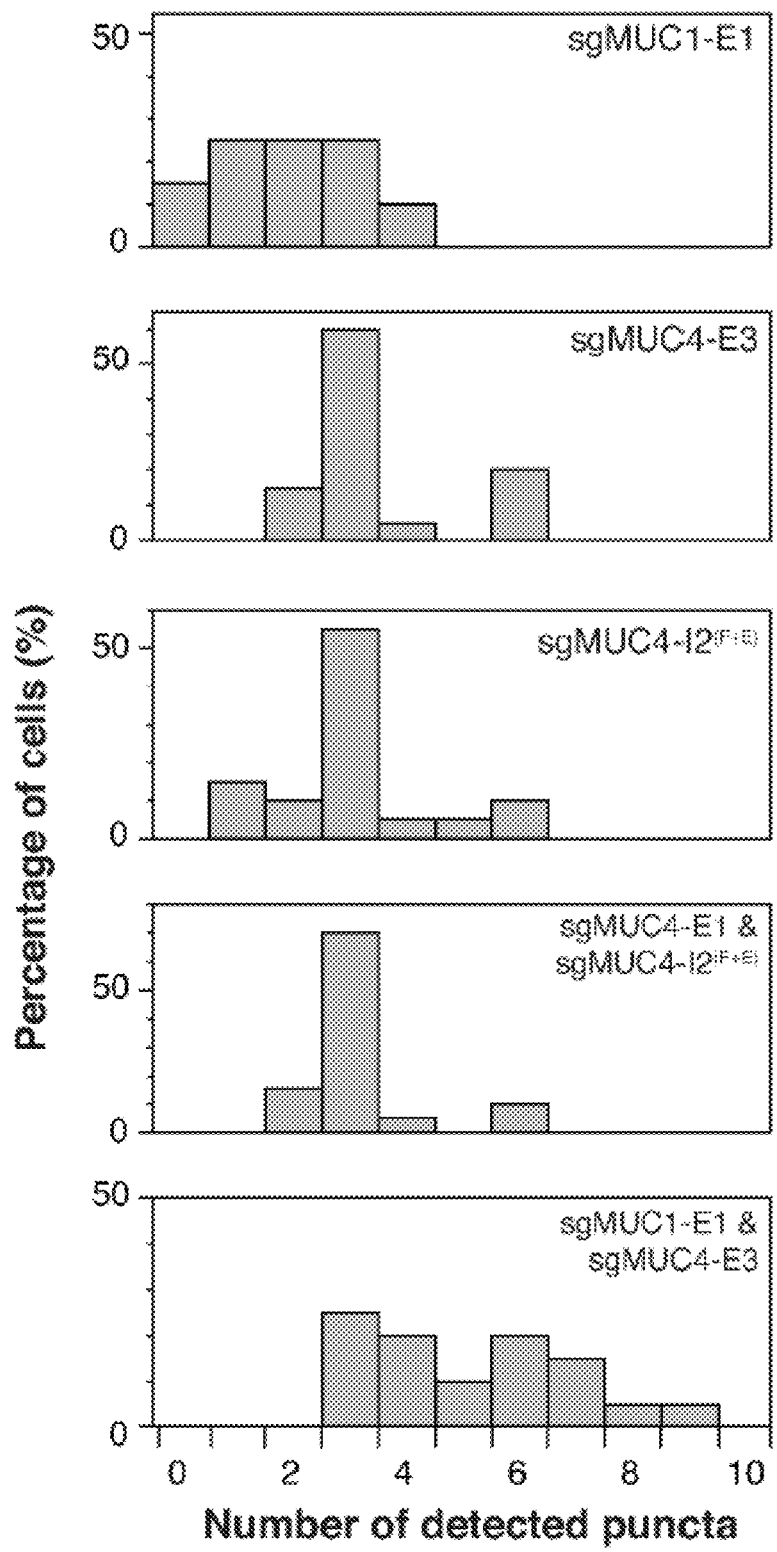

To verify the generality of CRISPR imaging, we used sgTelomere and sgMUC4-E3 to image MUC4 loci and telomeres in HeLa cells. In both cases, we observed strong labeling of the target genomic loci (FIG. 10A-10C). We similarly observed three copies of MUC4 in our HeLa cells, and FISH experiments further confirmed the cells contain a trisomy of chromosome 3. We also designed sgRNAs to target the repetitive elements in the MUC1 gene (FIG. 11A-11D & Table 1) (Gendler, et al., 1990). We observed distinct multiple MUC1 loci in the RPE cells, which was further confirmed by co-labeling with FISH. It is worth noting that CRISPR generally exhibits a higher labeling efficiency than using Oligo FISH (FIG. 12A-12B).

Figure 8G:
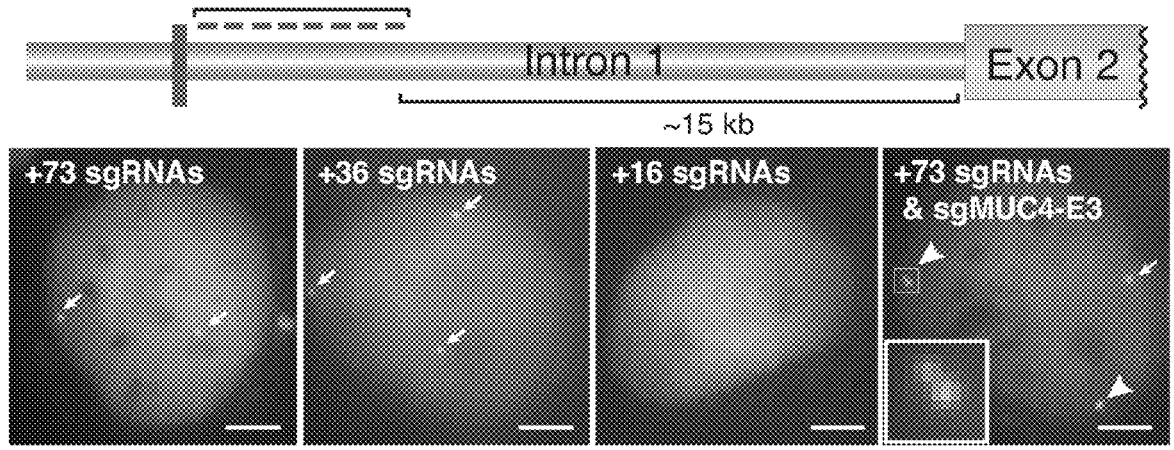
(FIG. 8G) 73 protospacers in the first exon were selected for labeling the non-repetitive region of MUC4 gene. 1-3 spots (arrows) can be detected with 36 and 73 sgRNAs. Co-labeling of MUC4 using 73 sgRNAs and sgMUC4-E3 shows two proximal spots (arrowhead). The inset shows the magnification of the white box region.
Figure 8H:
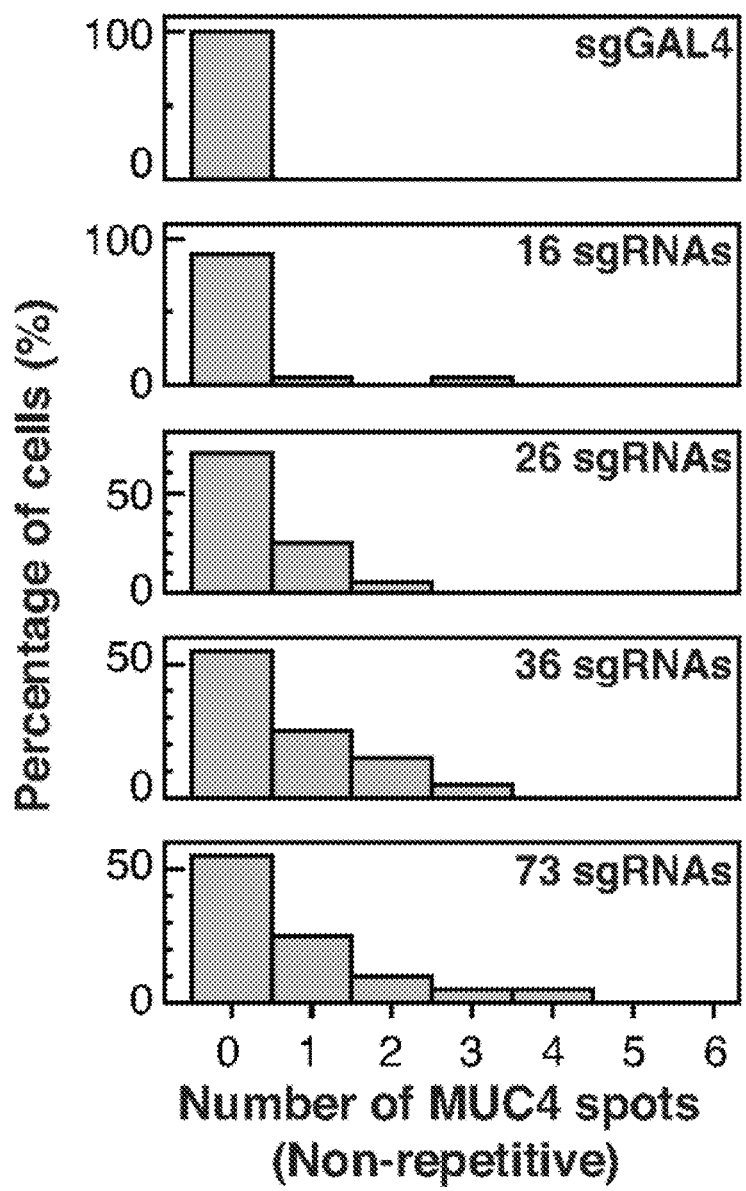
(FIG. 8H) Histograms of MUC4 loci counts. 26 sgRNAs or more are required to detect the non-repetitive genome loci. Scale bar, 5 µm.

Most genes and genetic elements in the human genome contain non-repetitive sequences. To test if CRISPR labeling could detect non-repetitive genetic elements, we designed 73 sgRNAs that target both DNA strands spanning a 5-kb region in the first intron of MUC4 gene (Table 3). We produced lentiviral cocktails, each containing 5 to 6 sgRNAs, and infected different numbers of sgRNAs (16, 26, 36 or 73) into RPE cells while maintaining the same total virus dosage. We observed 1 to 3 MUC4 loci using 36 or 73 sgRNAs, but no detectable puncta when using 16 sgRNAs (FIGS. 8G & 8H). This suggests that to detect a non-repetitive genome sequence locus using CRISPR, currently 30 or more sgRNAs are required.

TABLE 3

Protospacer sequences in the MUC4 non-repetitive region for CRISPR imaging, highlighted in bold, PAM

| sg RNA | Protospacer sequences | Seq Id No: |
|---|---|---|
| 1 | gaagagtggaggccgtgcgcggtgg | 39 |
| 2 | aggcaggagatcacctgaggtcagg | 40 |
| 3 | ccccgtctctactaaatatac | 41 |
| 4 | ccccacctgtaattccagctactc | 42 |
| 5 | cctgggaggtggaggttgcagtgagc | 43 |
| 6 | cctgggagagagagcgagactctgtc | 44 |
| 7 | gaagaggagaaaagtggggaagagg | 45 |

TABLE 3-continued

Protospacer sequences in the MUC4 non-repetitive region for CRISPR imaging, highlighted in bold, PAM

| sgRNA | Protospacer sequences | Seq Id No: |
|---|---|---|
| 8 | gaacagagggccagagagcagcccgg | 46 |
| 9 | cccaggcttactcgcagagagaaagac | 47 |
| 10 | gtacaccttgtgtacagagctggg | 48 |
| 11 | gaaaactcatgtaaagctgcaggg | 49 |
| 12 | gcaagcaagggaagcgacaaggagg | 50 |
| 13 | ggaggcggccagggcgcagaggg | 51 |
| 14 | cctctgagctcgggtttaaaagc | 52 |
| 15 | gtagccccggcattggccttggg | 53 |
| 16 | gcctgtgggagatgttccctcggg | 54 |
| 17 | ccaggctgtccctctggcttcaggac | 55 |
| 18 | gagtctttgggggagagtctggg | 56 |
| 19 | gctcctgccctgcctctcagcagg | 57 |
| 20 | gcatatttgaggagcttcctggg | 58 |
| 21 | ggctgcaagagaagccatgctgg | 59 |
| 22 | gatgtttcaggactaggctgaggg | 60 |
| 23 | ccctacacctccccacccctccagc | 61 |
| 24 | cccgctccagtgctcatcccacc | 62 |
| 25 | gccctgcagatgtggttgaagg | 63 |
| 26 | gaggctggggcttgggcgccggg | 64 |
| 27 | gtctttgccgtgaactgttctgg | 65 |
| 28 | cccgtgtctccccagggccccggtc | 66 |
| 29 | gctggacactcagctccatgtgg | 67 |
| 30 | gagcgcagaggggcaagacctggg | 68 |
| 31 | gagaaggagtgaaggactgttgg | 69 |
| 32 | cccgaagaagctaggcatgtcgtggagc | 70 |
| 33 | gagctgggccaggagaggagatgg | 71 |
| 34 | gaccgggcatgaccagggccttgg | 72 |
| 35 | gggcagcccccacccccacaggg | 73 |
| 36 | gttccttttggctccctgaagggg | 74 |
| 37 | gggtctgtagcacacttgccgg | 75 |
| 38 | gcccaggccagaggaaaaacacaggg | 76 |
| 39 | gtttccttaaggaacagccctgg | 77 |
| 40 | gcagacagaggtgggctagacaagg | 78 |
| 41 | gccccaggcaggaatgactcagaagg | 79 |
| 42 | ccacaggggaaaggcaactgggtc | 80 |
| 43 | gaccccagggaggtgacaggctgg | 81 |

TABLE 3-continued

Protospacer sequences in the MUC4 non-repetitive region for CRISPR imaging, highlighted in bold, PAM

| sgRNA | Protospacer sequences | Seq Id No: |
|---|---|---|
| 44 | gccacagcgcactccacggggaaggg | 82 |
| 45 | ggtctatctgtcagtctgggacagg | 83 |
| 46 | ccaaaactctccacagacccctc | 84 |
| 47 | gtccagcatcagcgacgcccttgg | 85 |
| 48 | ccttttggctctggagtcttaggc | 86 |
| 49 | gctactacgtagggttgtcatgagg | 87 |
| 50 | gtaaagtagaaaaggcataaaggg | 88 |
| 51 | cccagcacwiggaggcccaggc | 89 |
| 52 | ccagcttggccaaccctgtctccac | 90 |
| 53 | cctgggaggcagaggttgcagggagc | 91 |
| 54 | ccataaagacgtgtttgagaaagaggc | 92 |
| 55 | gaacccggaatggcacttgtgtcggg | 93 |
| 56 | cctcgtgcctctaaaaagccacc | 94 |
| 57 | ggcttggtgtattcagaatgtgg | 95 |
| 58 | cctggcagaggctggcctggcagtgc | 96 |
| 59 | gctaaggacaagaggcaatgagagg | 97 |
| 60 | ccccagcatgttctgagaaattgagtc | 98 |
| 61 | gacagagtttctctctgtcccccagg | 99 |
| 62 | ggggtttcaccatgttggccagg | 100 |
| 63 | gctcgcctcggctcccaaagtgctgg | 101 |
| 64 | gggcatttgtgttgcacgtgagg | 102 |
| 65 | cctgggttgcccgcagctccactc | 103 |
| 66 | gtagagatgccgccccgcccagg | 104 |
| 67 | gtccagtggccagtggattttggg | 105 |
| 68 | gaggcagctgggactagaacccagg | 106 |
| 69 | ccaaaccagcccagcccaccgac | 107 |
| 70 | ccctgctgagacagccattcattc | 108 |
| 71 | gaaacagacgtggcccagtctcttgg | 109 |
| 72 | gctgagagctgcatttcgaatgg | 110 |
| 73 | gacaagtcaggaagggccctgtgagg | 111 |

We also co-labeled the MUC4 locus using 73 intron-targeting sgRNAs and the exon-targeting sgMUC4-E3. The distance between the two labeling sites is 15-kb. In 20% of cells, we observed two proximal spots co-localized together (FIG. 8G), whose distance likely reflects the local organization of the chromatin structure. Furthermore, we co-labeled both MUC1 and MUC4 using two sgRNAs, and observed 45% of cells showing more than 6puncta compared to 20% cells showing 6 puncta using only sgMUC4 (FIG.

13A-13B). These results suggest that it should be possible to perform multicolor imaging of multiple genomic loci using orthogonal Cas9 proteins fused to distinct fluorescent proteins.

Figure 14A:
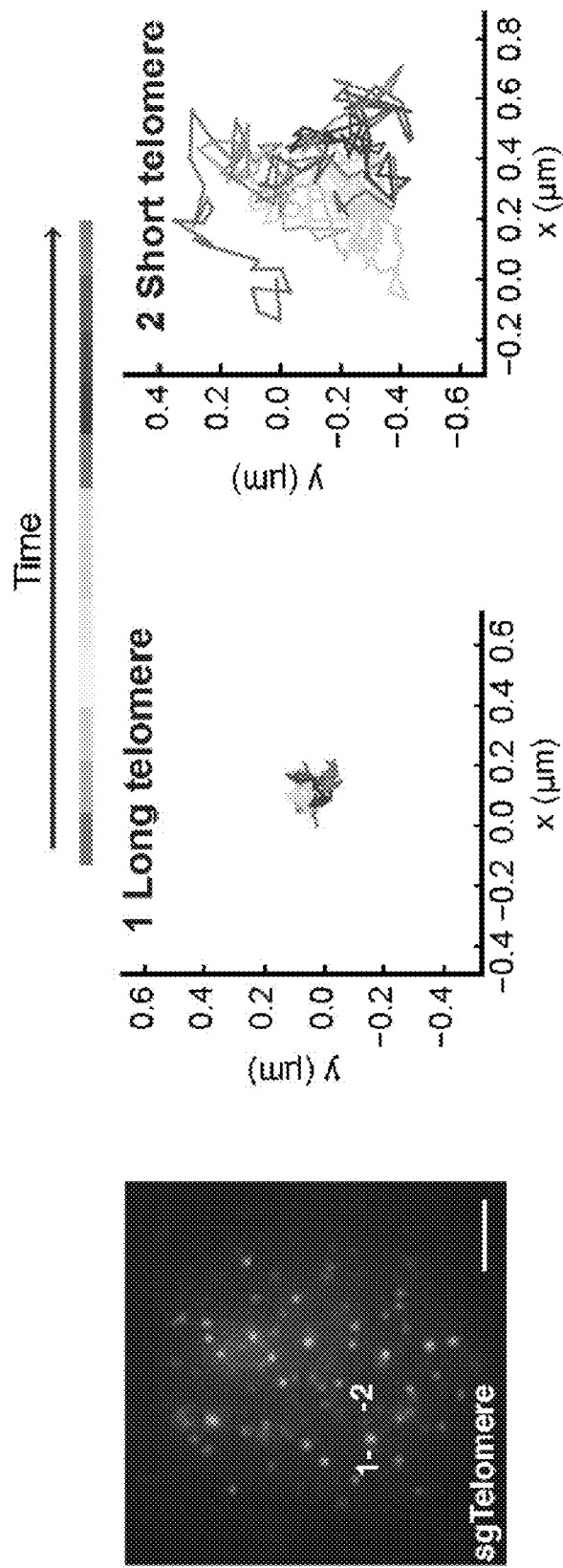
Figures 14F, 14G, 14H:
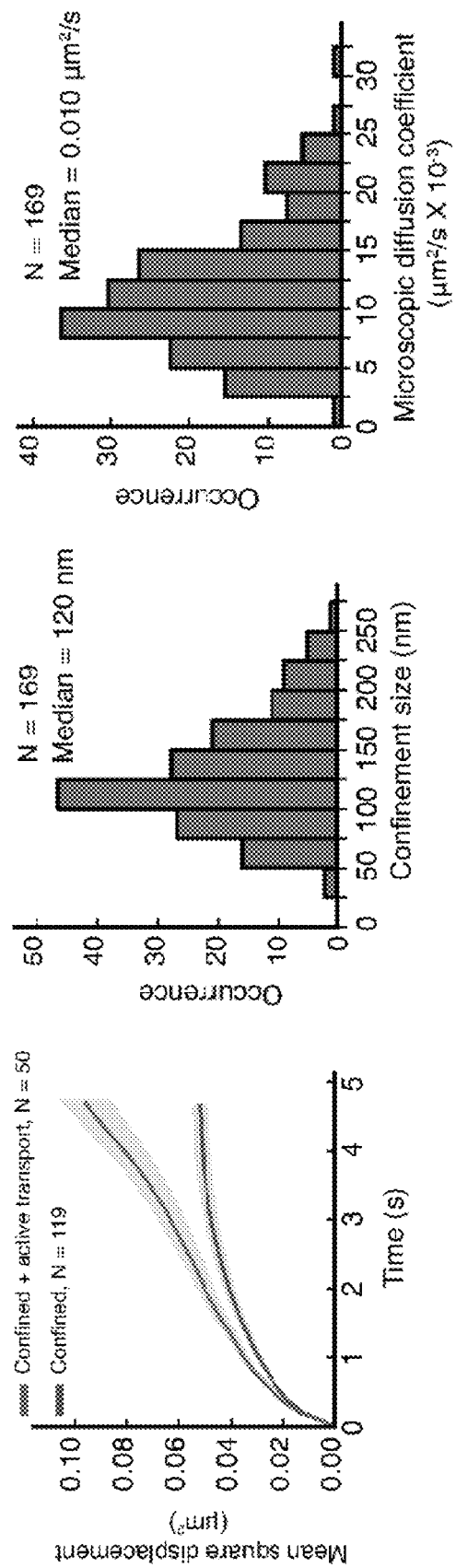

CRISPR imaging offers a unique non-invasive platform for tracking the dynamics of genetic elements in living cells. We performed a high-frequency (0.2 s per frame) time-lapse microscopy to track telomere dynamics in living cells over 40s (FIG. 14A). Consistent with previous results using GFP-fused TRF1 (Wang, et al., 2008), a native telomere binding protein, CRISPR-imaging analysis revealed similar movement speed and two dimensional displacement of telomeres(FIG. 14B-D). Furthermore, long telomeres, as defined by higher fluorescent surface area, showed slower movement speeds. We also tracked individual MUC4 loci movement (FIG. 14E). Our analysis discerned two distinct movement modes: confined diffusion and active transport of confined diffusion (FIG. 14F). 80% of detected MUC4 loci followed confined diffusion, suggesting the movement of local chromatin is modulated by nuclear factors (FIG. 14G). The median speed was 0.011 um$^2$/s as defined by diffusion coefficient (FIG. 14H). This demonstrates the power of using CRISPR to directly visualize the local movement and the segregation process of chromosomes during cell division.

The ability to use CRISPR sgRNAs for sequence-specifically visualizing genetic elements in living cells defines a new class of genome imaging tools. In this study, we have shown that a nuclease-deactivated *S. pyogenes* Cas9 fused with fluorescent proteins can be used to flexibly image both repetitive and non-repetitive genetic elements, which can be potentially applied to image any genomic sequence of interest. Our technology relies on RNA-directed local enrichment of fluorescence signals, which robustly filters the off-target effects of the CRISPR system (Hsu, et al., 2013). The use of orthogonal Cas9 proteins should further allow multiplexed detection of multiple genetic events. The method is capable of tracking the dynamic movement of an arbitrary genomic region in living cells, opening doors to a fuller understanding of how genomes are organized in vivo and how they are dynamically regulated in the cell nucleus. Combined with technologies using CRISPR for gene editing and regulation, the CRISPR imaging technology here offers a universal platform for using RNAs to modify, modulate and label human genomes.

Supplemental Methods
Plasmid Construction

The DNA sequence encoding the Cas9 nuclease harboring inactivating D10A and H840A substitutions (dCas9), derived from *Streptococcus pyogenes*, was fused with EGFP and two SV40 nuclear localization sequences (NLS) at different positions. Using standard ligation-independent cloning, we cloned these three fusion proteins into the TRE response vector with a PTRE3G promoter (Tet-on 3G inducible expression system, Clontech). sgRNAs were cloned into a lentiviral U6-based expression vector derived from pSico, which coexpressm Cherry from a CMV promoter. The sgRNA (old design) expression plasmids were cloned by inserting annealed primers into the vector digested by BstXI and XhoI. The optimized sgRNAs expression constructs were directly ordered as gBlocks (IDT) and clone into the lentiviral U6-based expression vector digested by XbaI/BamHI.

The 73 sgRNAs targeting non-repetitive sequence of MUC4 were cloned into the same sgRNA expression vector by amplifying the insertions using a same reverse primer but different forward primers containing the unique spacer sequence right after the BstXI site and the optimized sgRNA as the template. The PCR fragments were cloned into the vector by BstXI and XhoI.

Cell Culture

Human embryonic kidney (HEK) cell line 293T, human renal cancer cell lineUMUC3 and Hela cells were maintained in Dulbecco's modified Eagle medium (DMEM) with high glucose in 10% FBS. Human retinal pigment epithelium (RPE) cells were maintained in DMEM with GlutaMAX1 in 10% FBS. All cells were maintained at 37° C. and 5% CO2 in a humidified incubator.

Viral Production and Stable Expression of dCas9 and sgRNA

For viral production, 293T cells were seeded into T75 flask one day prior to transfection. 1 μg of pMD2.G plasmid (virus envelope plasmid), 8 μg of pCMV-dR8.91 (virus packaging plasmid) and 9 μg of the lentivector (Tet-on 3G, dCas9-EGFP, GFP-TRF1, sgRNA or TIN-2 shRNA) were cotransfected into 293 T cells using FuGENE (Promega) following the manufacture's recommended protocol. Virus was harvested 48 hours post-transfection. For virus infection, culture cells were incubated with culture medium-diluted virus supernatant supplemented with 5 μg/ml polybrene for 12 hours.

RPE, UMUC3 and HeLa cell lines stably expressing dCas9-EGFP were generated by infecting the cells with lentivirus that co-packaged the two expression vectors of dCas9-EGFP and transactivator protein. Clonal cells expressing dCas9-EGFP in the inducible system for each cell line were generated by picking a single cell colony. The clones with low basal level expression of dCas9-EGFP were selected for CRISPR imaging. To label telomeres and the repetitive regions of MUC1 or MUC4, the selected clonal cell lines were infected with 100111 lentivirus with individual sgRNAs in each 8-well of chambered cover glass. To label the non-repetitive region of MUC4, five or six of sgRNA plasmids were co-packaged in the same lentivirus. The dCas9 expression cells were infected with a mixture of lentivirus including 16, 26, 36 or 73 sgRNAs.

Immunostaining

Cells were fixed in 4% paraformaldehyde, permeabilized with 0.5% NP-40 in phosphate buffered saline (PBS) for 10 minutes, washed with PBS for 5 minutes, blocked in 0.2% cold water fish gelatin and 0.5% bovine serum albumin (BSA) for 20 minutes, incubated with the primary antibody in blocking buffer at 4° C. overnight, washed three times and then incubated with Alexa647-conjugated secondary antibody at room temperature for 1 hour, washed again and stained with DAPI. Primary and secondary antibodies used in this study were anti-TRFP2 (E-20, sc-32106, Santa Cruz Biotechnology) and anti-53BP1.

Fluorescence In Situ Hybridization (FISH) and IF with PNA FISH

Oligo FISH was performed according to standard protocols. Briefly, cells were fixed with 4% paraformaldehyde, incubated with 0.7% Triton X-100, 0.1% Saponin in 2×SSC for 30 min at RT for permeabilization of the nuclear membrane, washed with 2×SSC twice, treated with RNase A at 37° C. for 1 h, washed again with 2×SSC and equilibrated with PBS for 5 min before dehydration by consecutive 5 min incubations in 70%, 85% and 100% ethanol. After air drying, cells were heated at 80° C. for 5 min in 70% formamide/2×SSC, washed using an ethanol series (ice cold; 70, 80, 95%). After aird rying, Cy3- or Cy5-labeled Oligo FISH probe (around 20 bp, each oligo has one molecule of Cy3 or Cy5 conjugated to its 5 prime end) in hybridizing solution (10% dextran sulfate, 50% formomide, 500 ng/ml Salmon sperm DNA in 2×SSC buffer), at a final concentration of 2 ng/μl, was added to the sample and incubated overnight at 37° C. After hybridization, cells were washed three times with 2×SSC for three times and finally stained with DAPI.

For immunofluorescence (IF) with peptide nucleic acid (PNA) FISH, after incubation with primary and secondary antibodies, telomere PNA-FISH was performed as described in Diolaiti et al (beginning after the pepsin treatment).

Optical Setup and Image Acquisition

Cells were seeded onto 8-Well Lab-Tek II chambered cover glass 24 hours before lentivirus infection. The imaging of telomeres and Mucin genes was performed 48 hours post-infection of sgRNAs. The samples with fixation were imaged at a frame rate of 5 Hz with 50 frames. The final image was generated by averaging the 50 frames. To make a projection image, 3 μm Z-stack at 0.4 μm steps were acquired. Right before live cell imaging, the culture medium was replaced with medium without phenol red. Images were recorded at a frame rate of 5 Hz. 600 frames were acquired for the dynamic analysis. During the imaging session, the temperature was maintained at 37° C. with an environmental chamber.

Imaging Analysis

To quantify the colocalization of 53BP1 and PNA-FISH at the telomeres, images were taken on a DeltaVision deconvolution microscope (Applied Precision/GE) with a 100×1.40 NA Plan Apo objective (Olympus). Identification, measurement of areas and intensity, and colocalization analysis of telomeres and 53BP1 foci were performed in CellProfiler (Carpenter 2006, specific pipelines available upon request); quantification and statistical comparison were carried out using custom Python software.

REFERENCES

1. T. Misteli, *Cell* 128, 787 (2007).
2. T. Misteli, *Cell* 152, 1209 (2013).
3. M. L. Pardue, J. G. Gall, *Proceedings of the National Academy of Sciences of the United States of America* 64, 600 (1969).
4. C. C. Robinett et al., *The Journal of cell biology* 135, 1685 (1996).
5. X. Wang et al., *Epigenetics & chromatin* 1, 4 (2008).
6. R. Barrangou et al., *Science* 315, 1709 (2007).
7. B. Wiedenheft, S. H. Sternberg, J. A. Doudna, *Nature* 482, 331 (2012).
8. E. Deltcheva et al., *Nature* 471, 602 (2011).
9. M. Jinek et al., *Science* 337, 816 (2012).
10. L. Cong et al., *Science* 339, 819 (2013).
11. P. Mali et al., *Science* 339, 823 (2013).
12. H. Wang et al., *Cell* 153, 910 (2013).
13. L. S. Qi et al., *Cell* 152, 1173 (2013).
14. L. A. Gilbert et al., *Cell* 154, 442 (2013).
15. R. K. Moyzis et al., *Proceedings of the National Academy of Sciences of the United States of America* 85, 6622 (1988).
16. S. Nielsen, Y. Yuzenkova, N. Zenkin, *Science* 340, 1577 (2013).
17. J. D. Griffith et al., *Cell* 97, 503 (1999).
18. F. d'Adda di Fagagna et al., *Nature* 426, 194 (2003).
19. S. H. Kim, P. Kaminker, J. Campisi, *Nature genetics* 23, 405 (1999).
20. H. Vaziri, S. Benchimol, *Current biology: CB* 8, 279 (1998).
21. M. A. Hollingsworth, B. J. Swanson, *Nature reviews. Cancer* 4, 45 (2004).
22. S. Nollet et al., *The Biochemical journal* 332 (Pt 3), 739 (1998).
23. S. J. Gendler et al., *The Journal of biological chemistry* 265, 15286 (1990).
24. P. D. Hsu et al., *Nature biotechnology* 31, 827 (2013).

All patents, patent applications, and other publications, including GenBank Accession Numbers, cited in this application are incorporated by reference in the entirety for all purposes.

What is claimed is:

1. A composition for nucleic acid modification or detection comprising the small guide RNA (sgRNA) molecule comprising SEQ ID NO:4 or a sequence having 2 or fewer nucleotide substitutions compared to SEQ ID NO:4, wherein the sgRNA comprises:
   a 5' stem-loop region, wherein the 5' stem-loop region comprises a 5' stem of between about 10 and 30 complementary base pairs, wherein the 5' stem does not contain four consecutive uracil nucleotides, and wherein the 5' stem comprises an elongated 5' stem;
   a 3' stem-loop region; and
   a transcription termination signal sequence,
   and wherein, the composition further comprises a small guide RNA-mediated nuclease, wherein the sgRNA and the small guide RNA-mediated nuclease form a complex.

2. The composition of claim 1, wherein the nuclease is nuclease defective, thereby forming a complex configured to bind to, but not cleave or nick, a target nucleic acid substantially complementary to the binding region of the small guide RNA.

3. The composition of claim 2, wherein the nuclease defective composition comprises a Cas9 protein containing a mutation at one or more of the following residues: D10, G12, G17, E762, H840, N854, N863, H982, H983, A984, D986, or A987.

4. The composition of claim 3, wherein the nuclease defective composition comprises a Cas9 protein containing a mutation at two or more of the following residues: D10, G12, G17, E762, H840, N854, N863, H982, H983, A984, D986, and A987.

5. The composition of claim 4, wherein the nuclease defective composition comprises a Cas9 protein containing a D10A and a H840A mutation.

6. The composition of claim 2 wherein the nuclease defective composition comprises a labeled Cas9 protein.

7. The composition of claim 6, wherein the labeled Cas9 protein comprises a fluorophore.

8. The composition of claim 7, wherein the fluorophore is a fluorescent protein.

9. The composition of claim 1, wherein the nuclease has nuclease activity.

10. The composition of claim 9, wherein the small guide RNA-mediated nuclease has nicking activity, but is defective at catalyzing double stranded breaks in the target sequence.

11. The composition of claim 9, wherein the small guide RNA-mediated nuclease comprises a Cas9 protein containing a mutation at one or more of the following residues D10, G12, G17, E762, H840, N854, N863, H982, H983, A984, D986, or A987.

12. A host cell comprising the composition of claim 1.

13. The host cell of claim 12, wherein the small guide RNA-mediated nuclease is labeled.

14. The host cell of claim 13, wherein the small guide RNA-mediated nuclease is labeled with a fluorophore.

15. A kit comprising the composition of claim 1.

* * * * *